United States Patent
Berckmans, III et al.

(10) Patent No.: US 8,257,083 B2
(45) Date of Patent: Sep. 4, 2012

(54) METHODS FOR PLACING AN IMPLANT ANALOG IN A PHYSICAL MODEL OF THE PATIENT'S MOUTH

(75) Inventors: Bruce Berckmans, III, Palm Beach Gardens, FL (US); Zachary B. Suttin, Palm Beach Gardens, FL (US); Dan P. Rogers, North Palm Beach, FL (US); T. Tait Robb, Stewart, FL (US); Alexis C. Goolik, Palm Beach Gardens, FL (US)

(73) Assignee: Biomet 3i, LLC, Palm Beach Gardens, FL (US)

( * ) Notice: Subject to any disclaimer, the term of this patent is extended or adjusted under 35 U.S.C. 154(b) by 923 days.

(21) Appl. No.: 12/070,922

(22) Filed: Feb. 22, 2008

(65) Prior Publication Data

US 2008/0153067 A1 Jun. 26, 2008

Related U.S. Application Data

(63) Continuation-in-part of application No. 11/585,705, filed on Oct. 24, 2006, now Pat. No. 7,661,956.

(60) Provisional application No. 60/729,506, filed on Oct. 24, 2005.

(51) Int. Cl.
*A61C 11/00* (2006.01)
(52) U.S. Cl. .................................. 433/213
(58) Field of Classification Search .......... 433/172–176, 433/213–214, 218–223; 700/245–264; 901/2; 264/16–20; 345/419
See application file for complete search history.

(56) References Cited

U.S. PATENT DOCUMENTS

| | | | |
|---|---|---|---|
| 3,906,634 A | 9/1975 | Aspel | 433/24 |
| 3,919,772 A | 11/1975 | Lenczycki | 32/10 A |
| 3,958,471 A | 5/1976 | Muller | |
| 4,011,602 A | 3/1977 | Rybicki et al. | |
| 4,056,585 A | 11/1977 | Waltke | 433/74 |
| 4,086,701 A | 5/1978 | Kawahara et al. | |
| 4,177,562 A | 12/1979 | Miller et al. | |
| 4,294,544 A | 10/1981 | Altschuler et al. | 356/376 |
| 4,306,862 A | 12/1981 | Knox | |

(Continued)

FOREIGN PATENT DOCUMENTS

DE 10029256 11/2000
(Continued)

OTHER PUBLICATIONS

BIOMET 3i—Manual entitled "Navigator™ System for CT Guided Surgery Manual", Revision A Oct. 2007—34 pages.

*Primary Examiner* — Todd Manahan
*Assistant Examiner* — Matthew Nelson
(74) *Attorney, Agent, or Firm* — Nixon Peabody LLP

(57) ABSTRACT

A method of placing a dental implant analog in a physical model for use in creating a dental prosthesis is provided. The physical model, which is usually based on an impression of the patient's mouth or a scan of the patient's mouth, is prepared. The model is scanned. A three-dimensional computer model of the physical model is created and is used to develop the location of the dental implant. A robot then modifies the physical model to create an opening for the implant analog. The robot then places the implant analog within the opening at the location dictated by the three-dimensional computer model.

16 Claims, 31 Drawing Sheets

U.S. PATENT DOCUMENTS

| | | | |
|---|---|---|---|
| 4,325,373 A | 4/1982 | Slivenko et al. | 606/96 |
| 4,341,312 A | 7/1982 | Scholer | |
| 4,364,381 A | 12/1982 | Sher et al. | 606/96 |
| 4,439,152 A | 3/1984 | Small | 433/173 |
| 4,543,953 A | 10/1985 | Slocum et al. | 607/32 |
| 4,547,157 A | 10/1985 | Driskell | |
| 4,571,180 A | 2/1986 | Kulick | 433/72 |
| 4,611,288 A | 9/1986 | Duret et al. | 364/474 |
| 4,624,673 A | 11/1986 | Meyer | |
| 4,663,720 A | 5/1987 | Duret et al. | 364/474 |
| 4,713,004 A | 12/1987 | Linkow et al. | |
| 4,756,689 A | 7/1988 | Lundgren | 433/173 |
| 4,758,161 A | 7/1988 | Niznick | |
| 4,767,331 A | 8/1988 | Hoe | |
| 4,772,204 A | 9/1988 | Soderberg | |
| 4,821,200 A | 4/1989 | Öberg | 364/474 |
| 4,842,518 A | 6/1989 | Linkow et al. | |
| 4,850,870 A | 7/1989 | Lazzara et al. | |
| 4,850,873 A | 7/1989 | Lazzara et al. | |
| 4,854,872 A | 8/1989 | Detsch | |
| 4,856,994 A | 8/1989 | Lazzara et al. | |
| 4,872,839 A | 10/1989 | Brajnovic | |
| 4,906,191 A | 3/1990 | Soderberg | |
| 4,906,420 A | 3/1990 | Brajnovic | 264/17 |
| 4,931,016 A | 6/1990 | Sillard | 433/172 |
| 4,935,635 A | 6/1990 | O'Harra | 350/560 |
| 4,961,674 A | 10/1990 | Wang et al. | 408/14 |
| 4,964,770 A | 10/1990 | Steinbichler et al. | 433/223 |
| 4,986,753 A | 1/1991 | Sellers | 433/172 |
| 4,988,297 A | 1/1991 | Lazzara et al. | |
| 4,988,298 A | 1/1991 | Lazzara et al. | |
| 4,998,881 A | 3/1991 | Lauks | 433/173 |
| 5,000,685 A | 3/1991 | Brajnovic | |
| 5,006,069 A | 4/1991 | Lazzara et al. | |
| 5,015,183 A | 5/1991 | Fenick | 433/73 |
| 5,015,186 A | 5/1991 | Detsch | |
| 5,030,096 A | 7/1991 | Hurson et al. | |
| 5,035,619 A | 7/1991 | Daftary | |
| 5,040,982 A | 8/1991 | Stefan-Dogar | 433/169 |
| 5,040,983 A | 8/1991 | Binon | |
| 5,064,375 A | 11/1991 | Jörnéus | |
| 5,071,351 A | 12/1991 | Green, Jr. et al. | |
| 5,073,111 A | 12/1991 | Daftary | |
| 5,087,200 A | 2/1992 | Brajnovic et al. | 433/173 |
| 5,100,323 A | 3/1992 | Friedman et al. | |
| 5,104,318 A | 4/1992 | Piche et al. | |
| 5,106,300 A | 4/1992 | Voitik | |
| 5,122,059 A | 6/1992 | Dürr et al. | |
| 5,125,839 A | 6/1992 | Ingber et al. | |
| 5,125,841 A | 6/1992 | Carlsson et al. | |
| 5,133,660 A | 7/1992 | Fenick | 433/76 |
| 5,135,395 A | 8/1992 | Marlin | |
| 5,145,371 A | 9/1992 | Jörnéus | |
| 5,145,372 A | 9/1992 | Daftary et al. | |
| 5,176,516 A | 1/1993 | Koizumi | 433/72 |
| 5,188,800 A | 2/1993 | Green, Jr. et al. | |
| 5,195,892 A | 3/1993 | Gersberg | |
| 5,205,745 A | 4/1993 | Kamiya et al. | |
| 5,209,659 A | 5/1993 | Friedman et al. | |
| 5,209,666 A | 5/1993 | Balfour et al. | |
| 5,213,502 A | 5/1993 | Daftary | |
| 5,237,998 A | 8/1993 | Duret et al. | 128/665 |
| 5,246,370 A | 9/1993 | Coatoam | |
| 5,257,184 A | 10/1993 | Mushabac | 364/413 |
| 5,281,140 A | 1/1994 | Niznick | 433/172 |
| 5,286,195 A | 2/1994 | Clostermann | |
| 5,286,196 A | 2/1994 | Brajnovic et al. | 433/173 |
| 5,292,252 A | 3/1994 | Nickerson et al. | |
| 5,297,963 A | 3/1994 | Dafatry | |
| 5,302,125 A | 4/1994 | Kownacki et al. | 433/172 |
| 5,312,254 A | 5/1994 | Rosenlicht | |
| 5,312,409 A | 5/1994 | McLaughlin et al. | 606/86 |
| 5,316,476 A | 5/1994 | Krauser | |
| 5,320,529 A | 6/1994 | Pompa | 433/76 |
| 5,328,371 A | 7/1994 | Hund et al. | 433/173 |
| 5,334,024 A | 8/1994 | Niznick | |
| 5,336,090 A | 8/1994 | Wilson, Jr. et al. | |
| 5,338,196 A | 8/1994 | Beaty et al. | |
| 5,338,198 A | 8/1994 | Wu et al. | |
| 5,343,391 A | 8/1994 | Mushabac | 364/413.28 |
| 5,344,457 A | 9/1994 | Pilliar et al. | |
| 5,350,297 A | 9/1994 | Cohen | 433/76 |
| 5,359,511 A | 10/1994 | Schroeder et al. | 364/413.28 |
| 5,362,234 A | 11/1994 | Salazar et al. | |
| 5,362,235 A | 11/1994 | Daftary | |
| 5,368,483 A | 11/1994 | Sutter et al. | |
| 5,370,692 A | 12/1994 | Fink | |
| 5,372,502 A | 12/1994 | Massen et al. | 433/215 |
| 5,386,292 A | 1/1995 | Massen et al. | 354/376 |
| 5,413,481 A | 5/1995 | Göppel et al. | 433/214 |
| 5,417,569 A | 5/1995 | Perisse | 433/173 |
| 5,417,570 A | 5/1995 | Zuest et al. | |
| 5,419,702 A | 5/1995 | Beaty et al. | |
| 5,431,567 A | 7/1995 | Datary | |
| 5,437,551 A | 8/1995 | Chalifoux | |
| 5,440,393 A | 8/1995 | Wenz | 356/376 |
| 5,452,219 A | 9/1995 | Dehoff et al. | 700/163 |
| 5,458,488 A | 10/1995 | Chalifoux | |
| 5,476,382 A | 12/1995 | Daftary | |
| 5,476,383 A | 12/1995 | Beaty et al. | |
| 5,492,471 A | 2/1996 | Singer | |
| 5,516,288 A | 5/1996 | Sichler et al. | 433/173 |
| 5,527,182 A | 6/1996 | Willoughby | |
| 5,533,898 A | 7/1996 | Mena | 433/173 |
| 5,538,426 A | 7/1996 | Harding et al. | |
| 5,547,377 A | 8/1996 | Daftary | |
| 5,556,278 A | 9/1996 | Meitner | 433/75 |
| 5,564,921 A | 10/1996 | Marlin | |
| 5,564,924 A | 10/1996 | Kwan | |
| 5,569,578 A | 10/1996 | Mushabac | 433/215 |
| 5,575,656 A | 11/1996 | Hajjar | 433/219 |
| 5,580,244 A | 12/1996 | White | 433/37 |
| 5,580,246 A | 12/1996 | Fried | 433/172 |
| 5,595,703 A | 1/1997 | Swaelens et al. | 264/401 |
| 5,613,832 A | 3/1997 | Su | 416/244 |
| 5,613,852 A | 3/1997 | Bavitz | 433/173 |
| 5,630,717 A | 5/1997 | Zuest | 433/172 |
| 5,636,986 A | 6/1997 | Pezeshkian | 433/76 |
| 5,651,675 A | 7/1997 | Singer | 433/172 |
| 5,652,709 A | 7/1997 | Andersson et al. | 700/161 |
| 5,658,147 A | 8/1997 | Phimmasone | |
| 5,662,476 A | 9/1997 | Ingber et al. | |
| 5,674,069 A | 10/1997 | Osorio | |
| 5,674,071 A | 10/1997 | Beaty et al. | |
| 5,674,073 A | 10/1997 | Ingber et al. | |
| 5,681,167 A | 10/1997 | Lazarof | |
| 5,685,715 A | 11/1997 | Beaty et al. | |
| 5,688,283 A | 11/1997 | Knapp | 606/96 |
| 5,704,936 A | 1/1998 | Mazel | 606/254 |
| 5,718,579 A | 2/1998 | Kennedy | 433/75 |
| 5,725,376 A | 3/1998 | Poirier | 433/172 |
| 5,733,124 A | 3/1998 | Kwan | 433/173 |
| 5,741,215 A | 4/1998 | Fink | |
| 5,743,916 A | 4/1998 | Greenberg | 606/102 |
| 5,759,036 A | 6/1998 | Hinds | |
| 5,762,125 A | 6/1998 | Mastrorio | 164/4.1 |
| 5,762,500 A | 6/1998 | Lazarof | 433/213 |
| 5,768,134 A | 6/1998 | Swaelens et al. | |
| 5,769,636 A | 6/1998 | Di Sario | 433/213 |
| 5,791,902 A | 8/1998 | Lauks | 433/165 |
| 5,800,168 A | 9/1998 | Cascione et al. | 433/75 |
| 5,813,858 A | 9/1998 | Singer | |
| 5,823,778 A | 10/1998 | Schmitt et al. | 433/214 |
| 5,842,859 A | 12/1998 | Palacci | 433/72 |
| 5,846,079 A | 12/1998 | Knode | |
| 5,851,115 A | 12/1998 | Carlsson et al. | |
| 5,857,853 A | 1/1999 | Van Nifterick et al. | 433/213 |
| 5,871,358 A | 2/1999 | Ingber et al. | |
| 5,873,722 A | 2/1999 | Lazzara et al. | |
| 5,876,204 A | 3/1999 | Day et al. | 433/173 |
| 5,885,078 A | 3/1999 | Cagna et al. | 433/172 |
| 5,888,034 A | 3/1999 | Greenberg | 408/115 |
| 5,904,483 A | 5/1999 | Wade | 433/173 |
| 5,915,962 A | 6/1999 | Rosenlicht | 433/76 |
| 5,927,982 A | 7/1999 | Kruger | 433/215 |
| 5,938,443 A | 8/1999 | Lazzara et al. | |
| 5,954,769 A | 9/1999 | Rosenlicht | 623/16.11 |

| Patent | Kind | Date | Inventor | Class |
|---|---|---|---|---|
| 5,964,591 | A | 10/1999 | Beaty et al. | 433/173 |
| 5,967,777 | A | 10/1999 | Klein et al. | 433/75 |
| 5,984,681 | A | 11/1999 | Huang | 433/174 |
| 5,989,025 | A | 11/1999 | Conley | 433/76 |
| 5,989,029 | A | 11/1999 | Osorlo | |
| 5,989,258 | A | 11/1999 | Hattori | 606/80 |
| 5,997,681 | A | 12/1999 | Kinzie | 156/263 |
| 6,000,939 | A | 12/1999 | Ray et al. | 433/27 |
| 6,008,905 | A | 12/1999 | Breton et al. | 356/402 |
| 6,068,479 | A | 5/2000 | Kwan | 433/173 |
| 6,099,311 | A | 8/2000 | Wagner et al. | 433/163 |
| 6,099,313 | A | 8/2000 | Dorken et al. | 433/175 |
| 6,099,314 | A | 8/2000 | Kopelman et al. | 433/213 |
| 6,120,293 | A | 9/2000 | Lazzara et al. | |
| 6,129,548 | A | 10/2000 | Lazzara et al. | |
| 6,135,773 | A | 10/2000 | Lazzara | |
| 6,142,782 | A | 11/2000 | Lazarof | 433/174 |
| 6,174,168 | B1 | 1/2001 | Dehoff et al. | 433/202.1 |
| 6,175,413 | B1 | 1/2001 | Lucas | 356/614 |
| 6,190,169 | B1 | 2/2001 | Bluemli et al. | 433/172 |
| 6,197,410 | B1 | 3/2001 | Vallittu et al. | 428/292.1 |
| 6,200,125 | B1 | 3/2001 | Akutagawa | 425/462 |
| 6,206,693 | B1 | 3/2001 | Hultgren | 433/38 |
| 6,210,162 | B1 | 4/2001 | Chishti | |
| 6,217,334 | B1 | 4/2001 | Hultgren | |
| 6,227,859 | B1 | 5/2001 | Sutter | 433/173 |
| 6,283,753 | B1 | 9/2001 | Willoughby | 433/172 |
| 6,287,119 | B1 | 9/2001 | van Nifterick | 433/213 |
| 6,296,483 | B1 | 10/2001 | Champleboux | 433/75 |
| 6,305,939 | B1 * | 10/2001 | Dawood | 433/174 |
| 6,319,000 | B1 | 11/2001 | Branemark | 433/75 |
| 6,322,728 | B1 | 11/2001 | Brodkin | |
| 6,382,975 | B1 | 5/2002 | Poirier | 433/173 |
| 6,402,707 | B1 | 6/2002 | Ernst | 600/590 |
| 6,431,867 | B1 * | 8/2002 | Gittelson et al. | 433/173 |
| 6,488,503 | B1 | 12/2002 | Lichkus et al. | 433/202.1 |
| 6,497,574 | B1 | 12/2002 | Miller | 433/213 |
| 6,540,784 | B2 | 4/2003 | Barlow | |
| 6,558,162 | B1 | 5/2003 | Porter et al. | |
| 6,568,936 | B2 | 5/2003 | MacDougald | 433/223 |
| 6,575,751 | B1 | 6/2003 | Lehmann et al. | 433/223 |
| 6,594,539 | B1 | 7/2003 | Geng | 700/117 |
| 6,610,079 | B1 | 8/2003 | Li et al. | 606/232 |
| 6,619,958 | B2 | 9/2003 | Beaty et al. | 433/173 |
| 6,629,840 | B2 | 10/2003 | Chishti | |
| 6,634,883 | B2 | 10/2003 | Ranalli | 433/50 |
| 6,648,640 | B2 | 11/2003 | Rubbert et al. | 433/24 |
| 6,671,539 | B2 | 12/2003 | Gateno et al. | 600/426 |
| 6,672,870 | B2 | 1/2004 | Knapp | 433/76 |
| 6,688,887 | B2 | 2/2004 | Morgan | 433/173 |
| 6,691,764 | B2 | 2/2004 | Embert | |
| 6,743,491 | B2 | 6/2004 | Cirincione et al. | 428/34.6 |
| 6,755,652 | B2 | 6/2004 | Nanni | 433/196 |
| 6,772,026 | B2 | 8/2004 | Bradbury | |
| 6,776,614 | B2 | 8/2004 | Wiechmann et al. | 433/24 |
| 6,783,359 | B2 | 8/2004 | Kapit | 433/3 |
| 6,790,040 | B2 | 9/2004 | Amber et al. | 433/173 |
| 6,793,491 | B2 | 9/2004 | Klein et al. | 433/173 |
| 6,808,659 | B2 | 10/2004 | Schulman | |
| 6,814,575 | B2 | 11/2004 | Poirier | 433/75 |
| 6,821,462 | B2 | 11/2004 | Schulman et al. | 264/16 |
| 6,829,498 | B2 | 12/2004 | Kipke et al. | 600/378 |
| D503,804 | S | 4/2005 | Phleps et al. | |
| 6,882,894 | B2 | 4/2005 | Durbin et al. | 700/118 |
| 6,885,464 | B1 | 4/2005 | Pfeiffer et al. | |
| 6,902,401 | B2 | 6/2005 | Jorneus et al. | 433/173 |
| 6,913,463 | B2 | 7/2005 | Blacklock | 433/72 |
| 6,926,442 | B2 | 8/2005 | Stöckl | |
| 6,926,525 | B1 | 8/2005 | Ronvig | 433/76 |
| 6,939,489 | B2 | 9/2005 | Moszner et al. | 264/16 |
| 6,942,699 | B2 | 9/2005 | Stone et al. | 623/19.14 |
| 6,953,383 | B2 | 10/2005 | Rothenberger | |
| 6,957,118 | B2 | 10/2005 | Kopelman et al. | 700/118 |
| 6,966,772 | B2 | 11/2005 | Malin et al. | 433/75 |
| 6,970,760 | B2 | 11/2005 | Wolf et al. | 700/163 |
| 6,971,877 | B2 | 12/2005 | Harter | 433/75 |
| 6,994,549 | B2 | 2/2006 | Brodkin et al. | 433/202.1 |
| 7,010,150 | B1 | 3/2006 | Pfeiffer et al. | |
| 7,010,153 | B2 | 3/2006 | Zimmermann | |
| 7,012,988 | B2 | 3/2006 | Adler et al. | |
| 7,018,207 | B2 | 3/2006 | Prestipino | 433/213 |
| 7,021,934 | B2 | 4/2006 | Aravena | 433/173 |
| 7,029,275 | B2 | 4/2006 | Rubbert et al. | 433/24 |
| 7,044,735 | B2 | 5/2006 | Malin | 433/75 |
| 7,056,115 | B2 | 6/2006 | Phan et al. | 433/24 |
| 7,056,472 | B1 | 6/2006 | Behringer | |
| 7,059,856 | B2 | 6/2006 | Marotta | 433/214 |
| 7,066,736 | B2 | 6/2006 | Kumar et al. | 433/173 |
| 7,084,868 | B2 | 8/2006 | Farag et al. | 345/419 |
| 7,086,860 | B2 * | 8/2006 | Schuman et al. | 433/75 |
| 7,097,451 | B2 | 8/2006 | Tang | 433/76 |
| 7,104,795 | B2 | 9/2006 | Dadi | 433/72 |
| 7,110,844 | B2 | 9/2006 | Kopelman et al. | 700/118 |
| 7,112,065 | B2 | 9/2006 | Kopelman et al. | 433/213 |
| 7,118,375 | B2 | 10/2006 | Durbin et al. | 433/68 |
| D532,991 | S | 12/2006 | Gozzi et al. | |
| 7,153,132 | B2 | 12/2006 | Tedesco | 433/76 |
| 7,153,135 | B1 | 12/2006 | Thomas | 433/213 |
| 7,163,443 | B2 | 1/2007 | Basler et al. | |
| 7,175,434 | B2 | 2/2007 | Brajnovic | 433/174 |
| 7,175,435 | B2 | 2/2007 | Andersson et al. | |
| 7,178,731 | B2 | 2/2007 | Basler | |
| 7,214,062 | B2 | 5/2007 | Morgan | 433/173 |
| 7,220,124 | B2 | 5/2007 | Taub et al. | 433/213 |
| 7,228,191 | B2 | 6/2007 | Hofmeister et al. | 700/98 |
| 7,236,842 | B2 | 6/2007 | Kopelman et al. | 700/87 |
| 7,281,927 | B2 | 10/2007 | Marotta | 433/213 |
| 7,286,954 | B2 | 10/2007 | Kopelman et al. | 702/152 |
| 7,303,420 | B2 | 12/2007 | Huch et al. | |
| 7,319,529 | B2 | 1/2008 | Babayoff | 356/601 |
| 7,322,746 | B2 | 1/2008 | Beckhaus et al. | |
| 7,322,824 | B2 | 1/2008 | Schmitt | 433/215 |
| 7,324,680 | B2 | 1/2008 | Zimmermann | |
| 7,329,122 | B1 | 2/2008 | Scott | 433/24 |
| 7,333,874 | B2 | 2/2008 | Taub et al. | 700/117 |
| 7,335,876 | B2 | 2/2008 | Eiff et al. | |
| D565,184 | S | 3/2008 | Royzen | |
| 7,367,801 | B2 | 5/2008 | Saliger | |
| 7,379,584 | B2 | 5/2008 | Rubbert et al. | 382/154 |
| D571,471 | S | 6/2008 | Stöckl | |
| 7,381,191 | B2 | 6/2008 | Fallah | 600/590 |
| 7,383,094 | B2 | 6/2008 | Kopelman et al. | 700/118 |
| D575,747 | S | 8/2008 | Abramovich et al. | |
| 7,421,608 | B2 | 9/2008 | Schron | |
| 7,425,131 | B2 | 9/2008 | Amber et al. | |
| 7,429,175 | B2 | 9/2008 | Gittelson | 433/75 |
| 7,435,088 | B2 | 10/2008 | Brajnovic | 433/173 |
| 7,476,100 | B2 | 1/2009 | Kuo | 433/6 |
| 7,481,647 | B2 | 1/2009 | Sambu et al. | 425/436 |
| 7,488,174 | B2 | 2/2009 | Kopelman et al. | 433/213 |
| 7,497,619 | B2 | 3/2009 | Stoeckl | |
| 7,497,983 | B2 | 3/2009 | Khan et al. | 264/673 |
| 7,520,747 | B2 | 4/2009 | Stonisch | 433/215 |
| 7,522,764 | B2 | 4/2009 | Schwotzer | |
| 7,534,266 | B2 | 5/2009 | Kluger | 623/17.11 |
| 7,536,234 | B2 | 5/2009 | Kopelman et al. | 700/118 |
| 7,545,372 | B2 | 6/2009 | Kopelman et al. | 345/419 |
| 7,551,760 | B2 | 6/2009 | Scharlack et al. | 382/128 |
| 7,555,403 | B2 | 6/2009 | Kopelman et al. | 702/152 |
| 7,556,496 | B2 | 7/2009 | Cinader, Jr. et al. | 433/24 |
| 7,559,692 | B2 | 7/2009 | Beckhaus et al. | |
| 7,563,397 | B2 | 7/2009 | Schulman et al. | 264/16 |
| D597,769 | S | 8/2009 | Richter | |
| 7,572,058 | B2 | 8/2009 | Pruss et al. | |
| 7,572,125 | B2 | 8/2009 | Brajnovic | 433/75 |
| 7,574,025 | B2 | 8/2009 | Feldman | 382/128 |
| 7,578,673 | B2 | 8/2009 | Wen et al. | 433/24 |
| 7,580,502 | B2 | 8/2009 | Dalpiaz et al. | |
| 7,581,951 | B2 | 9/2009 | Lehmann et al. | |
| 7,582,855 | B2 | 9/2009 | Pfeiffer | |
| 7,628,537 | B2 | 12/2009 | Schulze-Ganzlin | |
| 7,632,097 | B2 | 12/2009 | Clerck | 433/215 |
| 7,653,455 | B2 | 1/2010 | Cinader, Jr. et al. | 700/119 |
| 7,654,823 | B2 | 2/2010 | Dadi | 433/72 |
| 7,655,586 | B1 | 2/2010 | Brodkin et al. | 501/103 |
| 7,658,610 | B2 | 2/2010 | Knopp | 433/24 |
| 7,661,956 | B2 | 2/2010 | Powell et al. | |
| 7,665,989 | B2 | 2/2010 | Brajnovic et al. | 433/165 |

| | | |
|---|---|---|
| 7,679,723 B2 | 3/2010 | Schwotzer |
| 7,687,754 B2 | 3/2010 | Eiff et al. |
| 7,689,308 B2 | 3/2010 | Holzner et al. ............... 700/97 |
| D614,210 S | 4/2010 | Basler et al. |
| 7,698,014 B2 | 4/2010 | Dunne et al. ............... 700/118 |
| 7,774,084 B2 | 8/2010 | Cinader, Jr. ............... 700/119 |
| 7,780,907 B2 | 8/2010 | Schmidt et al. |
| 7,785,007 B2 | 8/2010 | Stoeckl |
| 7,787,132 B2 | 8/2010 | Körner et al. |
| 7,796,811 B2 | 9/2010 | Orth et al. |
| 7,798,708 B2 | 9/2010 | Erhardt et al. |
| 7,801,632 B2 | 9/2010 | Orth et al. |
| 7,815,371 B2 | 10/2010 | Schulze-Ganzlin |
| 7,824,181 B2 | 11/2010 | Sers |
| D629,908 S | 12/2010 | Jerger et al. |
| 7,855,354 B2 | 12/2010 | Eiff |
| 7,865,261 B2 | 1/2011 | Pfeiffer |
| 7,876,877 B2 | 1/2011 | Stockl |
| 7,901,209 B2 | 3/2011 | Saliger et al. |
| 7,982,731 B2 | 7/2011 | Orth et al. |
| 7,985,119 B2 | 7/2011 | Basler et al. |
| 7,986,415 B2 | 7/2011 | Thiel et al. |
| 7,988,449 B2 | 8/2011 | Amber et al. |
| 8,011,925 B2 | 9/2011 | Powell et al. |
| 8,011,927 B2 | 9/2011 | Merckmans, III et al. |
| 8,026,943 B2 | 9/2011 | Weber et al. |
| 8,038,440 B2 | 10/2011 | Swaelens et al. |
| 8,047,895 B2 | 11/2011 | Basler |
| 8,057,912 B2 | 11/2011 | Basler et al. |
| 8,062,034 B2 | 11/2011 | Hanisch et al. |
| 8,083,522 B2 | 12/2011 | Karkar et al. |
| 2001/0008751 A1 | 7/2001 | Chishti et al. |
| 2001/0034010 A1 | 10/2001 | MacDougald et al. ....... 433/223 |
| 2002/0010568 A1 | 1/2002 | Rubbert et al. ............... 703/6 |
| 2002/0028418 A1 | 3/2002 | Farag et al. ............... 433/29 |
| 2002/0039717 A1 | 4/2002 | Amber et al. |
| 2002/0160337 A1* | 10/2002 | Klein et al. ............... 433/213 |
| 2002/0167100 A1 | 11/2002 | Moszner |
| 2003/0130605 A1 | 7/2003 | Besek ............... 604/1 |
| 2003/0222366 A1 | 12/2003 | Stangel |
| 2004/0029074 A1 | 2/2004 | Brajnovic ............... 433/172 |
| 2004/0048227 A1 | 3/2004 | Brajnovic ............... 433/167 |
| 2004/0180308 A1* | 9/2004 | Ebi et al. ............... 433/173 |
| 2004/0219477 A1 | 11/2004 | Harter ............... 433/75 |
| 2004/0219479 A1 | 11/2004 | Malin et al. ............... 433/75 |
| 2004/0219490 A1 | 11/2004 | Gartner et al. ............... 433/218 |
| 2004/0220691 A1 | 11/2004 | Hofmeister et al. |
| 2004/0241611 A1 | 12/2004 | Amber et al. |
| 2004/0243481 A1 | 12/2004 | Bradbury et al. ............... 705/26 |
| 2004/0259051 A1 | 12/2004 | Brajnovic ............... 433/75 |
| 2005/0023710 A1 | 2/2005 | Brodkin et al. ............... 264/16 |
| 2005/0056350 A1 | 3/2005 | Dolabdjian et al. |
| 2005/0070782 A1 | 3/2005 | Brodkin ............... 600/407 |
| 2005/0084144 A1 | 4/2005 | Feldman ............... 382/128 |
| 2005/0100861 A1 | 5/2005 | Choi et al. ............... 433/165 |
| 2005/0170311 A1 | 8/2005 | Tardieu et al. ............... 433/76 |
| 2005/0271996 A1 | 12/2005 | Sporbert et al. ............... 433/24 |
| 2005/0277089 A1 | 12/2005 | Brajnovic ............... 433/167 |
| 2005/0277090 A1 | 12/2005 | Anderson et al. ............... 433/173 |
| 2005/0277091 A1 | 12/2005 | Andersson et al. ............... 433/213 |
| 2005/0282106 A1 | 12/2005 | Sussman et al. ............... 433/76 |
| 2005/0283065 A1 | 12/2005 | Babayoff ............... 600/407 |
| 2006/0006561 A1 | 1/2006 | Brajnovic ............... 264/17 |
| 2006/0008763 A1 | 1/2006 | Brajnovic ............... 433/76 |
| 2006/0008770 A1 | 1/2006 | Brajnovic et al. ............... 433/141 |
| 2006/0093988 A1 | 5/2006 | Swaelens et al. ............... 433/76 |
| 2006/0094951 A1 | 5/2006 | Dean et al. ............... 600/407 |
| 2006/0127848 A1 | 6/2006 | Sogo et al. ............... 433/173 |
| 2006/0210949 A1 | 9/2006 | Stoop ............... 433/165 |
| 2006/0263741 A1 | 11/2006 | Imgrund et al. ............... 433/24 |
| 2006/0281041 A1 | 12/2006 | Rubbert et al. ............... 433/24 |
| 2007/0015111 A1 | 1/2007 | Kopelman et al. ............... 433/213 |
| 2007/0031790 A1 | 2/2007 | Raby et al. ............... 433/213 |
| 2007/0065777 A1 | 3/2007 | Becker ............... 433/173 |
| 2007/0077532 A1 | 4/2007 | Harter ............... 433/75 |
| 2007/0092854 A1 | 4/2007 | Powell et al. ............... 433/213 |
| 2007/0141525 A1 | 6/2007 | Cinader, Jr. ............... 433/23 |
| 2007/0211081 A1 | 9/2007 | Quadling et al. ............... 345/632 |
| 2007/0218426 A1 | 9/2007 | Quadling et al. ............... 433/223 |
| 2007/0269769 A1 | 11/2007 | Marchesi ............... 433/215 |
| 2007/0281277 A1 | 12/2007 | Brajnovic ............... 433/172 |
| 2008/0038692 A1 | 2/2008 | Andersson et al. ............... 433/167 |
| 2008/0044794 A1 | 2/2008 | Brajnovic ............... 433/174 |
| 2008/0057467 A1 | 3/2008 | Gittelson ............... 433/72 |
| 2008/0070181 A1 | 3/2008 | Abolfathi et al. ............... 433/6 |
| 2008/0085489 A1 | 4/2008 | Schmitt ............... 433/75 |
| 2008/0090210 A1 | 4/2008 | Brajnovic ............... 433/173 |
| 2008/0114371 A1 | 5/2008 | Kluger ............... 606/99 |
| 2008/0118895 A1 | 5/2008 | Brajnovic ............... 433/223 |
| 2008/0124676 A1 | 5/2008 | Marotta ............... 433/174 |
| 2008/0153061 A1 | 6/2008 | Marcello ............... 433/173 |
| 2008/0153065 A1 | 6/2008 | Brajnovic et al. ............... 433/174 |
| 2008/0153069 A1 | 6/2008 | Holzner et al. ............... 433/223 |
| 2008/0176189 A1 | 7/2008 | Stonisch ............... 433/215 |
| 2008/0206714 A1 | 8/2008 | Schmitt ............... 433/215 |
| 2008/0233537 A1 | 9/2008 | Amber et al. |
| 2008/0241798 A1 | 10/2008 | Holzner et al. ............... 433/223 |
| 2008/0261165 A1 | 10/2008 | Steingart et al. ............... 433/24 |
| 2008/0286722 A1 | 11/2008 | Berckmans, III et al. |
| 2008/0300716 A1 | 12/2008 | Kopelman et al. ............... 700/182 |
| 2009/0017418 A1 | 1/2009 | Gittelson ............... 433/75 |
| 2009/0026643 A1 | 1/2009 | Wiest et al. ............... 264/16 |
| 2009/0042167 A1 | 2/2009 | Van Der Zel ............... 433/215 |
| 2009/0081616 A1 | 3/2009 | Pfeiffer ............... 433/215 |
| 2009/0087817 A1 | 4/2009 | Jansen et al. ............... 433/223 |
| 2009/0092948 A1 | 4/2009 | Gantes |
| 2009/0098510 A1 | 4/2009 | Zhang ............... 433/201.1 |
| 2009/0098511 A1 | 4/2009 | Zhang ............... 433/201.1 |
| 2009/0123045 A1 | 5/2009 | Quadling et al. ............... 382/128 |
| 2009/0123887 A1 | 5/2009 | Brajnovic ............... 433/75 |
| 2009/0130630 A1 | 5/2009 | Suttin et al. |
| 2009/0187393 A1 | 7/2009 | Van Lierde et al. |
| 2009/0220134 A1 | 9/2009 | Cahill et al. |
| 2009/0220916 A1 | 9/2009 | Fisker et al. ............... 433/201.1 |
| 2009/0220917 A1 | 9/2009 | Jensen ............... 433/202.1 |
| 2009/0239197 A1 | 9/2009 | Brajnovic ............... 433/174 |
| 2009/0239200 A1 | 9/2009 | Brajnovic et al. ............... 433/215 |
| 2009/0253097 A1 | 10/2009 | Brajnovic ............... 433/173 |
| 2009/0263764 A1 | 10/2009 | Berckmans, III et al. |
| 2009/0287332 A1 | 11/2009 | Adusumilli et al. ............... 700/98 |
| 2009/0298009 A1 | 12/2009 | Brajnovic ............... 433/75 |
| 2009/0298017 A1 | 12/2009 | Boerjes et al. ............... 433/214 |
| 2009/0317763 A1 | 12/2009 | Brajnovic ............... 433/174 |
| 2009/0325122 A1 | 12/2009 | Brajnovic et al. ............... 433/75 |
| 2010/0009314 A1 | 1/2010 | Tardieu et al. |
| 2010/0028827 A1 | 2/2010 | Andersson et al. ............... 433/75 |
| 2010/0038807 A1 | 2/2010 | Brodkin et al. ............... 264/17 |
| 2010/0075275 A1 | 3/2010 | Brajnovic ............... 433/75 |
| 2010/0092904 A1 | 4/2010 | Esposti et al. |
| 2010/0105008 A1 | 4/2010 | Powell et al. |
| 2010/0173260 A1 | 7/2010 | Sogo et al. ............... 433/75 |
| 2010/0280798 A1 | 11/2010 | Pattijn et al. |
| 2011/0008751 A1 | 1/2011 | Pettersson |
| 2011/0060558 A1 | 3/2011 | Pettersson |
| 2011/0129792 A1 | 6/2011 | Berckmans, III et al. |
| 2011/0183289 A1 | 7/2011 | Powell et al. |
| 2011/0191081 A1 | 8/2011 | Malfliet et al. |
| 2011/0244426 A1 | 10/2011 | Amber et al. |
| 2011/0269104 A1 | 11/2011 | Berckmans, III et al. |
| 2011/0275032 A1 | 11/2011 | Tardieu et al. |
| 2011/0306008 A1 | 12/2011 | Suttin et al. |
| 2011/0306009 A1 | 12/2011 | Suttin et al. |
| 2012/0010740 A1 | 1/2012 | Swaelens et al. |

FOREIGN PATENT DOCUMENTS

| | | |
|---|---|---|
| WO | WO 94/26200 | 11/1994 |
| WO | WO 99/32045 | 7/1999 |
| WO | WO 00/08415 | 2/2000 |
| WO | WO 01/58379 | 8/2001 |
| WO | WO 02/053055 | 7/2002 |
| WO | WO 03/024352 | 3/2003 |
| WO | WO 2004/030565 | 4/2004 |
| WO | WO 2004075771 A1 * | 9/2004 |
| WO | WO 2004/087000 | 10/2004 |
| WO | WO 2004/098435 | 11/2004 |
| WO | WO 2006/014130 | 2/2006 |
| WO | WO 2006/062459 | 6/2006 |
| WO | WO 2006/082198 | 8/2006 |

| WO | WO2007/005490 | 1/2007 | WO | WO 2008/057955 | 5/2008 |
| WO | WO 2007/033157 | 3/2007 | WO | WO2008/083857 | 7/2008 |
| WO | WO 2007/104842 | 9/2007 | WO | WO2009/146164 | 12/2009 |
| WO | WO 2007/129955 | 11/2007 | | | |

* cited by examiner

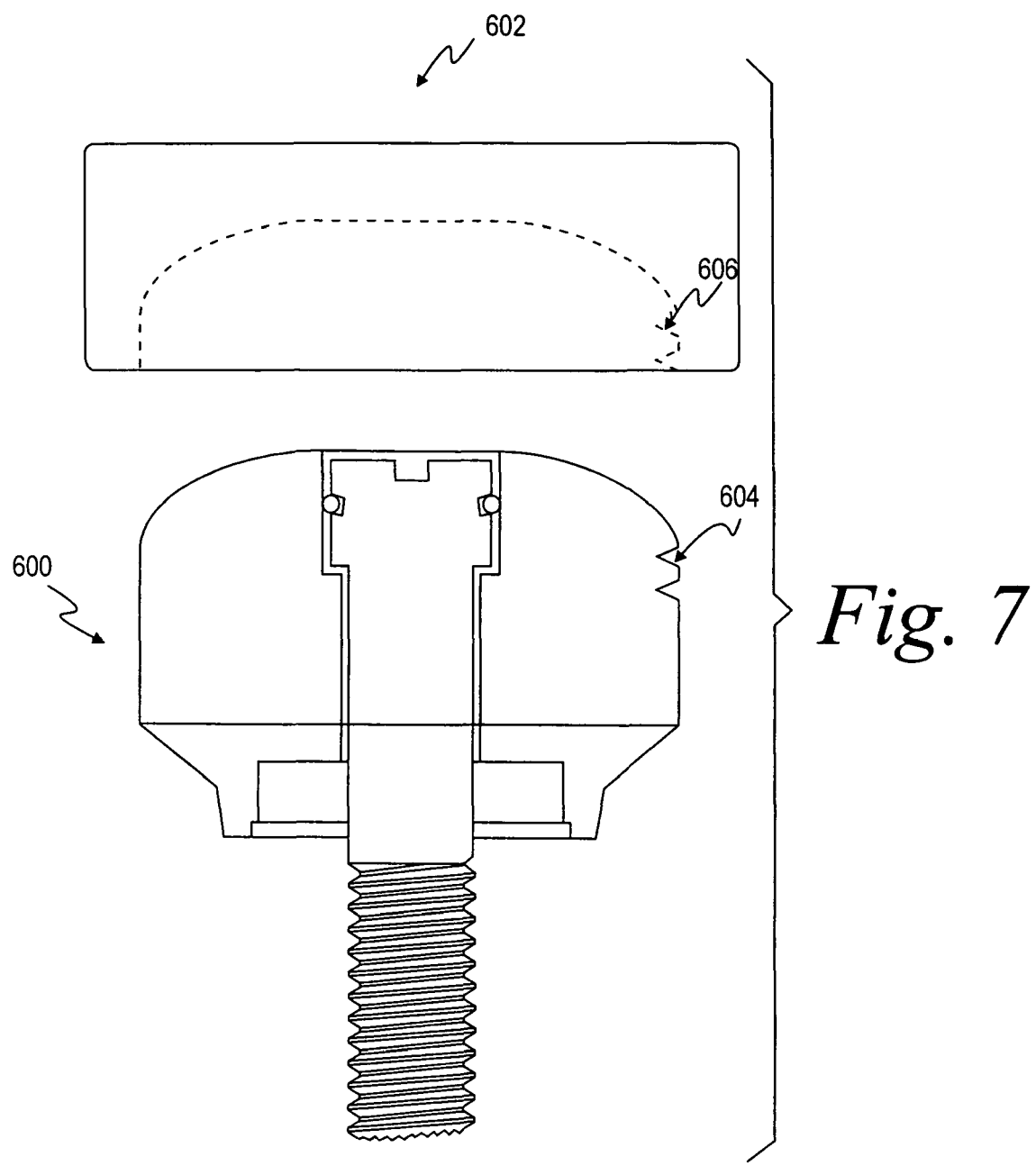

METHODS FOR PLACING AN IMPLANT ANALOG IN A PHYSICAL MODEL OF THE PATIENT'S MOUTH

RELATED APPLICATIONS

This application is a continuation-in-part of U.S. application Ser. No. 11/585,705 filed on Oct. 24, 2006 now U.S. Pat. No. 7,661,956 and entitled "Methods for Manufacturing Dental Implant Components," which claims the benefit of U.S. Provisional Patent Application No. 60/729,506 filed on Oct. 24, 2005 and entitled "Methods for Manufacturing Dental Implant Components. Both of these applications are hereby incorporated by reference in their entireties.

FIELD OF INVENTION

The present invention relates generally to dental implant systems. More particularly, the present invention relates to restoration components for dental implant systems and a computer model for developing an implant analog placement tool to eliminate the need for a surgical index.

BACKGROUND OF THE INVENTION

The dental restoration of a partially or wholly edentulous patient with artificial dentition is typically done in two stages. In the first stage, an incision is made through the gingiva to expose the underlying bone. An artificial tooth root, usually a dental implant, is placed in the jawbone for integration. The dental implant generally includes a threaded bore to receive a retaining screw holding mating components therein. During the first stage, the gum tissue overlying the implant is sutured and heals as the osseointegration process continues.

Once the osseointegration process is complete, the second stage is initiated. Here, the gum tissue is re-opened to expose the end of the dental implant. A healing component or healing abutment is fastened to the exposed end of the dental implant to allow the gum tissue to heal therearound. Preferably, the gum tissue heals such that the aperture that remains generally approximates the size and contour of the aperture that existed around the natural tooth that is being replaced. To accomplish this, the healing abutment attached to the exposed end of the dental implant has the same as the gingival portion of the natural tooth being replaced.

During the typical second stage of dental restoration, the healing abutment is removed and an impression coping is fitted onto the exposed end of the implant. This allows an impression of the specific region of the patient's mouth to be taken so that an artificial tooth is accurately constructed. Thus, in typical dental implant systems, the healing component and the impression coping are two physically separate components. Preferably, the impression coping has the same gingival dimensions as the healing component so that there is no gap between the impression coping and the wall of the gum tissue defining the aperture. Otherwise, a less than accurate impression of the condition of the patient's mouth is made. The impression coping may be a "pick-up" type impression coping or a "transfer" type impression coping, both known in the art. After these processes, a dental laboratory creates a prosthesis to be permanently secured to the dental implant from the impression that was made.

In addition to the method that uses the impression material and mold to manually develop a prosthesis, systems exist that utilize scanning technology to assist in generating a prosthesis. A scanning device is used in one of at least three different approaches. First, a scanning device can scan the region in the patient's mouth where the prosthesis is to be placed without the need to use impression materials or to construct a mold. Second, the impression material that is removed from the healing abutment and surrounding area is scanned. Third, a dentist or technician can scan the stone model of the dental region that was formed from the impression material and mold to produce the permanent components.

Three basic scanning techniques exist, laser scanning, photographic imaging and mechanical sensing. Each scanning technique is used or modified for any of the above-listed approaches (a scan of the stone model, a scan of the impression material, or a scan in the mouth without using impression material) to create the prosthesis. After scanning, a laboratory can create and manufacture the permanent crown or bridge, usually using a computer aided design ("CAD") package.

The utilization of a CAD program, as disclosed in U.S. Pat. No. 5,338,198, (Wu), whose disclosure is incorporated by reference herein, is one method of scanning a dental region to create a three dimensional model. Preferably, after the impression is made of the patient's mouth, the impression material or stone model is placed on a support table defining the X-Y plane. A scanning laser light probe is directed onto the model. The laser light probe emits a pulse of laser light that is reflected by the model. A detector receives light scattered from the impact of the beam with the impression to calculate a Z-axis measurement. The model and the beam are relatively translated within the X-Y plane to gather a plurality of contact points with known location in the X-Y coordinate plane. The locations of several contact points in the Z-plane are determined by detecting reflected light. Finally, correlating data of the X-Y coordinates and the Z-direction contact points creates a digital image. Once a pass is complete, the model may be tilted to raise one side of the mold relative to the opposite vertically away from the X-Y plane. Subsequent to the model's second scan, the model may be further rotated to allow for a more accurate reading of the model. After all scans are complete, the data may be fed into a CAD system for manipulation of this electronic data by known means.

Photographic imaging can also used to scan impression material, a stone model or to scan directly in the mouth. For example, one system takes photographs at multiple angles in one exposure to scan a dental region, create a model and manufacture a prosthetic tooth. As disclosed in U.S. Pat. No. 5,851,115, (Carlsson), whose disclosure is incorporated by reference herein, this process is generally initiated with the process of taking a stereophotograph with a camera from approximately 50 to 150 mm away from the patient's mouth. The stereophotograph can involve a photograph of a patient's mouth already prepared with implantation devices. Correct spatial positioning of the dental implants is obtained by marking the implant in several locations. The resulting photograph presents multiple images of the same object. The images on the photographs are scanned with a reading device that digitizes the photographs to produce a digital image of the dental region. The data from the scanner is electronically transmitted to a graphical imaging program that creates a model that is displayed to the user. After identification of the shape, position and other details of the model, the ultimate step is the transmission of the data to a computer for manufacturing.

A third scanning measure uses mechanical sensing. A mechanical contour sensing device, as disclosed in U.S. Pat. No. 5,652,709 (Andersson), whose disclosure is incorporated by reference herein, is another method used to read a dental model and produce a prosthetic tooth. The impression model is secured to a table that may rotate about its longitudinal axis as well as translate along the same axis with variable speeds. A mechanical sensing unit is placed in contact with the model at a known angle and the sensing equipment is held firmly against the surface of the model by a spring. When the model is rotated and translated, the sensing equipment can measure the changes in the contour and create an electronic representation of the data. A computer then processes the electronic representation and the data from the scanning device to create a data array. The computer then compresses the data for storage and/or transmission to the milling equipment.

When the stone model of the patient's mouth is created for use in the scanning process, or in other prior techniques, a second stone model of the patient's mouth is also typically used to develop a final prosthesis for use in the patient. The prosthesis is typically developed on the second stone model. A surgical index is used to position the implant analog within the second stone model so that the dental laboratory may know the exact position of the implant when making the prosthesis. The surgical index is typically a mold of the patient's teeth directly adjacent to the implant site that relies upon the position of the adjacent teeth to dictate the location and orientation of the implant analog within the stone model. Unfortunately, the surgical index is an additional step in the process for the clinician that requires additional components. A need exists for a device and method of placing the implant analog within the stone model without using a conventional surgical index.

SUMMARY OF THE INVENTION

According to one aspect of the present invention, a method of affixing an implant analog in a physical model of a patient's mouth for use in creating a custom abutment comprises determining, in a three-dimensional virtual model of the patient's mouth, the location of the implant analog to be placed in the physical model. The method further includes developing implant-analog positional information based on the location of the implant analog in the three-dimensional virtual model and developing an emergence profile contour information to provide for a contour of an opening to be made in the physical model leading to the implant analog. The contour is preferably tapered downwardly toward the implant analog. The method further includes transferring to a robot (i) the implant-analog positional information, and (ii) the emergence profile contour information, using the robot to modify the physical model by creating an opening in the physical model having a tapering contour, and using the robot to affix the implant analog within the opening of the physical model.

According to another aspect of the present invention, a method of positioning an implant analog in a physical model of a patient's mouth for use in creating a custom abutment comprises scanning the physical model to develop scan data of the physical model, transferring the scan data to a CAD program, and creating a three-dimensional model of at least a portion of the physical model on the CAD program using the scan data. The method further includes determining, in the three-dimensional model, the location of the implant analog to be placed in the physical model, developing implant-analog positional information based on the location of the implant analog in the three-dimensional model, and developing an emergence profile contour information to provide for a contour of an opening to be made in the physical model leading to the implant analog. The method further includes transferring to a robot (i) the implant-analog positional information and (ii) the emergence profile contour information, and, by use of at least one tool associated with the robot, modifying the physical model by creating the opening. The opening has an emergence profile corresponding to the emergence-profile contour information. The method may further include, by use of the robot, fixing the implant analog within the opening of the physical model in accordance to the implant-analog positional information.

According to yet another process of the present invention, a method of positioning an implant analog in a physical model of a patient's mouth for use in creating a custom abutment, comprises scanning the physical model to develop scan data of the physical model, transferring the scan data to a CAD program, and creating a three-dimensional model of at least a portion of the physical model on the CAD program using the scan data. The method further includes determining, in the three-dimensional model, the location of the implant analog to be placed in the physical model, and using a robot to place an implant analog within the physical model in accordance with information from the three-dimensional model.

According to yet a further aspect of the present invention, a method of performing guided surgery in a patient's mouth, comprises taking a CT-scan of the patient's mouth to develop CT-scan data, and developing, on a 3D-computer model, a surgical plan based on the CT-scan data. The surgical plan includes at least one virtual implant. The virtual implant has virtual-implant location data and virtual implant orientation data corresponding to a non-rotational feature on the virtual implant. Based on the surgical plan, the method further may further include manufacturing a surgical guide to be placed in the patient's mouth for installing an implant in the patient's mouth at substantially the same location and orientation as the virtual implant on the 3D-computer model, and manufacturing a physical model of the patient's mouth having an implant analog at substantially the same location and orientation as the virtual implant on the 3D-computer model. The method further includes developing a custom abutment on the physical mode, performing surgery to place the implant in the patient's mouth as physically guided by the surgical guide in accordance with the surgical plan, and installing the custom abutment on the implant.

BRIEF DESCRIPTION OF THE DRAWINGS

FIG. 1b is a longitudinal cross-sectional view of the healing abutment shown in FIG. 1a;

FIG. 2b is a longitudinal cross-sectional view of the healing abutment shown in FIG. 2a;

FIG. 3b is a longitudinal cross-sectional view of the healing abutment shown in FIG. 3a.

FIG. 4b is a longitudinal cross-sectional view of the healing abutment shown in FIG. 4a;

FIG. 5b is a longitudinal cross-sectional view of the healing abutment shown in FIG. 5a;

FIG. 6b is a longitudinal cross-sectional view of the healing abutment shown in FIG. 6a;

FIG. 7 is an exploded view of another embodiment of the present application;

Figure 1A:
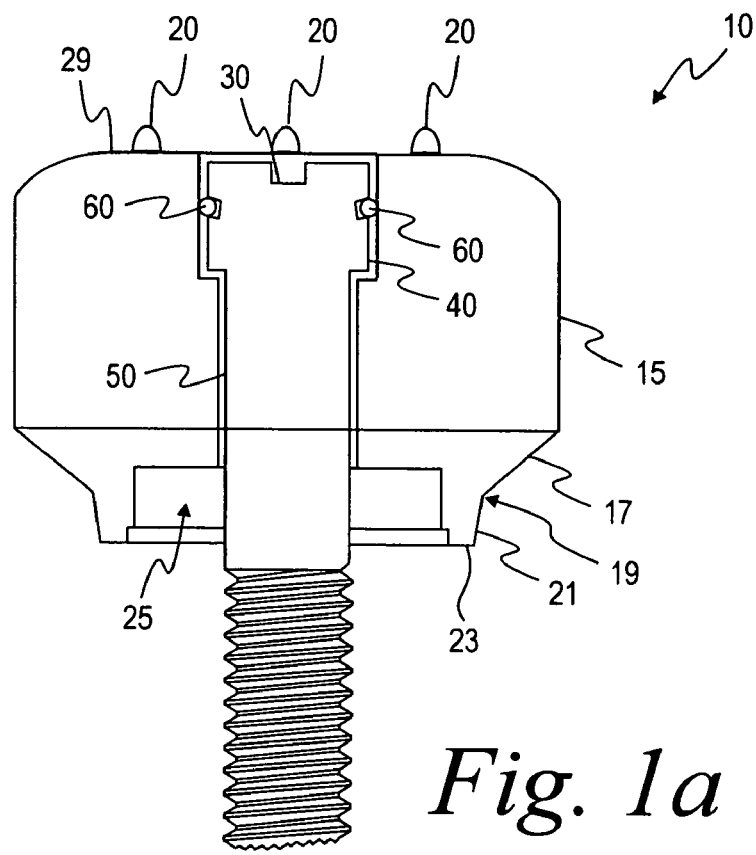
FIG. 1a is a top view of a healing abutment.

While the invention is susceptible to various modifications and alternative forms, specific embodiments thereof have been shown by way of example in the drawings and will herein be described in detail. It should be understood, however, that it is not intended to limit the invention to the particular forms disclosed but, on the contrary, the intention is to cover all modifications, equivalents, and alternatives falling within the spirit and scope of the invention as defined by the appended claims.

DESCRIPTION OF ILLUSTRATIVE EMBODIMENTS

Figure 1B:
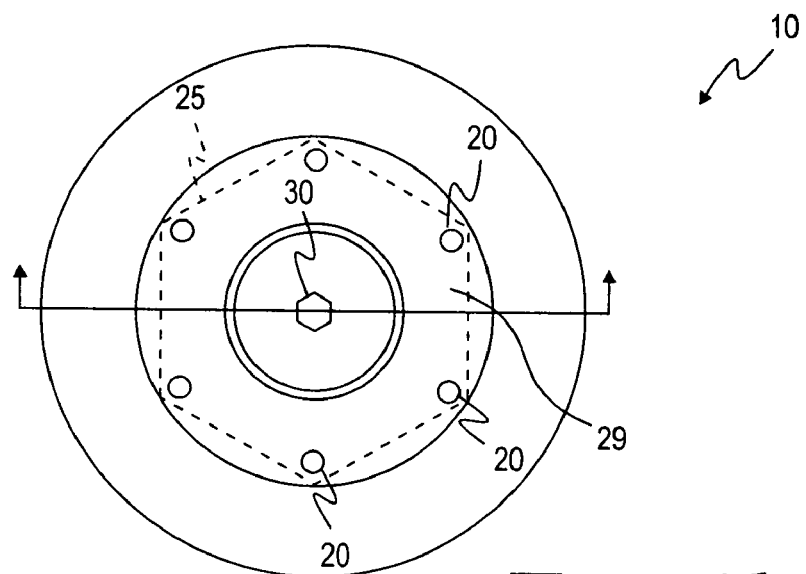

As shown in FIGS. 1a and 1b, the healing abutment 10 of one embodiment of the present invention has a main body 15 with a generally circular cross-sectional shape, a first tapered section 17, a boundary 19, a second tapered section 21, an end surface 23, a hex socket 25 and dimensions that are generally suitable for replicating the emergence profile of a natural tooth. The first tapered section 17 extends downwardly from the main body 15 of the abutment 10 having a diameter at a boundary 19 that is generally larger than the implant (not shown). The boundary 19 separates the first tapered section 17 from the second tapered section 21 that terminates in the end surface 23. The second tapered section 21 is at an angle with the central axis of the implant that is generally in the range from about 5 degrees to about 15 degrees, with 10 degrees being preferable. Alternatively, the second tapered section 21 may be omitted such that the first tapered section 17 tapers directly to the diameter of the end surface 23 of the implant. In a further embodiment, the first tapered section 17 may merge smoothly into the second tapered section 21, without the distinct boundary 19 separating the two tapered sections 17 and 21. The hexagonal orientation socket or hex 25 is for mating with a hexagonal boss on the implant. The end surface 23 has generally the same diameter as the seating surface of the implant.

FIG. 1b discloses the top view of the same healing abutment 10 shown in FIG. 1a. As shown in FIGS. 1a and 1b, the healing abutment 10 has positive information markers 20 protruding from a top surface 29 of the healing abutment 10. Each of the six positive information markers 20 is disposed such that it aligns with the six corners of the underlying hex 25. It is also contemplated in accordance with the present invention that the six information markers 20 may also correspond to the height of the healing abutment. For example, two information markers might correspond to a 2 mm tall healing abutment and four information markers might correspond to a healing abutment that is 4 mm tall. In these embodiments, the two or four information markers would still be at the corners of the underlying hex 25 so that the relative position of the hex is known.

Figure 1C:
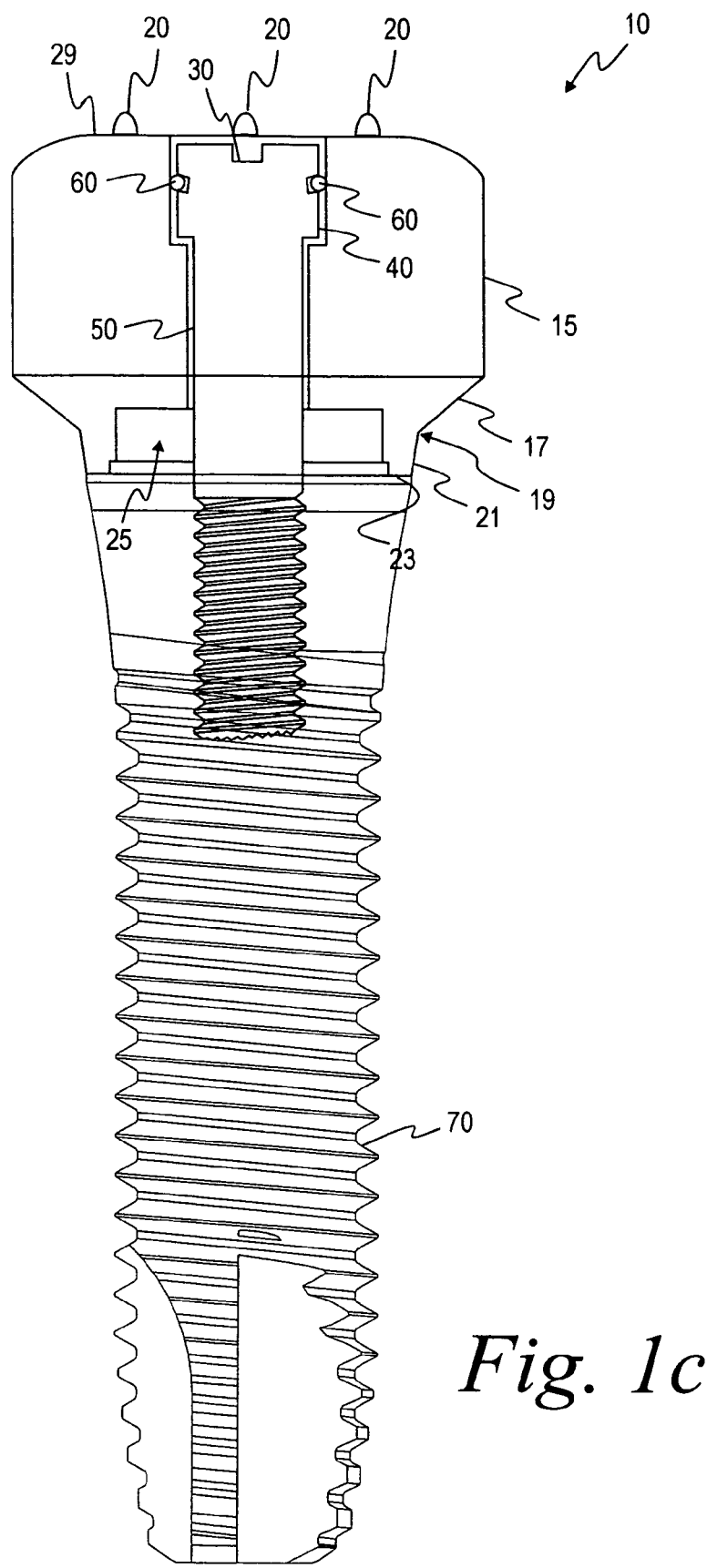
FIG. 1c is the healing abutment shown in FIG. 1b attached to an implant.

A socket 30 on the exposed surface of a head portion 40 of an attaching bolt 50 is shaped to accept a wrench (not shown) for turning the attaching bolt 50 into the threaded bore of an implant 70, as shown in FIG. 1c. It is contemplated in accordance with the present invention that each of the healing abutments described herein and shown in the figures can be secured to an implant by means of an attaching bolt, as is known in the art. An O-ring 60 carried on the head portion 40 of the attaching bolt 50 fills an annular gap left between the head and the entrance section near the outermost (widest) opening in the entrance section.

Figure 2A:
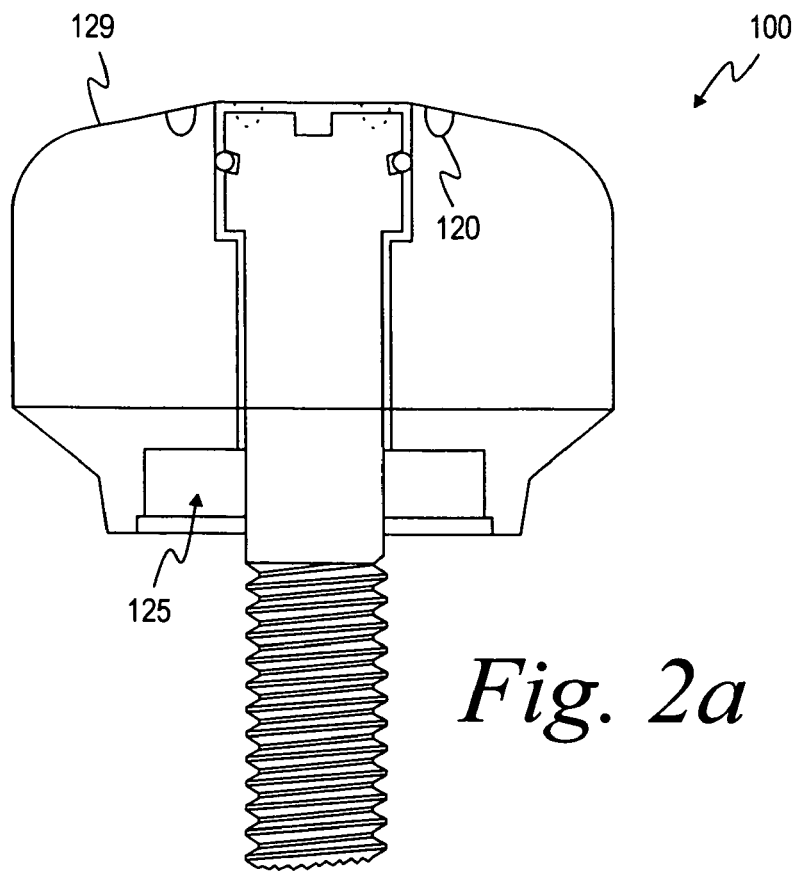
FIG. 2a is a top view of another embodiment of a healing abutment.
Figure 2B:
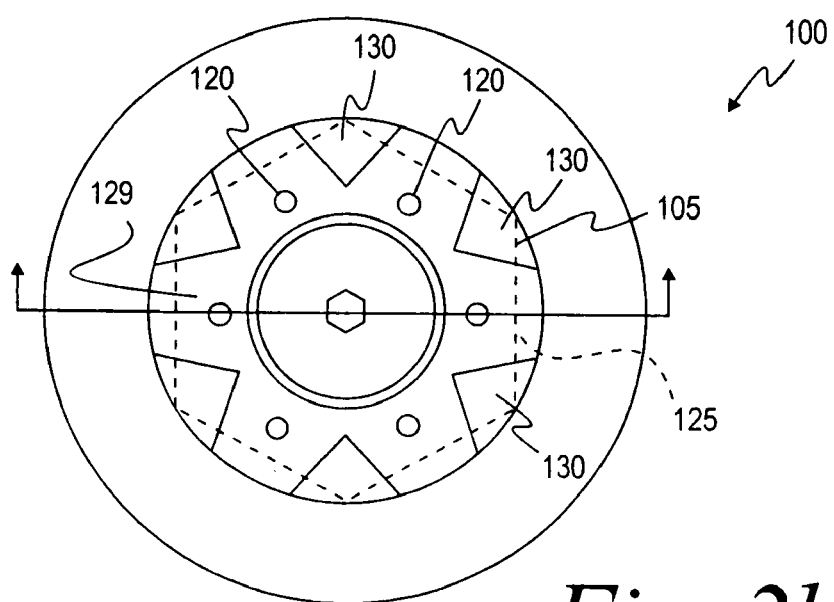

A healing abutment 100 of FIG. 2a comprises many of the same features as the healing abutment 10 shown in FIG. 1a. Dashed lines 125 in FIG. 2b correspond to the underlying hex 125 of the healing abutment 100 in FIG. 2a. A top surface 129 includes negative information markers (recesses) 120 that are displayed in FIG. 2a as dimples extending below the top surface 129 of the healing abutment 100. The top surface 129 of the healing abutment 100 also possesses six notches 130 that are machined into the corners. The top surface 129 is generally flat and merges into a rounded shape at the periphery of the healing abutment 100.

The notches 130 are used, for example, to determine the identification of the underlying implant hex position 125 or the height of the healing abutment or the diameter of the healing abutment. This embodiment is not limited to comprising six notches in the top surface 129 of the healing abutment 100. It is also contemplated that one embodiment of the present invention may possess four notches or even two notches for indicative purposes. Furthermore, it is contemplated that the information marker and notch approach could be combined or modified to provide information regarding the underlying implant seating surface diameter and implant hex angulation.

Figure 3A:
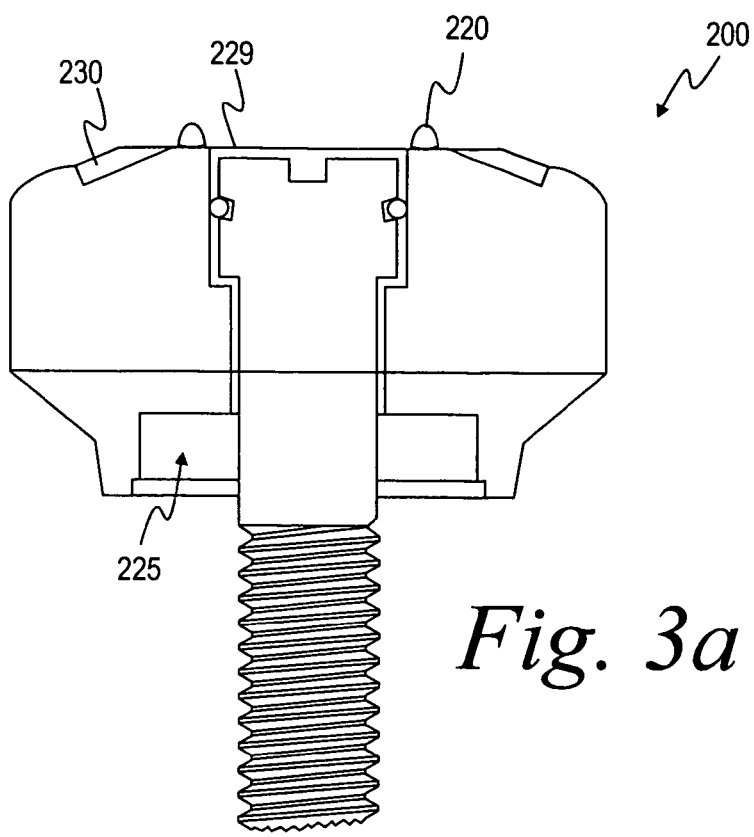
FIG. 3a is a top view of yet another embodiment of a healing abutment.
Figure 3B:
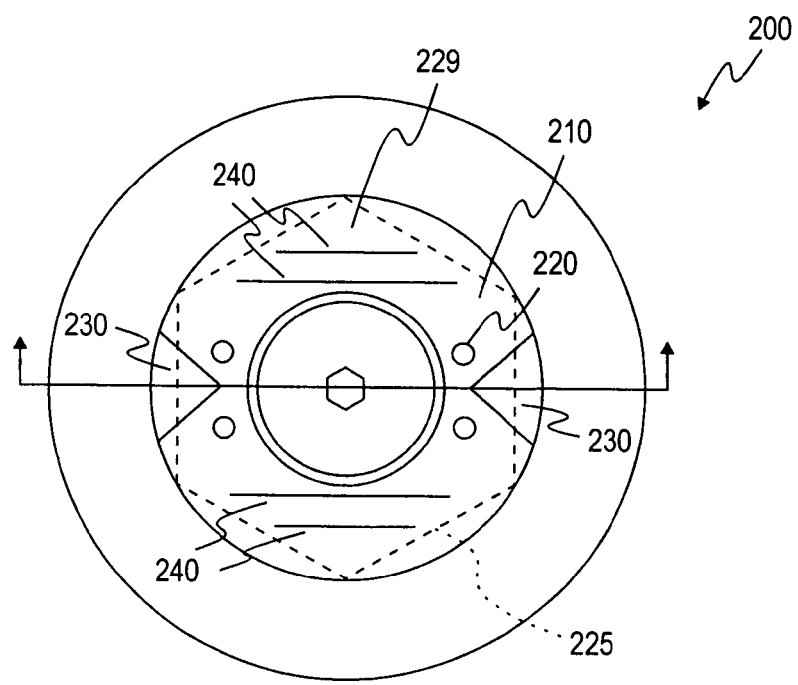

In another embodiment of the present invention, a healing abutment 200 shown in FIGS. 3a and 3b displays four positive information markers 220 shown to, for example, indicate a 4 mm tall healing abutment 200. It is contemplated that the number of information markers 220 could decrease or increase depending on the height of the healing abutment 200 or another variable that the information markers have been designated to correspond. The positive information markers 220 also define a corresponding one of the six flat surfaces of an underlying hex 225. Furthermore, dashed lines 225 in FIG. 3b correspond directly to the underlying hex 225.

Figure 4A:
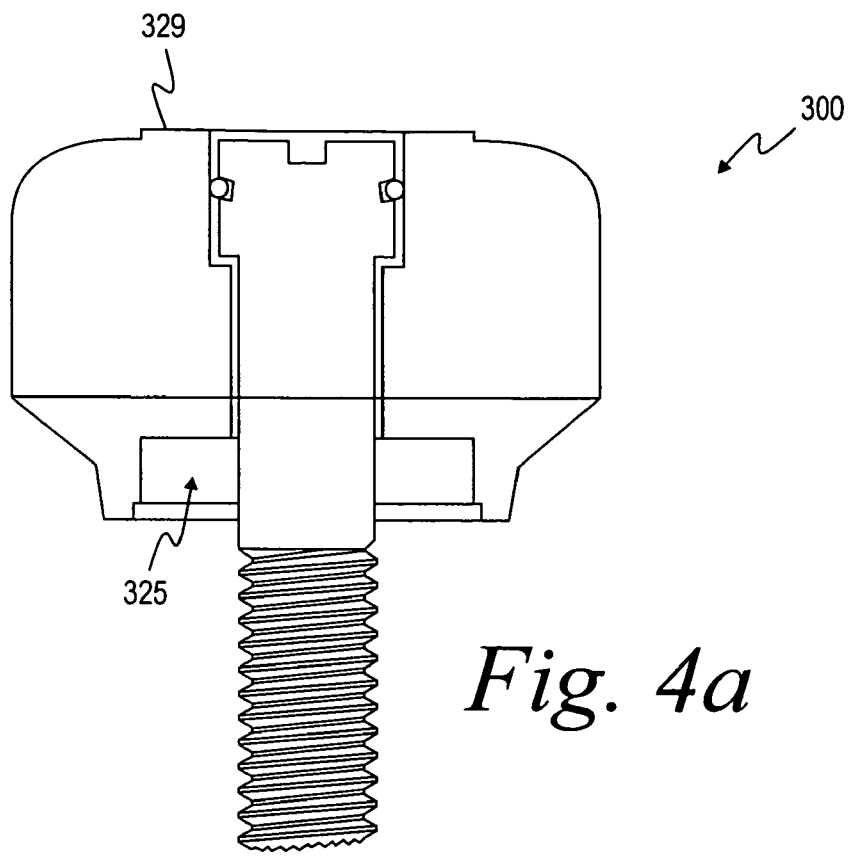
FIG. 4a is a top view of a further embodiment of the healing abutment.
Figure 4B:
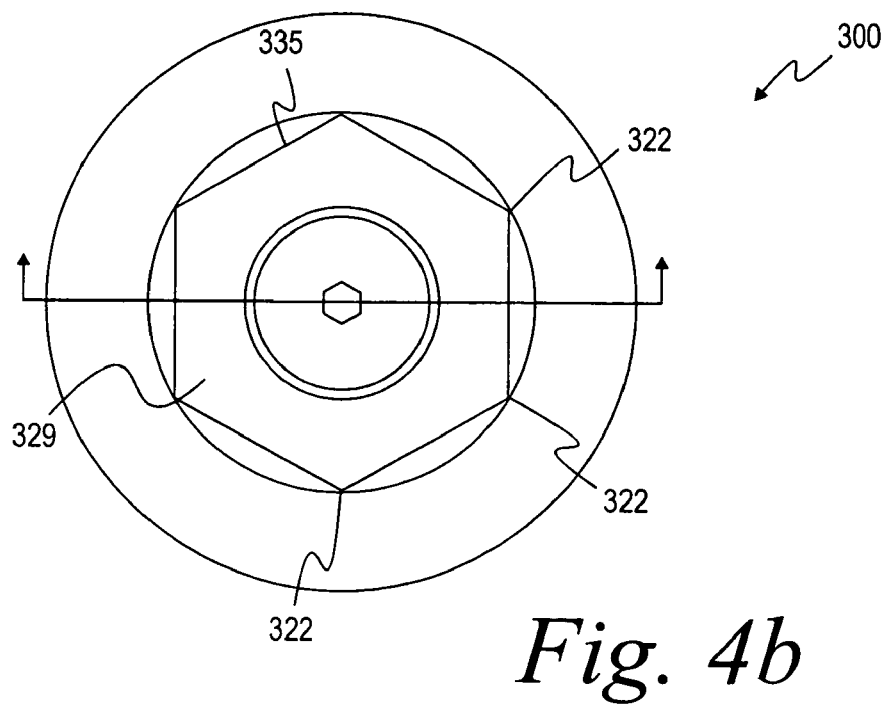

Two notches 230 have also been etched or machined onto a top surface 229 of the healing abutment of FIG. 3b. These notches may indicate the diameter of the implant's seating surface. Lines 240 are scribed on the top surface 229 of the healing abutment 200. The lines 240 are used to provide positioning or other information to the dentist or laboratory. Here, the lines 240 indicate the diameter of the healing abutment (e.g., 4 mm). In summary, the number of the positive information markers 220 indicates the height of the healing abutment 200. The position of the positive information markers 220 indicates the orientation of the hex 225 that is the orientation of the hexagonal boss on the implant. The notches 230 indicate the diameter of the seating surface of the implant. The lines 240 indicate the diameter of the healing abutment 200. generally In yet another embodiment of the present invention, a top surface 329 of the healing abutment 300 of FIGS. 4a and 4b comprises an etched or machined hex 335. Corners 322 of the etched hex 335 correspond directly to the position of the corners of an underlying hex 325 shown in FIG. 4a. It is contemplated in accordance with one embodiment of the present invention that further information markers may be added to the healing abutment for the dentist or laboratory to ascertain different heights or diameters.

Figure 5A:
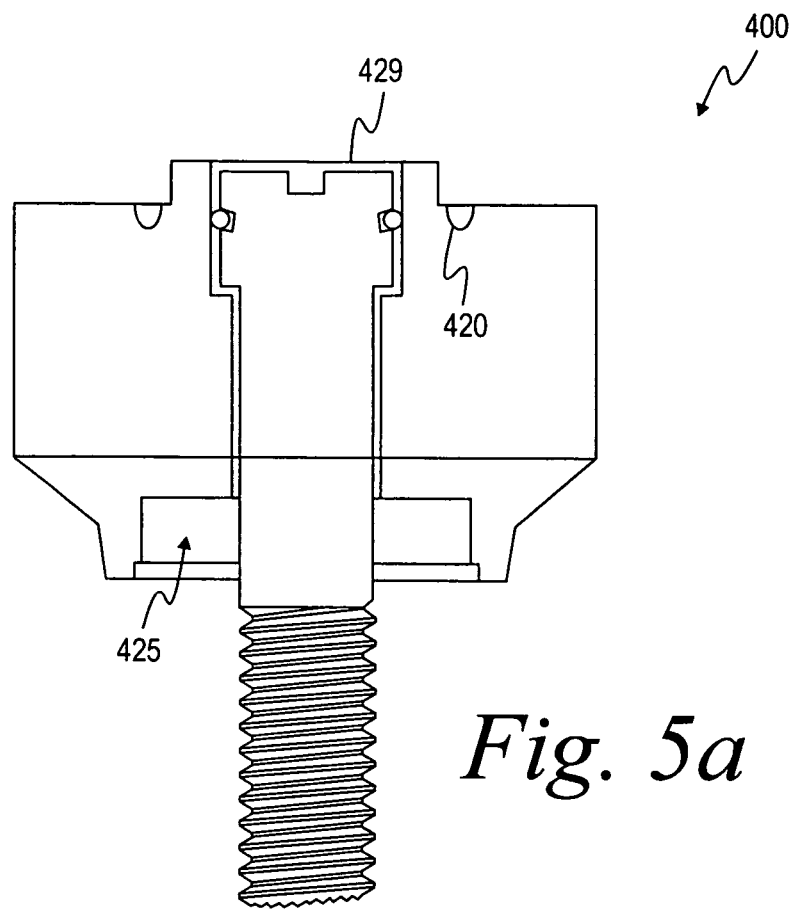
FIG. 5a is a top view of another embodiment of a healing abutment.
Figure 5B:
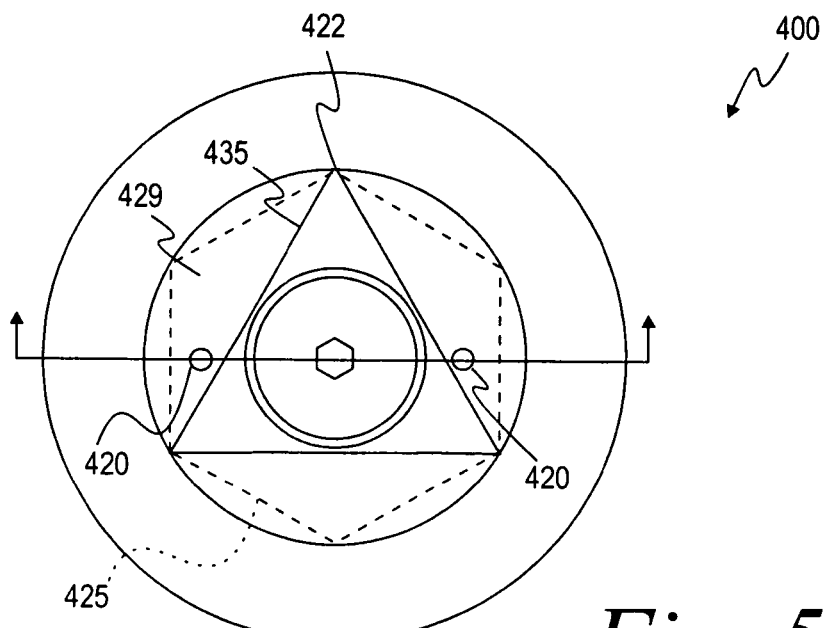

A top surface 429 of a healing abutment 400 shown in FIGS. 5a and 5b contains an etched or machined triangle 435. Dashed lines 425 in FIG. 5b indicate the location of an underlying hex 425. Corners 422 of the etched triangle 435 correspond to three of the six corners of the underlying hex 425. Furthermore, two negative information markers 420 are shown in FIG. 5b. As above, it is contemplated in accordance with the present invention that fewer than six information markers may exist to account for differing heights or diameters of the healing abutments.

Figure 6A:
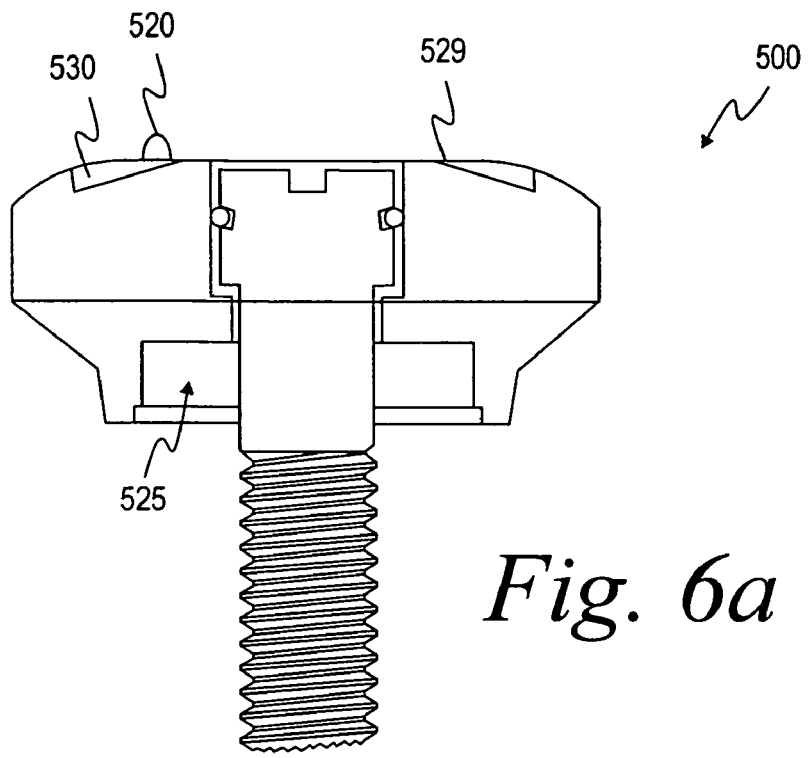
FIG. 6a is a top view of another embodiment of a healing abutment.
Figure 6B:
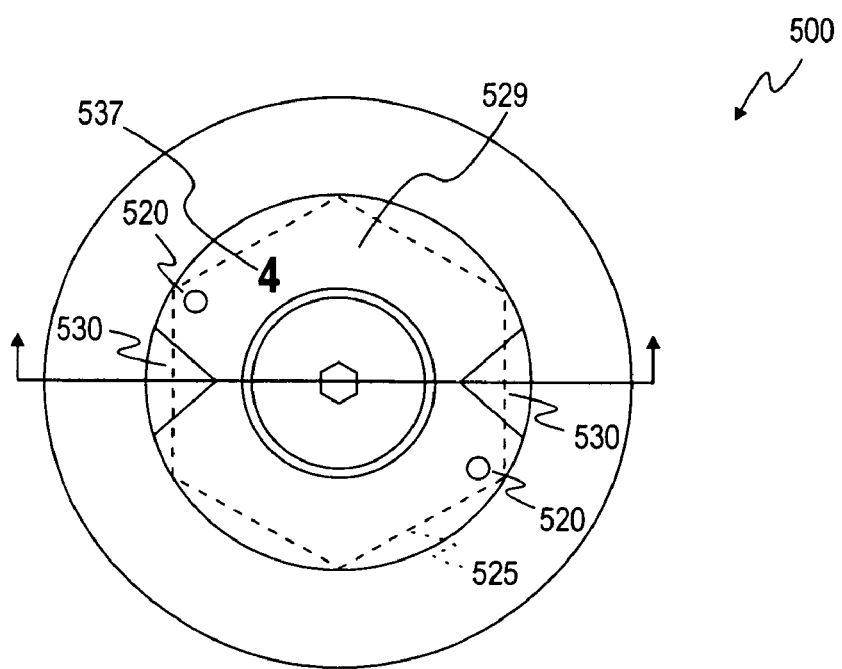

Another embodiment of the present invention is shown in FIGS. 6a and 6b. The healing abutment 500 displayed in FIGS. 6a and 6b is a shorter version of the healing abutment 10 shown in FIGS. 1a and 1b. Two positive information markers 520 are shown in FIG. 6b to identify the height of the healing abutment 500. Dashed lines 525 of the healing abutment 500 correspond with the location and orientation of the underlying hex 525. Two notches 530 are also shown in a top surface 529 of this embodiment of the present invention to show the orientation of two of the underlying flats of the underlying hex 525. A numeral "4" at 537 is located on the top surface 529 of the healing abutment 500 to indicate, for example, the diameter of the healing abutment 500. As shown, the numeral "4" at 537 corresponds to a healing abutment 500 with a diameter of 4 mm. It is contemplated in accordance with the present invention that other numerals could be placed on the top surface 529 of the healing abutment 500 to indicate other healing abutment diameters. Further, it is also contemplated that the numeral could represent the height of the healing abutment or the diameter of the underlying implant.

During the second stage of the prosthetic implementation process and after a healing abutment with the information markers has been placed, an impression of the mouth is made with only the healing abutments as described herein and without the use of an impression coping. A model of the impression is poured with, for example, die stone. Since the information markers are disposed on the top and/or side of the healing abutment, the laboratory has all necessary information to define the gingival aperture, the implant size and the orientation of the underlying hex. This enables the laboratory to quickly prepare the permanent components. The system of the present invention also allows the maintenance of the soft-tissue surrounding the healing abutment where in prior systems the soft tissue would close once the healing abutment was removed. The system spares the patient from the pain of removing the healing abutment.

Figure 8:
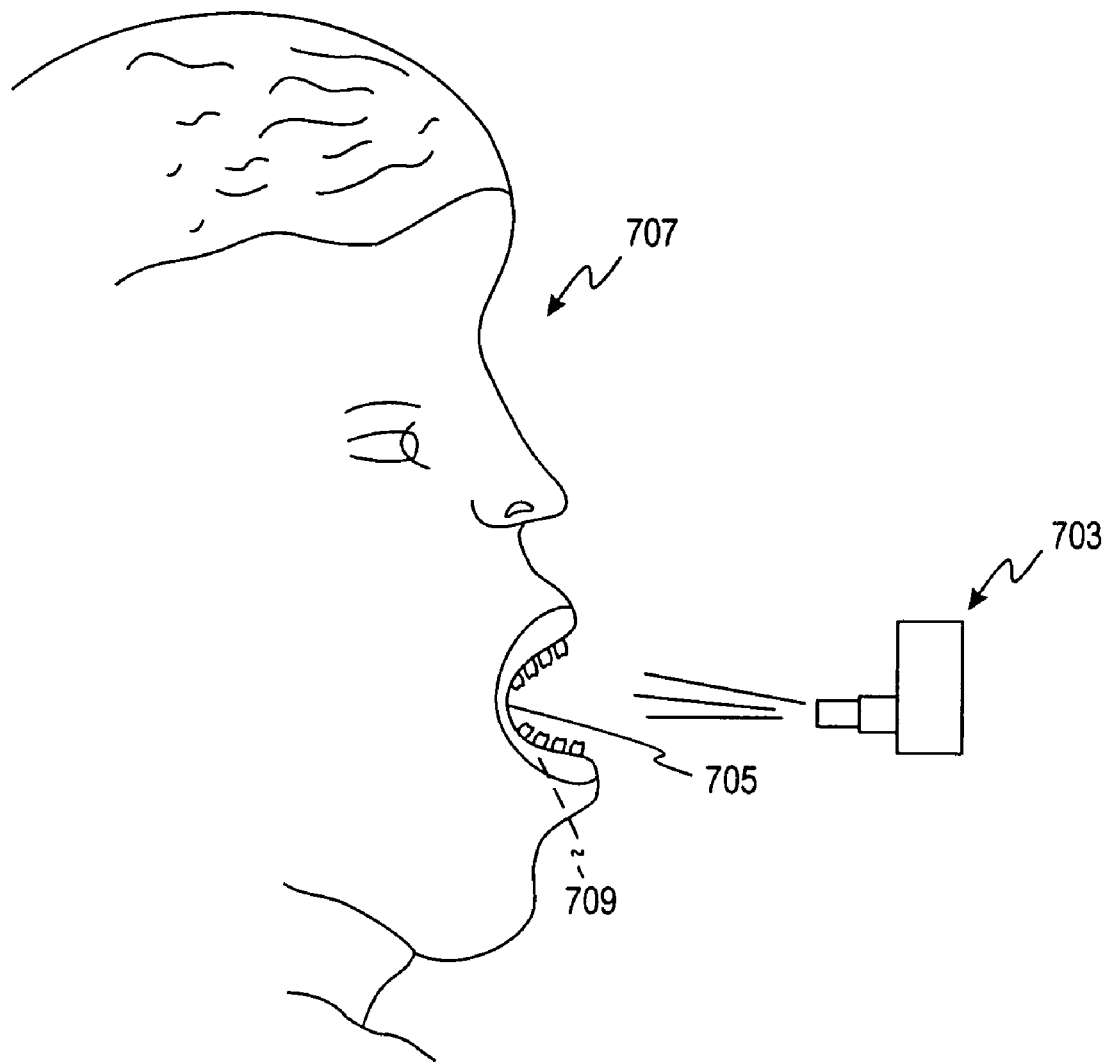
FIG. 8 is a side view of a method for stereophotographic imaging.

To create a permanent prosthesis, the dental region is scanned, as described above, from a stone model, from the impression material, or directly in the mouth using a laser scanning technique, a photographic scanning technique or a mechanical sensing technique. FIG. 8 shows stereophotographic imaging, one method used for scanning. Stereophotography with a camera 703 is performed directly on the mouth cavity 705 of the patient 707. A clinician can photograph implants and other components that have been placed into or adjacent the patient's jawbone 709.

The scanned information is then transferred into a graphical imaging program for analysis. The graphical imaging software program, due to the information markers on the surface of the healing abutment, can perform a wide variety of functions. The graphical imaging program can scan an opposing cast in order to develop an opposing occlusal scheme and relate this information back to the primary model. This feature is extremely important because many clinical patients have implants in both maxillary and mandibular locations.

The graphical imaging software program is capable of generating a three-dimensional image of the emergence profile contours used on the healing abutment. If the implant is not placed in the desired esthetic location, the software program relocates the position of the restoration emergence through the soft tissue. The graphical imaging software program is also able to accurately relate the gingival margin for all mold, model, implant and abutment dimensions. The software creates a transparent tooth outline for superimposition within the edentulous site. The occlusal outline of the "ghost" tooth should, if possible, be accurate and based on the scanned opposing occlusal dimensions. It is contemplated in accordance with the present invention that an occlusal outline is created by scanning a wax-up in order to maintain a proper plane of occlusion and healing abutment height.

The software program subtracts a given dimension from the mesial, distal, buccal, lingual, and occlusal areas of the superimposed tooth dimension. This allows for an even reduction of the healing abutment during fabrication to allow for proper thickness of the overlying materials (e.g., gold, porcelain, targis, etc.). The graphical imaging software program also incorporates angulation measurements into the custom abutment and subsequently calculates the dimensions of the prosthesis that are checked and modified, if necessary, by a laboratory technician. Each of the features is analyzed and determined from the different information markers that exist on the healing abutments of the present invention.

The final dimensional information determined by the graphical imaging computer program is transferred from the computer to a milling machine (e.g., a 5-axis milling machine) to fabricate the custom abutment. It is contemplated in accordance with the present invention that the custom abutment can be fashioned from gold or titanium or other similar metals or composites. A custom milled coping can then be fabricated. It is contemplated in accordance with the present invention that the custom milled coping can be formed from titanium, plastic, gold, ceramic, or other similar metals and composites.

FIG. 7 shows the exploded view of another embodiment of the present invention. A cap 602 is placed on a healing abutment 600 and later removed during the process of taking the impression of the healing implant and surrounding features of the patient's mouth. It is contemplated in accordance with the present invention that the cap 602 could be formed from plastic or metal or a composite material. As shown in FIG. 7, notches 604 are formed in the side(s) of the healing abutment 600. These notches correspond to notches 606 that have been preformed in the cap 602. When the cap 602 is placed onto the healing abutment 600, the cap only fits snugly and properly if the number of notches 606 in the cap 602 corresponds exactly to the number of notches 604 in the side wall(s) of the healing abutment. It is contemplated in accordance with the present invention that there could be many less or more notches than is depicted in FIG. 7. These notches correspond to information parameters such as healing abutment height, healing abutment and/or implant diameter and other parameters as listed above.

Specifically, after the healing abutment has been secured to the implant, the cap 602 is securely placed over the top of the healing abutment 600. The impression material is then placed over the top of the cap 602. The impression is then either scanned in the patient's mouth or the impression material (with the cap 602) is then scanned and the process continues as described above.

Figures 9A, 9B, 9C, 9D:
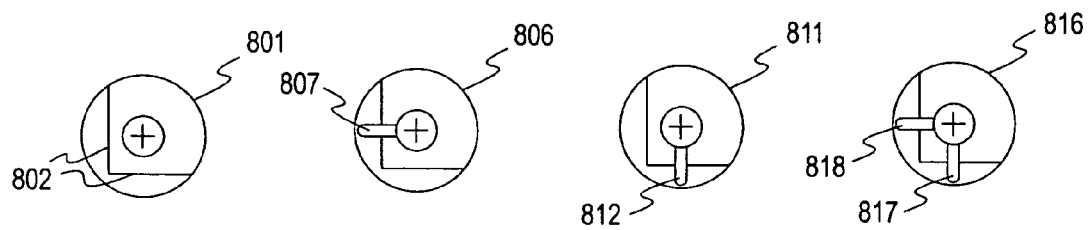
FIGS. 9a-9p are top views of a plurality of healing abutments having a binary-type system of information markers.
Figures 9E, 9F, 9G, 9H:
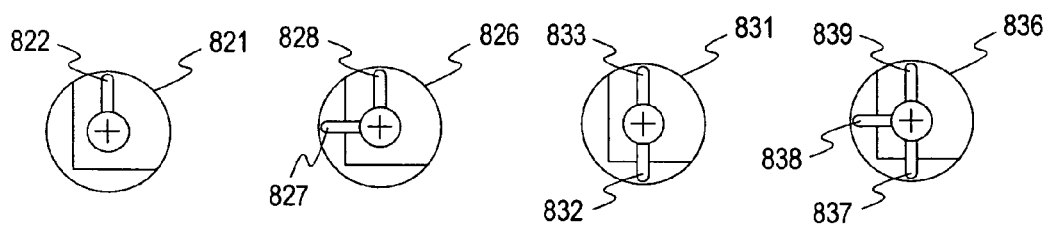
FIG. 9q is a top view of a healing abutment having a bar code information marker.
Figures 9I, 9J, 9K, 9L:
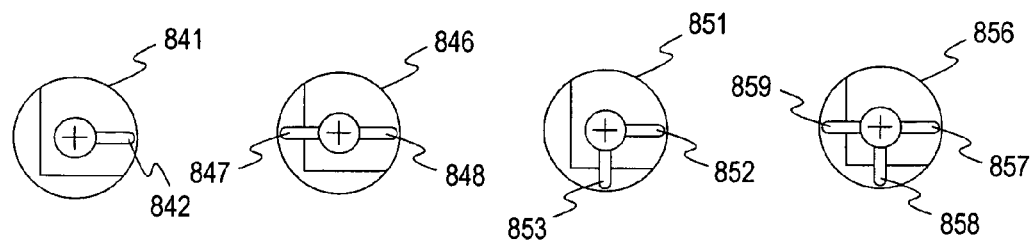
Figures 9M, 9N, 9O, 9P:
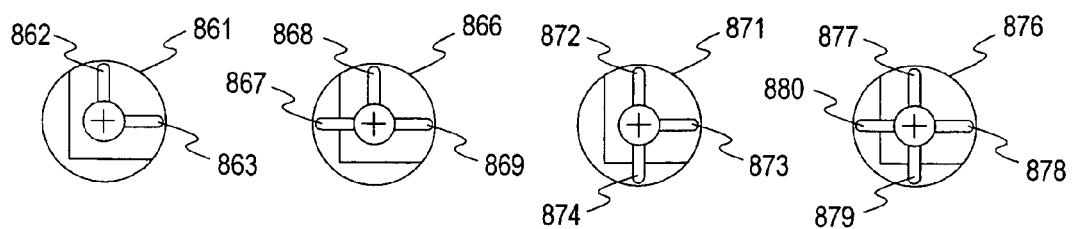

FIGS. 9a-9p depict yet another embodiment of the present invention. Specifically, FIGS. 9a-9p show the top view of a plurality of healing abutments, each of which has four marking locations on the top surface of the healing abutment. For each healing abutment, a marker is either present or absent in each of the four marking locations, and the presence or absence can be interpreted either visually or by a scanning device. As explained below in detail, the markers in the marking locations permit identification of healing abutment characteristics, such as dimensions of the healing abutment.

In FIGS. 9a-9p, the four rows correspond to four different healing abutment heights (e.g., 3 mm, 4 mm, 6 mm, and 8 mm). The four columns of the coding key correspond to four different diameters of the healing abutment seating surfaces (e.g., 3.4 mm, 4.1 mm, 5.0 mm, and 6.0 mm). Accordingly, sixteen unique healing abutments are present.

The top surface of each of the healing abutments has from zero to four information markers located in the four marking locations. As shown in FIGS. 9a-9p, the marking locations extend radially from a central region of the healing abutment to the outer region of the top surface of the healing abutments (i.e., at locations of 12 o'clock, 3 o'clock, 6 o'clock, and 9 o'clock).

As is well known, a binary-coded system exists as an array of digits, where the digits are either "1" or "0" that represent two states, respectively, ON and OFF. For each marking location, the presence of a marker ("ON") is a 1 and the absence of a marker ("OFF") is a 0. By grouping sets of 1's and 0's together, information about each healing abutment is known. In the illustrative embodiment, the determination of the sets of 1's and 0's derived from the information markers (e.g., via visual inspection, scanning in the mouth, scanning of the impression, or scanning of the model created by the impression) provide information on the height of the healing abutment and the diameter of the seating surface of the attached implant.

The information markers shown in FIGS. 9a-9p are in the form of grooves having rounded cross-sections. The present invention, however, provides that the cross-section of these grooves can be rectangular, triangular, or various other shapes. When an impression is created from the healing abutment, the grooved marking locations produce a protruding "mound"-like element in the impression. This impression is then scanned so that identifying features regarding the healing abutment can be obtained. Alternatively, a model of the patient's mouth is created from the impression such that the markings are again grooves in the model that substantially replicate the grooves in the healing abutments. Of course, the markers could also be protrusions instead of grooves. Further, if the unique characteristics of the healing abutment are to be identified through scanning in the mouth or simply visual scanning by the clinician, then markers not producing features in impression material, such as etched or laser marking, may also be used.

Turning now to the specifics of each healing abutment, FIG. 9a illustrates a top view of a healing abutment 801 that includes orientation pick-ups 802. These orientation pick-ups 802 are also present in each of the healing abutments shown in FIGS. 9b-9p. The most counterclockwise of the orientation pick-ups 802 (i.e., the horizontal pick-up at the lower region of FIGS. 9a-9p) is always parallel to one flat of the implant hex, as viewed from the top of the healing abutment. As shown, the orientation pick-ups 802 are a pair of bevels on the sides of the healing abutments in FIGS. 9a-9p. Alternatively, the orientation pick-ups 802 can be grooves or protruding ridges, as well.

The orientation pick-ups 802 serve a second function in that they dictate which of the four marking locations is the first marking location. The other three marking locations are then read in clockwise order, proceeding from the most counterclockwise pick-up 802 to the other three marking locations on the top surface of the healing abutment. In other words, as illustrated in FIGS. 9a-9p, the information marker at 6 o'clock is the first digit in the binary code, the information marker at 9 o'clock is the second digit in the binary code, the information marker at 12 o'clock is the third digit in the binary code, and the information marker at 3 o'clock is the fourth digit in the binary code. In summary, the position of the orientation pick-ups 802 allows for the determination of the position of one of the hex flats of the healing abutment (and, likewise, one of the hex flats on the implant), and also the starting point to check for the presence or absence of information markers.

The results of a scan (computer or visual) of the four information markers on the healing abutment 801 produce no information markers at the four marking locations on the healing abutment 801 of FIG. 9a. Thus, the binary code for the healing abutment 801 is 0000, indicating that no grooved marker is present in any of the four predetermined positions. Since the coding key is preset (on a chart or in computer software), the binary code 0000 indicates that the healing abutment 801 is a resident of first row and first column of the matrix depicted by FIG. 9, having a height of 3 mm and a seating surface diameter of 3.4 mm. Thus, the three distinct pieces of information obtained from the top of the healing abutment allow the clinician or laboratory to know (i) the orientation of the hex of the implant, (ii) the height of the healing abutment (i.e., the location of the implant's seating surface below the healing abutment), and (iii) the seating surface diameter of the healing abutment (or the size of the implant's seating surface).

The healing abutment 806 in FIG. 9b possesses a binary code of 0100 because only one information marker 807 is present in the second marking location. Thus, it is understood from the binary code that the healing abutment 806 is 3 mm in height and has a seating surface diameter of 4.1 mm. The two healing abutments 811, 816 in FIGS. 9c, 9d have binary codes of 1000 and 1100, respectively. Healing abutment 811 has an information marker 812 in the first marking location, while healing abutment 816 has information markers 817, 818 in the first two locations. Thus, the unique characteristics of these two healing abutments are known.

The healing abutments 821, 826, 831, 836 shown in FIGS. 9e-9h and having heights of 4 mm, but with varying seating surface diameters, would be interpreted as having binary codes 0010, 0110, 1010, and 1110, respectively. Healing abutment 821 has one information marker 822 present in the third marking location, thus resulting in a binary code of 0010, which is indicative of a healing abutment height of 4 mm and a seating surface diameter of 3.4 mm. Similar analyses on healing abutment 826 with information markers 827, 828, healing abutment 831 with information markers 832, 833, and healing abutment 836 with information markers 837, 838, 839 allow determinations of the unique characteristics of these healing abutments.

The healing abutments 841, 846, 851, 856 shown in FIGS. 9i-9l and having heights of 6 mm, but with varying seating surface diameters, would be interpreted as having binary codes 0001, 0101, 1001, and 1101, respectively. Healing abutment 841 has one information marker 842 present in the fourth marking location, thus resulting in a binary code of 0001, which is indicative of a healing abutment height of 6 mm and a seating surface diameter of 3.4 mm. Similar analyses on healing abutment 846 with information markers 847, 848, healing abutment 851 with information markers 852, 853, and healing abutment 856 with information markers 857, 858, 859 allow determinations of the unique characteristics of these healing abutments.

The healing abutments 861, 866, 871, 876 shown in FIGS. 9m-9p and having heights of 8 mm, but with varying seating surface diameters, would be interpreted as having binary codes 0011, 0111, 1011, and 1111, respectively. Healing abutment 861 has two information markers 862, 863, which is indicative of a healing abutment height of 8 mm and a seating surface diameter of 3.4 mm. Similar analyses on healing abutment 866 with information markers 867, 868, 869, healing abutment 871 with information markers 872, 873, 874, and healing abutment 876 with information markers 877, 878, 879, 880 allow determinations of the unique characteristics of these healing abutments.

While the matrix of the sixteen healing abutments in FIGS. 9a-9p show four implant seating surface diameters and four heights, the matrix could include other physical characteristics of the healing abutment. For example, the maximum diameter of the healing abutment could be information obtainable through the binary-coded system. The type of fitting on the healing abutment and, thus, the implant (i.e., internal hex or external hex) could be provided. Information unrelated to the healing abutment, but related to only the implant, could be used. For example, the manufacturer of the implant could be noted. Or, information regarding the type of screw that mates with the internally thread bore of the implant could be provided.

Further, while FIGS. 9a-9p demonstrate the ability of the four digit, binary-coded system to provide two physical characteristics of the healing abutment, it could provide three or more physical characteristics. For example, two seating surface sizes, four heights, and two maximum diameters would provide sixteen unique healing abutments. If more information were needed, a fifth marking location could be added to provide the opportunity for displaying thirty-two physical characteristics of the healing abutments and/or implant. And, while one marking location has been shown with marker, it is possible to have two or more markers in each marking location. For example, one circumferential groove and one radial groove within one location could represent two digits of a binary system. Alternatively, having two widths possible for each groove could provide additional indicia representative of certain information about the healing abutment.

While the invention has been described with round healing abutments, healing abutments anatomically shaped like teeth can take advantage of the information markers. Thus, the set of healing abutments could include components shaped like the various teeth, and the information markers could provide the information regarding which tooth shape is present on the healing abutment. For example, a set may include four types of molar-shaped healing abutments, four types of bicuspid-shaped healing abutments, four types of incisor-shaped healing abutments and four types of round abutments. The four information marker locations on each component in the set provide the information to determine which one of the sixteen healing abutments is being used.

It is contemplated that the present invention also covers a set of eight unique healing abutments (as opposed to the sixteen shown) requiring only three marking locations. The computer software and/or the visual chart in this situation would identify these eight unique healing abutments through binary codes possessing three digits. The potential binary codes corresponding to an ON or OFF determination at the three marking locations are 000, 100, 010, 001, 110, 101, 011, and 111. Similarly, if the set has only four unique healing abutments, only two marking locations would be required on the healing abutments to determine features regarding the healing abutment and the attached dental implant. The potential binary codes in a four healing abutment matrix are 00, 10, 01, and 11.

After the top surface of a healing abutment (or the impression of the top surface, or the model of the impression of the top surface) is analyzed, the orientation of the hex is known from the location of the orientation pick-ups 802 and, via the binary code, the abutment height and the seating surface of the healing abutment is known. Other information regarding the healing abutment and the attached implant can also be determined by adding other markers of the type previously shown.

Figure 9Q:
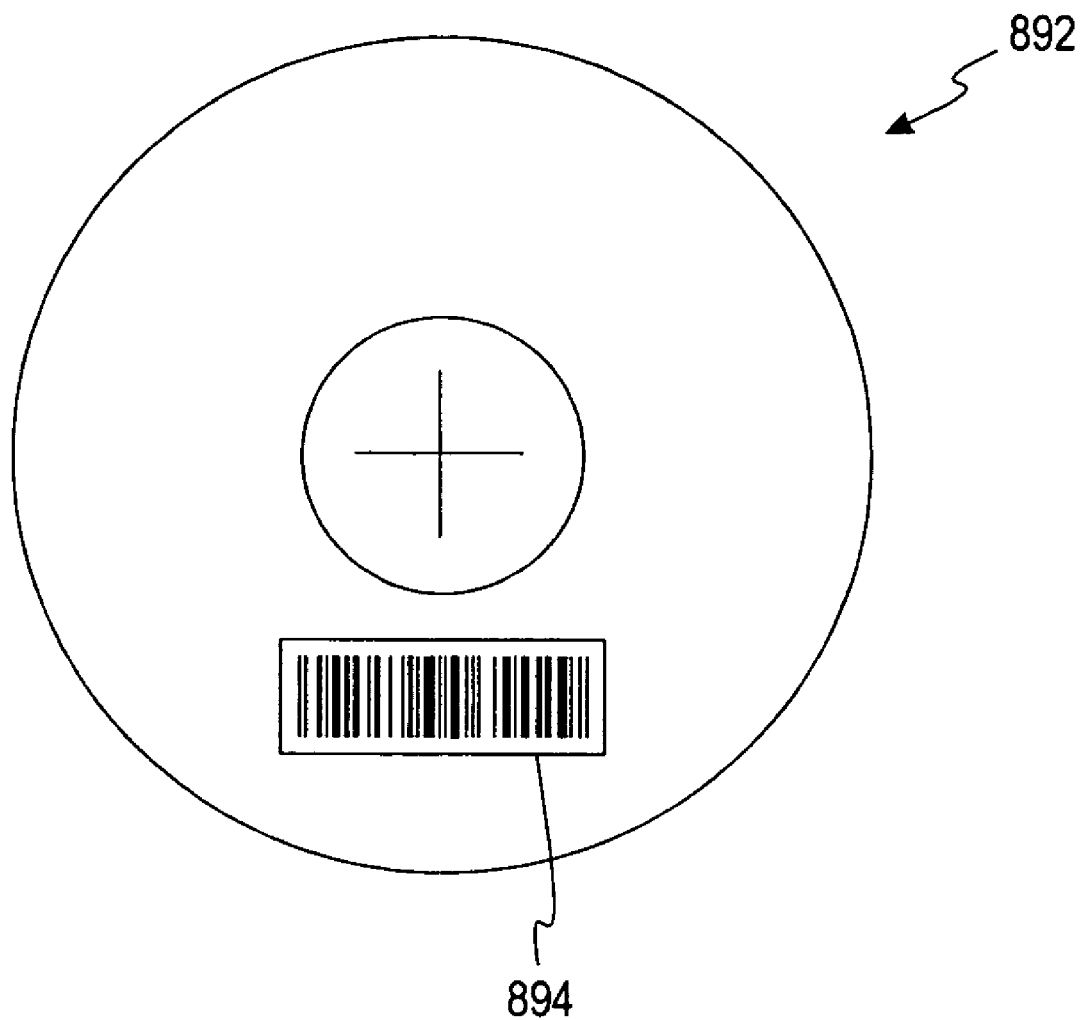

In addition to the markers described, it is further possible to provide a bar-coded system for providing information about the particular component, as shown in FIG. 9q. The bar code 894 can be located on the top surface on the healing abutment 892 such that it can be scanned or read easily. Thus, the bar code 894 would provide the same type of formation described above with respect to the information markers.

Figure 10:
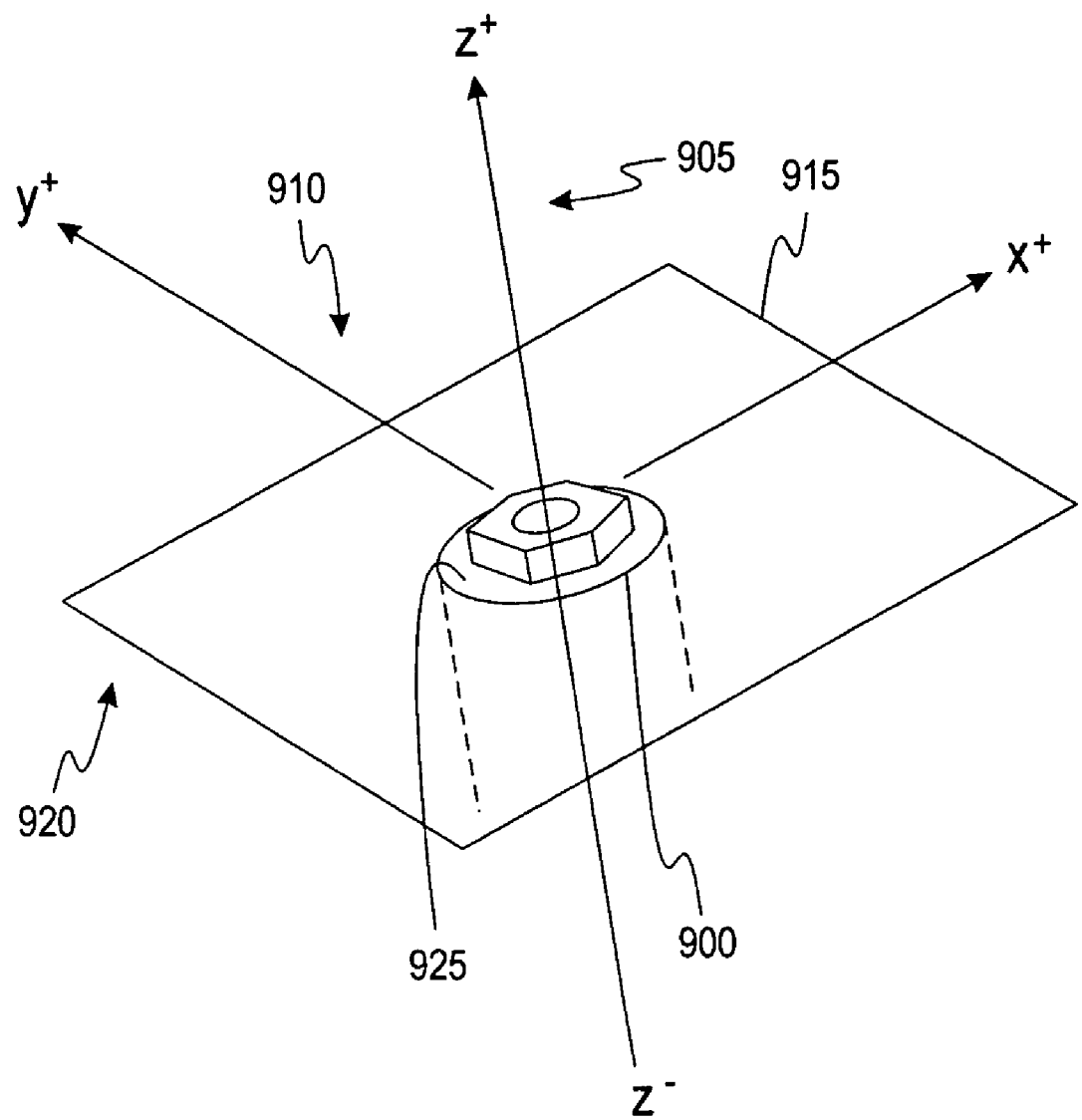
FIG. 10 is a perspective view of a coordinate system of one embodiment of the present invention.

Referring to FIG. 10, when scanning techniques are used to learn of the information on the top of the healing abutment, the computer software is able to determine the position and orientation of the implant 900 relative to the adjacent teeth. The position of the implant 900 is defined in a Cartesian coordinate system having "X," "Y," and "Z" axes. The common point is at the intersection of the centerline of the implant and a plane 920 representing the seating surface 925 of the implant 900.

As noted above, the information markers assist in determining the height of the healing abutment above the implant. This height can be used to identify the zero point on the "Z" axis, which is in the plane 920 containing the seating surface 925 of the implant 900. The "Y" axis 910 is within the plane 920 representing the seating surface 925 with the positive "Y" direction as close to the direction of facial to buccal as possible. The "X" axis 915 is in the plane 920 and is perpendicular to an implant hex face. Thus, the width of the seating surface 925 in the plane 920 is known, as is the width of the healing abutment emerging through the gingiva. Thus, the emergence profile of the artificial tooth is known, as well.

Figure 11:
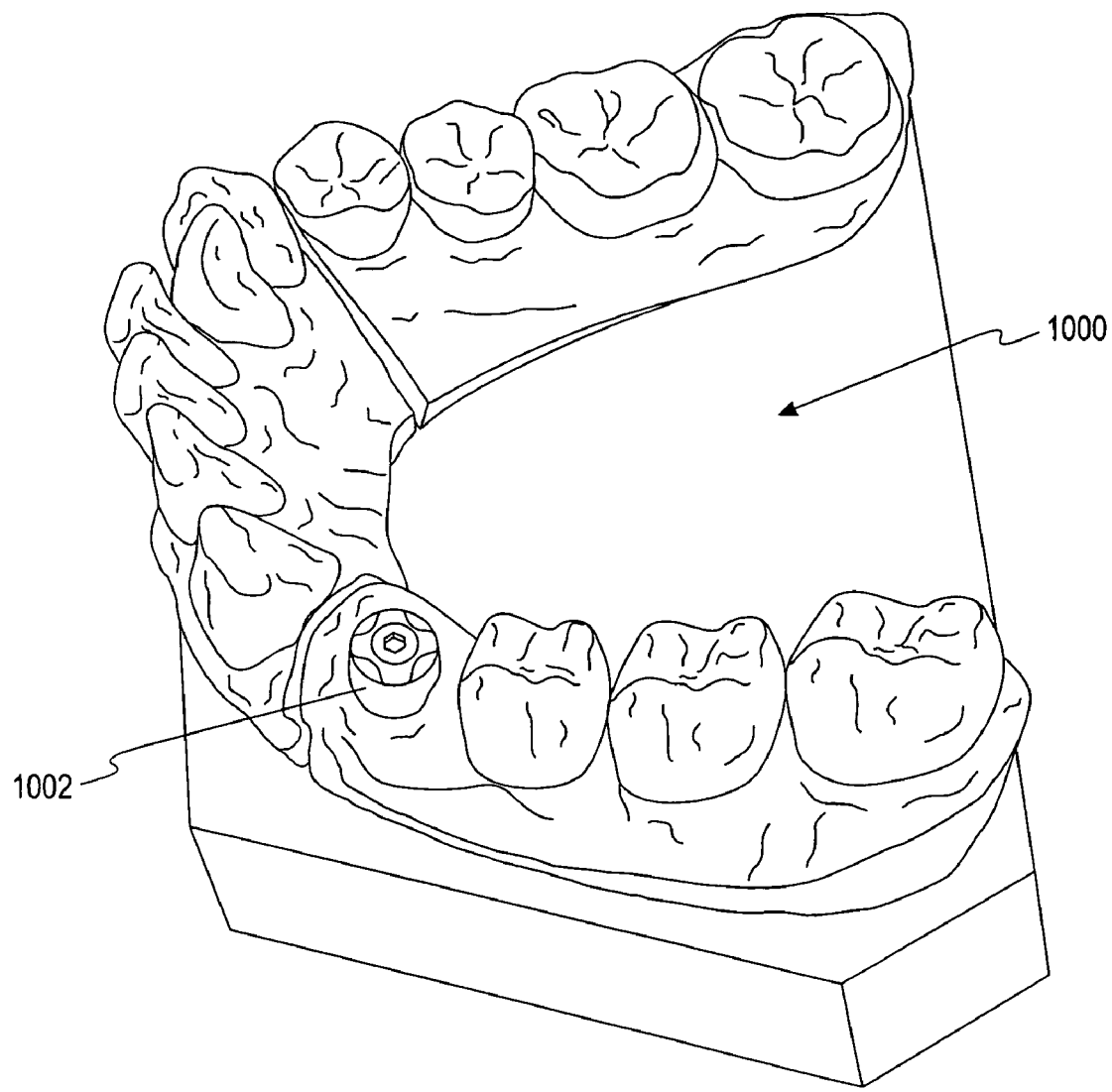
FIG. 11 is a perspective view of a stone model of an impression of a mouth used with one embodiment of the present invention.

Turning now to FIG. 11, a perspective view of a stone cast 1000 of a mouth of a patient is shown with a stone-cast model of a healing abutments 1002 which has configurations on its upper surface that corresponds to the healing abutments previously described. The stone cast 1000 is made from an impression of the mouth as previously described.

Figure 12:
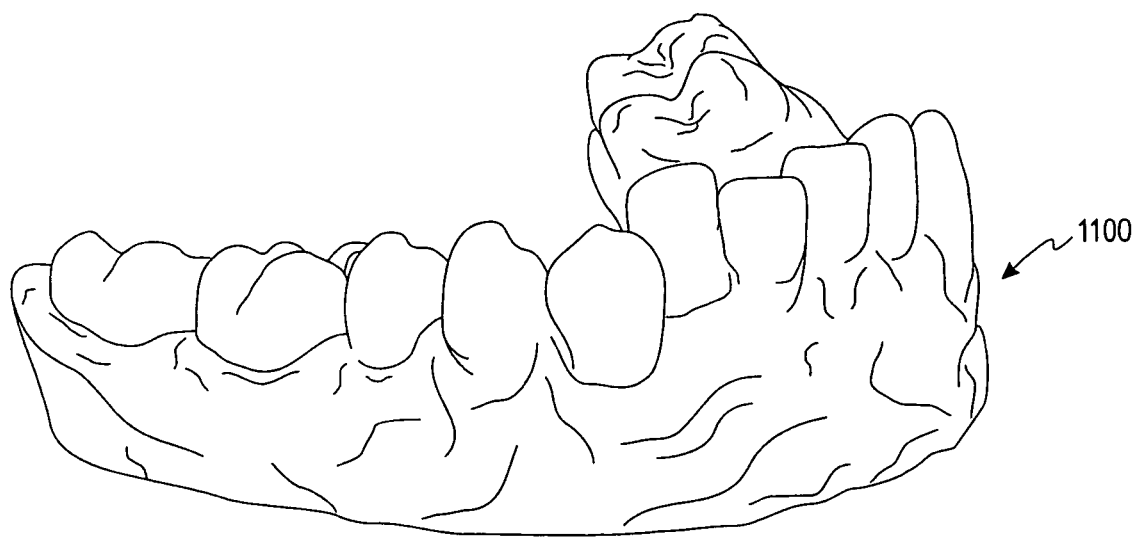
FIG. 12 is a perspective view of a 3-D CAD model of the stone model of FIG. 11.

Once the stone cast 1000 is prepared, it is scanned using a scanning technique previously described, the scanned data is transferred into a graphical imaging program, such as a Computer Aided Design ("CAD") program so that a three-dimensional ("3-D") CAD model 1100 of the stone cast 1000 (FIG. 11) is created, as shown in FIG. 12.

Figure 13:
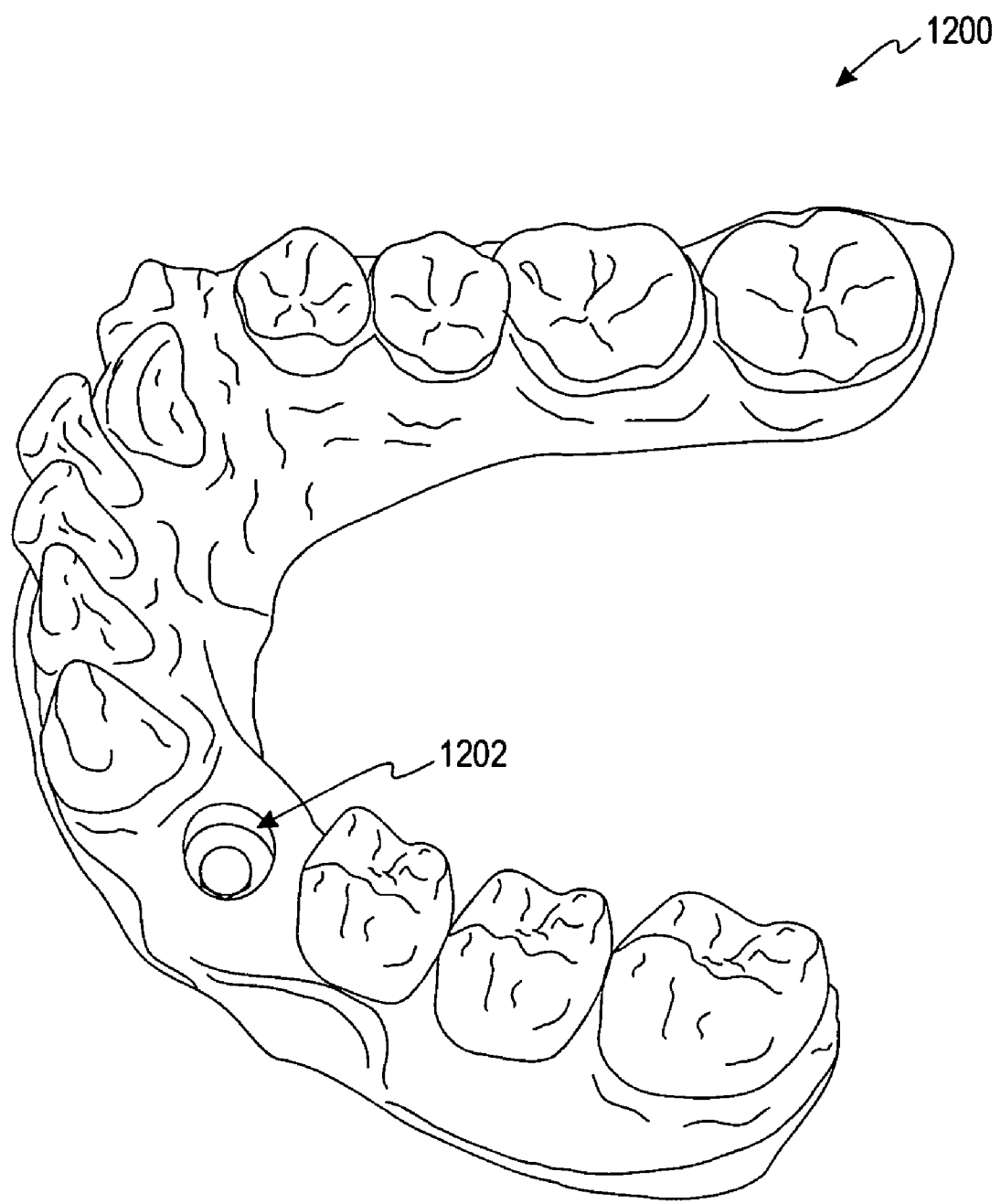
FIG. 13 is a perspective view of an altered 3-D CAD model of FIG. 12 with the healing abutments removed from the CAD model.

As shown in FIG. 13, the CAD model 1100 (FIG. 12) of the stone cast 1000 (FIG. 11) is modified to create a first modified CAD model 1200 that removes the healing abutment 1002 (FIG. 11) so that the position of an implant 1202, or the top surface of an implant, underlying the healing abutment 1002 (FIG. 11) is displayed.

The CAD program is additionally used to design a custom, patient specific, abutment adapted to attach to the implant 1202. The custom abutment supports a final prosthesis, often referred to as a crown. A modified version of the stone model 1000 is used to design the crown to fit between the adjacent teeth based on the specific dimensions and conditions of a patient's mouth. Thus, obtaining an accurate position of the dental implant is critical to designing an accurate crown. Once the CAD program has been used to design a custom abutment, the design of the custom abutment is input into a precision manufacturing device, such as a CNC milling machine, to create the custom abutment from a blank of metal, usually titanium, or a titanium alloy, or from a ceramic material.

Figure 14:
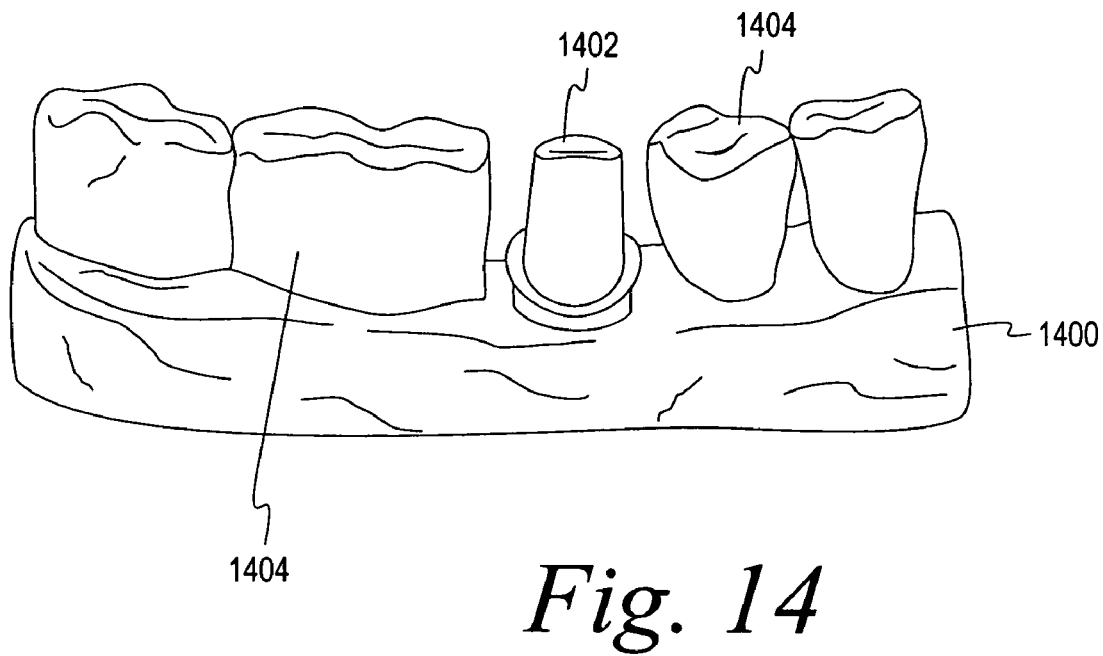
FIG. 14 is a perspective view of an altered 3-D CAD model of FIG. 13 with a custom abutment added in the CAD model.
Figure 15:
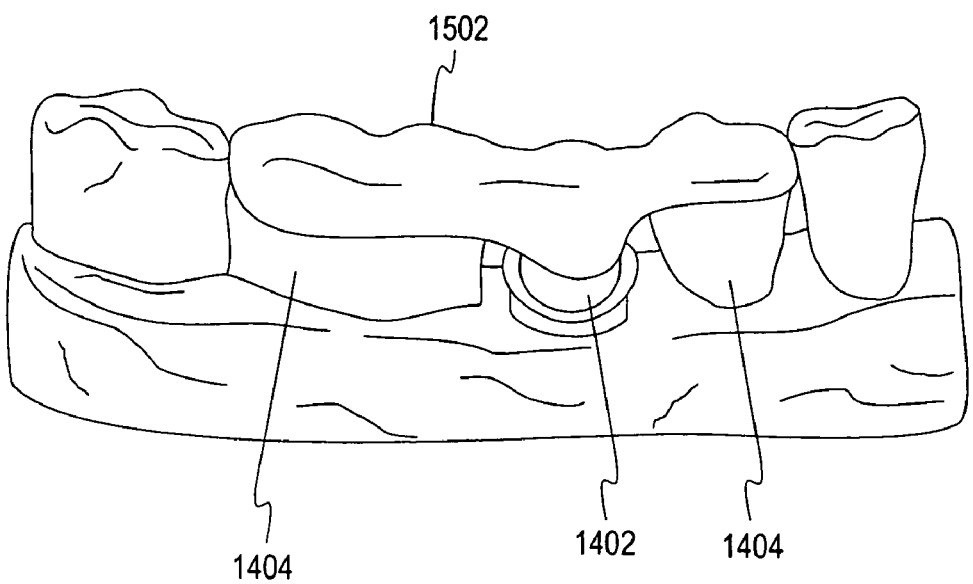
FIG. 15 is a perspective view of a 3-D CAD model with an overmold attached over the custom abutment and the adjoining teeth.

As shown in FIG. 14, a CAD model of a custom abutment 1402 is shown located between a CAD model of the adjacent teeth 1404 that has been created by scanning the stone model 1000. Using the CAD program, an overmold 1502 is created, as shown in FIG. 15. The overmold 1502 fits over the custom abutment 1402 and the adjacent teeth 1404 in the 3-D CAD model 1400. The overmold 1502 is adapted to fit over a stone model of the patient's teeth to allow an actual custom abutment 1604 (FIG. 18) to be positioned in substantially the identical location and orientation as the custom abutment 1402 in the 3-D CAD model 1400.

Once the overmold 1502 has been designed in the 3-D CAD model 1400, the CAD program allows a rapid prototype overmold 1602 (FIG. 16) corresponding to the 3-D CAD model of the overmold 1502 to be created using rapid prototype equipment. It is contemplated that many rapid prototyping techniques may be utilized with the present invention such as: stereolithography, laminated-object manufacturing, selective laser sintering, solid ground curing, or other known rapid prototyping processes. The 3-D CAD model of the overmold 1502 is used by the equipment controlling the rapid prototype equipment to create the rapid prototype overmold 1602.

Figure 16:
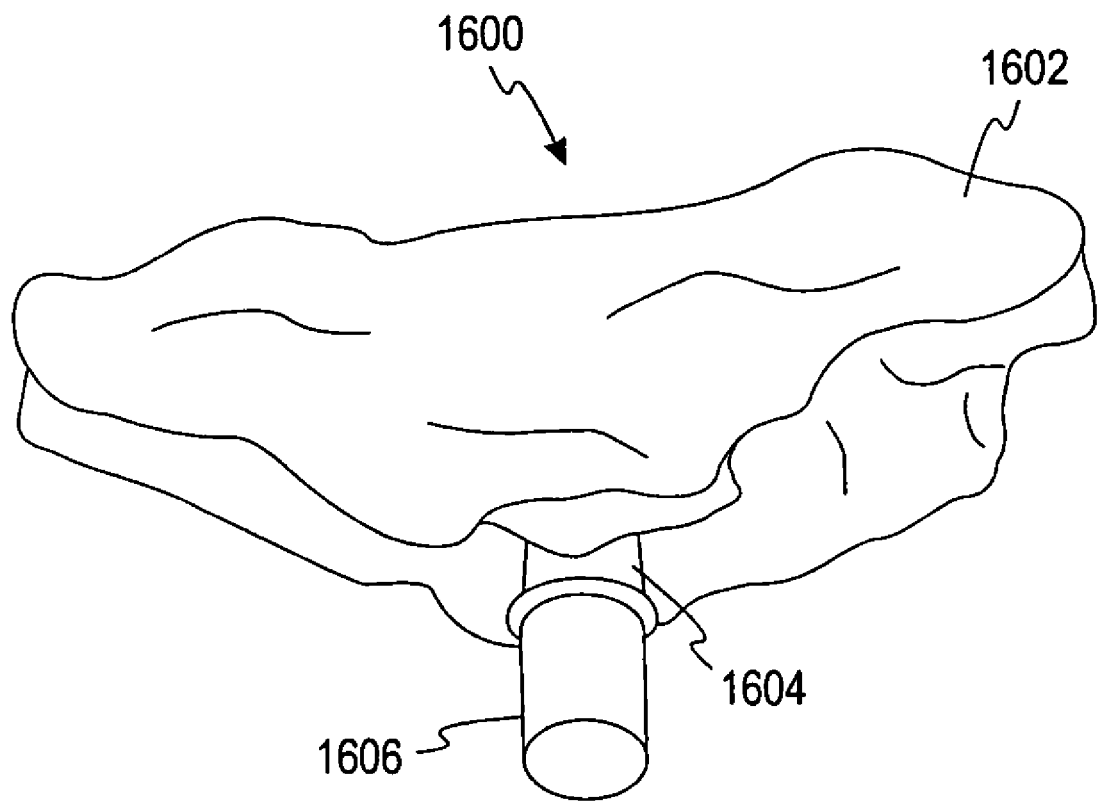
FIG. 16 is a perspective view of a rapid prototype of the overmold shown in the 3-D CAD model of FIG. 15 including an implant analog and an abutment.

Turning now to FIG. 16, a rapid prototype assembly 1600 is shown having the rapid prototype overmold 1602, a custom abutment 1604, and an implant analog 1606. The rapid prototype overmold 1602 is adapted to receive the custom abutment 1604 via a snap-fit connection created by snapping the overmold 1602 over an edge of the custom abutment 1604. It is additionally contemplated that a press fit may be used to secure a custom abutment to a rapid prototype overmold by using an interference fit. The custom abutment 1604 is secured to the implant analog 1606 using a screw.

Figure 17:
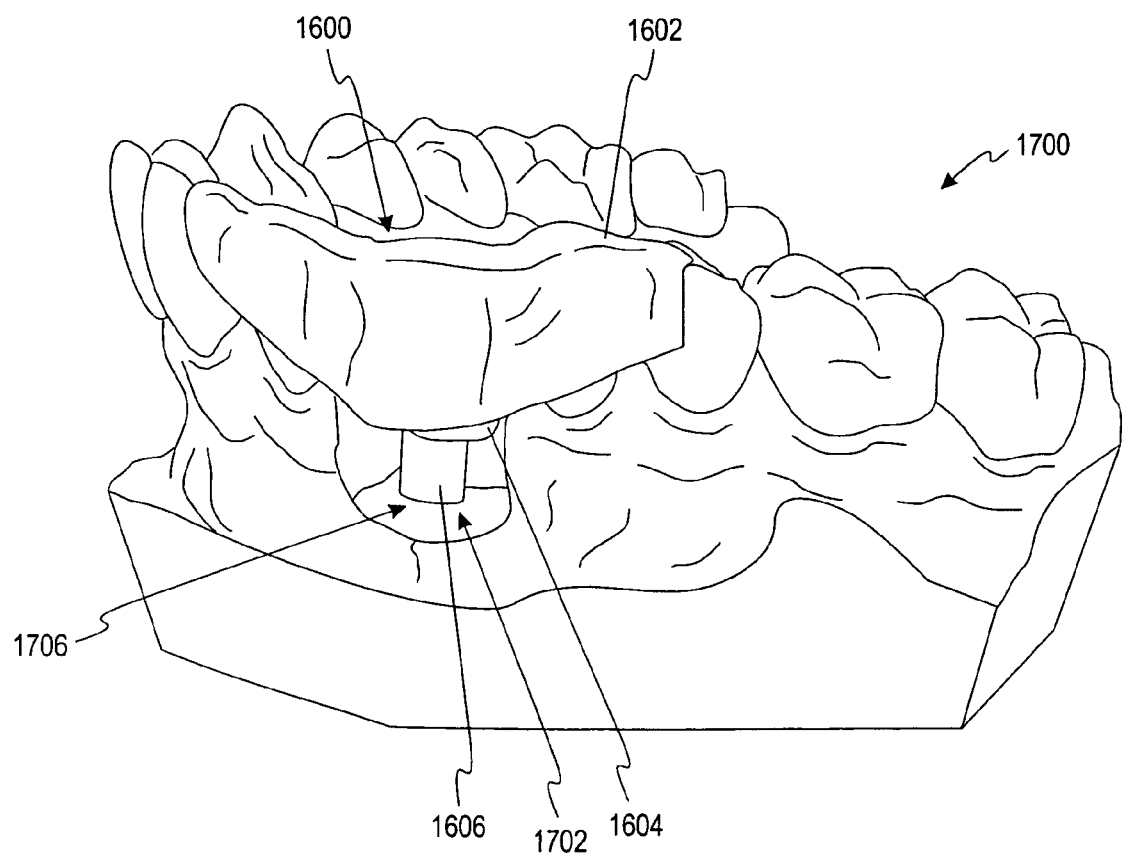
FIG. 17 is a perspective view of an altered stone model of FIG. 11 with the overmold of FIG. 16 attached.
Figure 18:
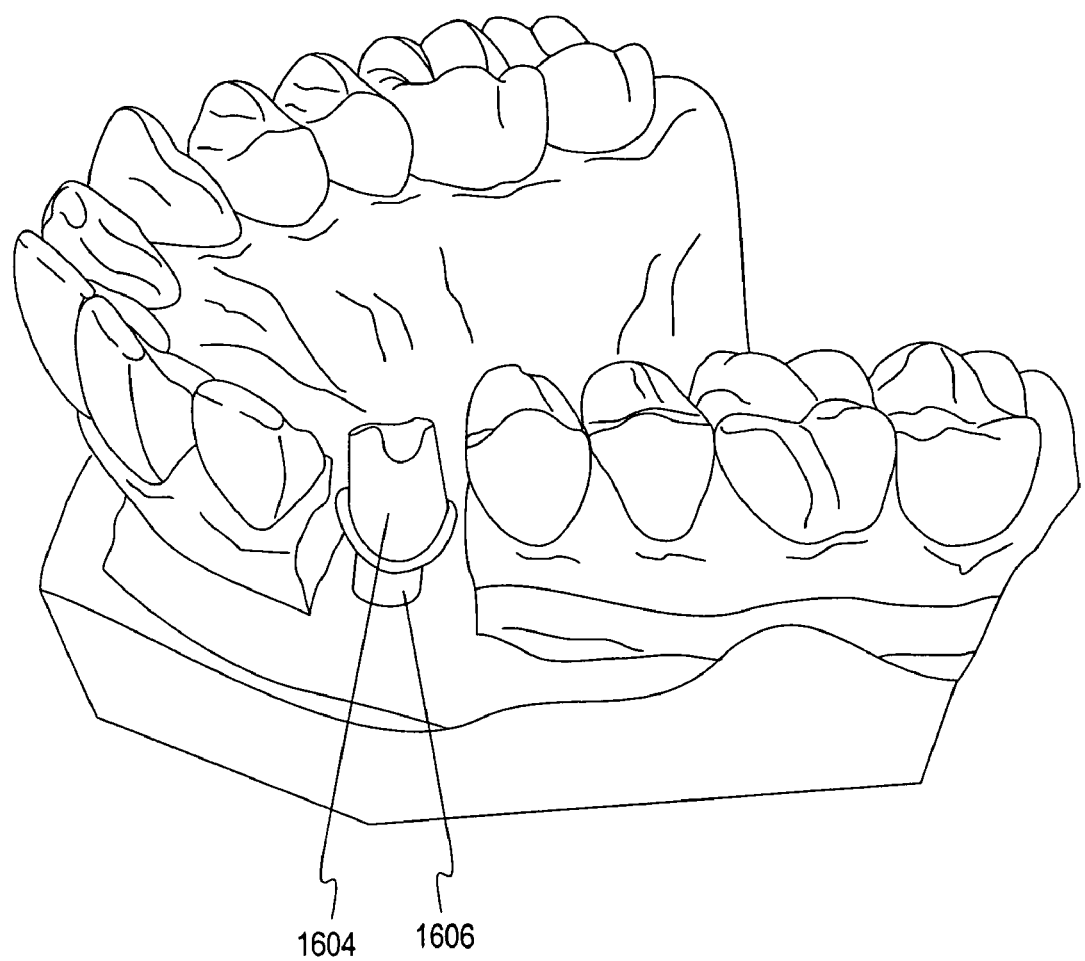
FIG. 18 is a perspective view of the altered stone model of FIG. 17 with the overmold removed and the implant analog placed in the stone model and the patient-specific abutment connected to the implant analog.

The custom abutment 1604 (FIG. 18) produced on the precision manufacturing device must then be placed within an altered stone model 1700 as shown in FIG. 17, so that the crown may be created. The altered stone model 1700 has had the healing abutment 1002 from the stone cast 1000 (FIG. 11) removed, so that an opening 1702 is present where the healing abutment 1002 from the stone cast 1000 (FIG. 11) had been located. The opening 1702 is of a sufficient size so as to receive the implant analog 1606. A gap 1706, or a hole large enough to receive an implant analog, exists in the stone model 1700 between the implant analog 1606 and the walls defining the opening 1702. The rapid prototype assembly 1600 is placed over the stone model 1700, positioning the custom abutment 1604 and the implant analog 1606 as in the 3-D CAD model. The gap 1706 is then filled with a securing material, such as epoxy, to secure the implant analog 1606 to the stone model 1700. Once the securing material sets, the implant analog 1606 is properly positioned within the stone model 1700, at substantially the same location as the implant in the patient's mouth relative to the teeth adjacent to the implantation site. The implant analog 1606 and the custom abutment 1604 may be removed from the rapid prototype overmold 1602, as shown in FIG. 18. The final prosthesis may then be created using the stone model 1700 having the properly positioned implant analog 1606 and custom abutment 1604.

Thus according to the present invention, the same stone model may be used for a scanning process to make the patient specific custom abutment 1604 and for receiving an implant analog 1606 for mating with the custom abutment 1604 to develop a final prosthesis.

While the preceding embodiment has been described for creating a final prosthesis, it is contemplated that the process may be used to create a temporary prosthesis as well.

According to another embodiment of the present invention, an implant analog is placed within a stone model using a robot manipulator. As previously described herein, a stone cast 1000 of a mouth of a patient is produced from taking an impression of the patient's mouth. The stone cast is scanned to generate a 3-D CAD model 1100 of the stone cast 1000. The CAD program is used to design a custom abutment 1604. The custom abutment 1604 is produced on a precision manufacturing device using information from the CAD program.

Figure 19A:
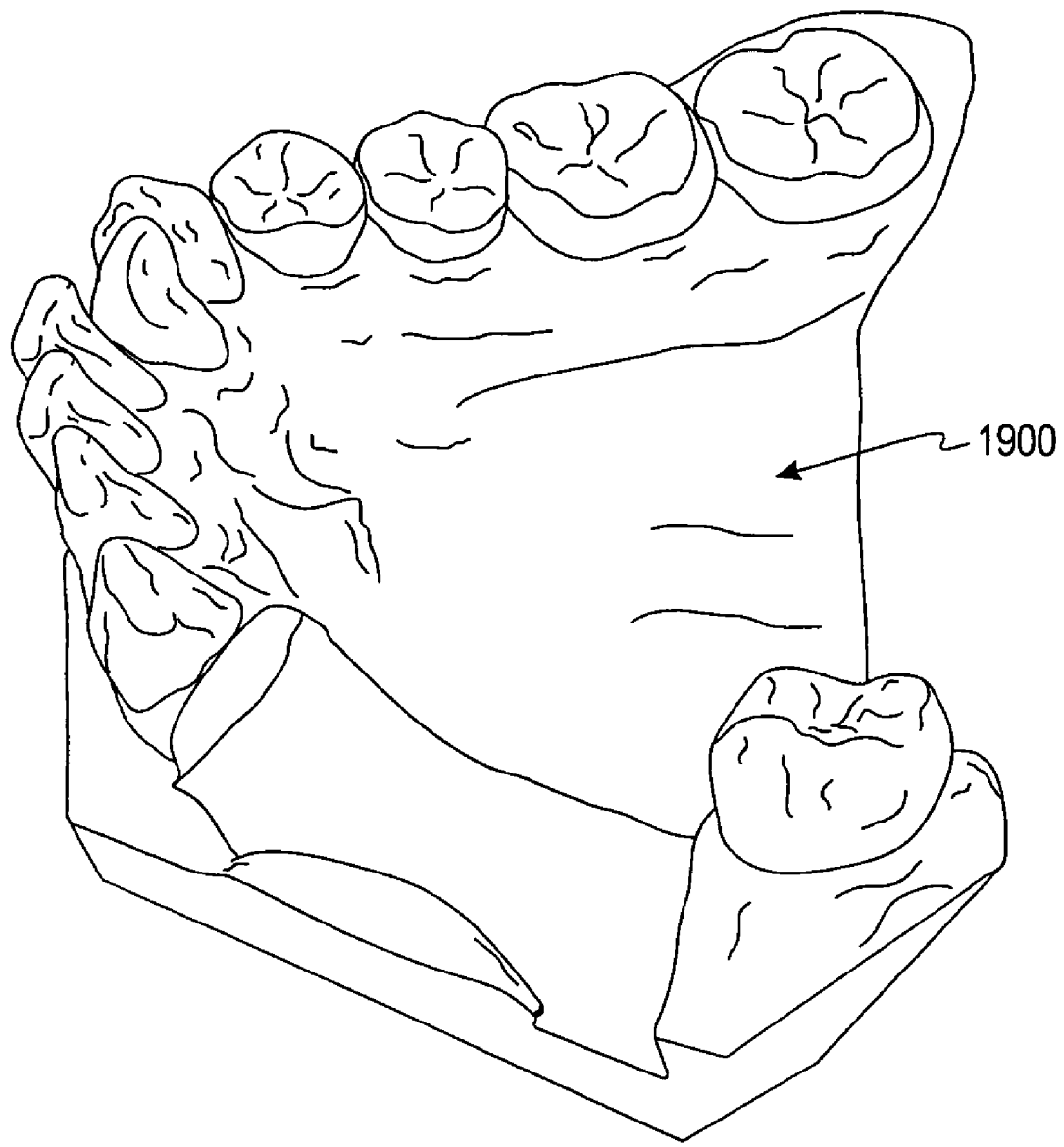
FIG. 19a is a perspective view of an embodiment of an altered stone model of a mouth with abutments removed.
Figure 20:
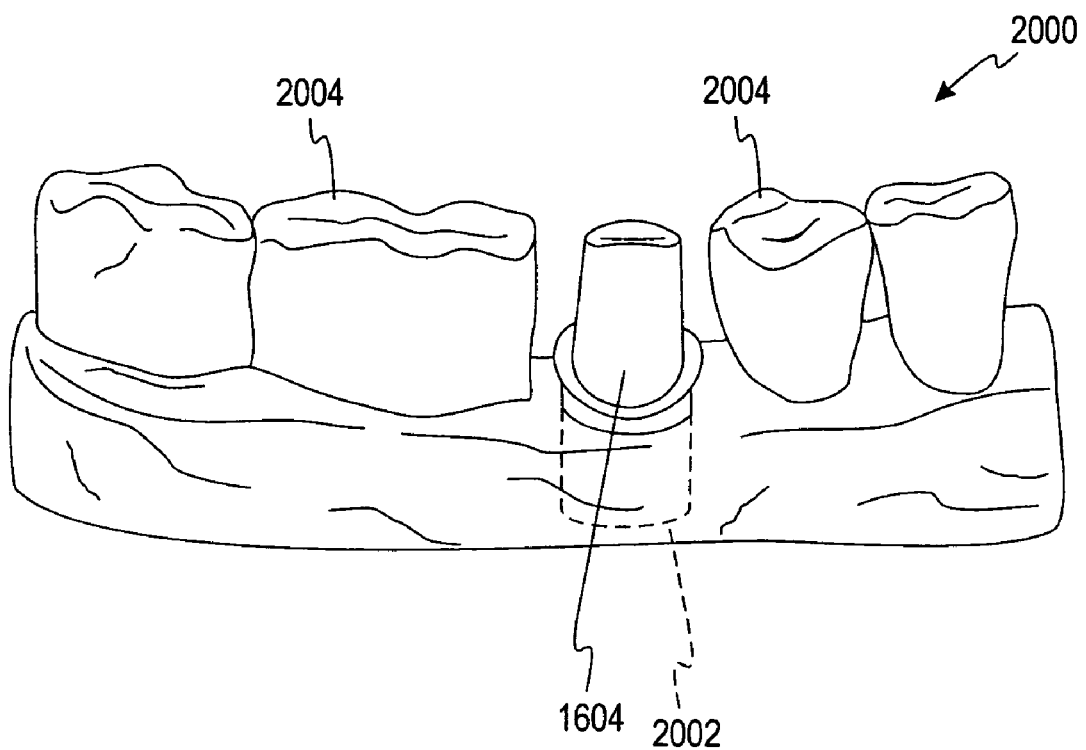
FIG. 20 is a perspective view of a 3-D CAD model of a custom abutment implant analog placed within a mouth.
Figure 21:
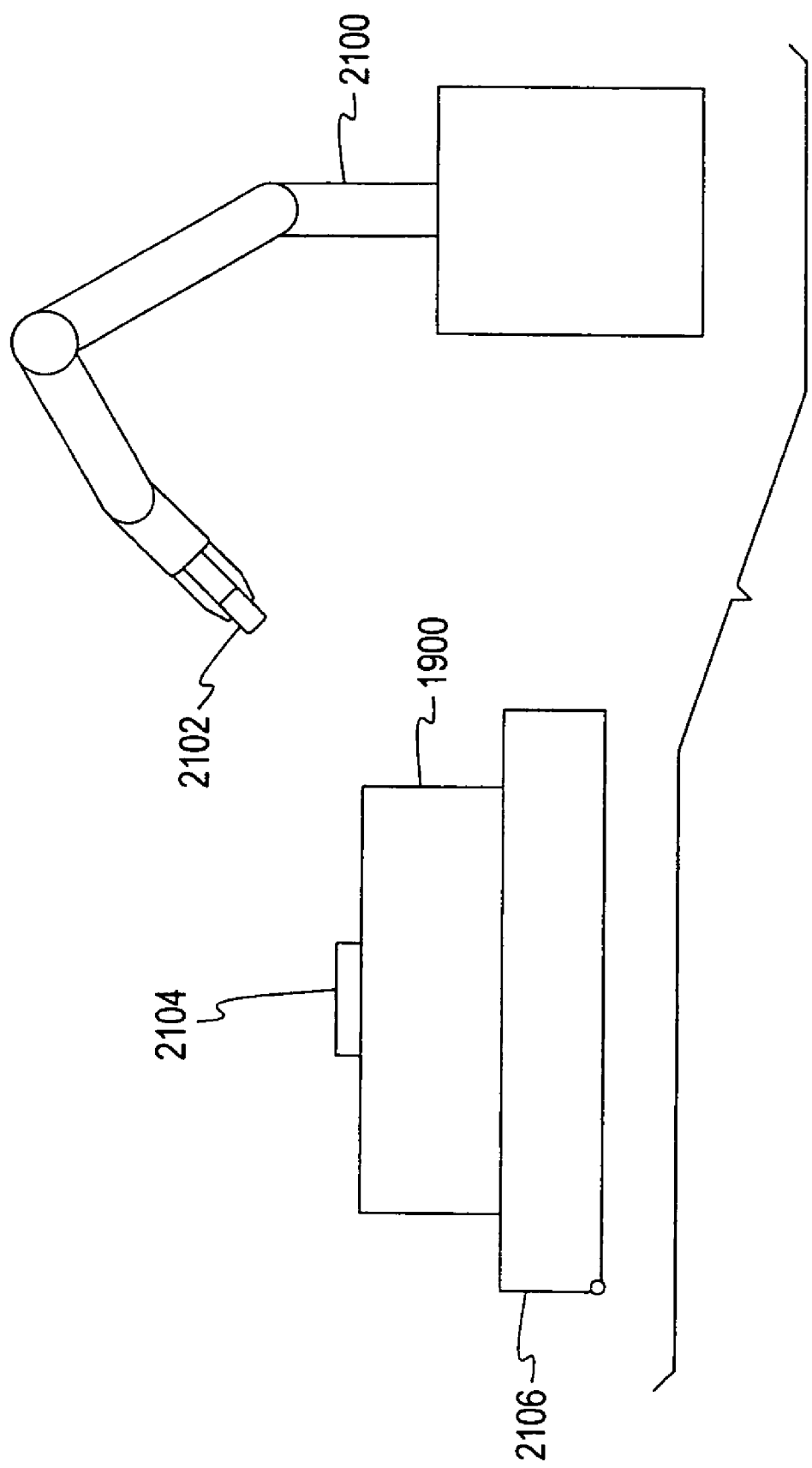
FIG. 21 is a schematic representation of a robot manipulator system adapted to place an implant analog into a stone model according to another embodiment of the present invention.

As shown in FIG. 19a, a modified stone cast 1900 is created by removing a section of the stone cast 1000 that contains the healing abutment 1002 (FIG. 11). The CAD program used to generate the custom abutment 1604 is used to generate a 3-D CAD model containing a custom abutment having an implant analog attached. Thus, a 3-D CAD model 2000 exists where the proper position of the implant analog 2002 relative to adjacent teeth 2004 is created as shown in FIG. 20. Using a coordinate system within the 3-D CAD model 2000, the relative position of the implant analogs 2002 and the adjacent teeth 2004 may be generated. A common base plate 2106 (FIG. 21) may be used in scanning the stone cast 1000 and in placing an implant analog 2102 (FIG. 21) using a robot manipulator 2100 (FIG. 21). The robot manipulator 2100 (FIG. 21) is located at a known position relative to the base plate 2106 (FIG. 21). A scanner measures an X, Y, and Z position of the healing abutment 1002 in the stone cast 1000 relative to axes on the base plate 2106, also referred to as the base plate 2106 origin. Thus, when the base plate 2106 is in a known position with respect to the robot manipulator 2100, an exact location of an implant analog 2102 (FIG. 21) may be determined.

Once the relative position of the implant analog 2002 and the adjacent teeth 2004 has been generated, this position information is input to a robot manipulator. The robot manipulator 2100 uses the relative position information to place an implant analog 2102 into a securing material 2104, such as epoxy, located on the modified stone cast 1900 where the healing abutments had been located, as shown schematically in FIG. 21. The robot manipulator 2100 is able to accurately place the implant analog 2102 in the securing material 2104, such that the position of the implant analog 2102 within the modified stone cast 1900 is substantially identical to the position of the implant analog 2002 within the 3-D CAD model 2000.

Figure 19B:
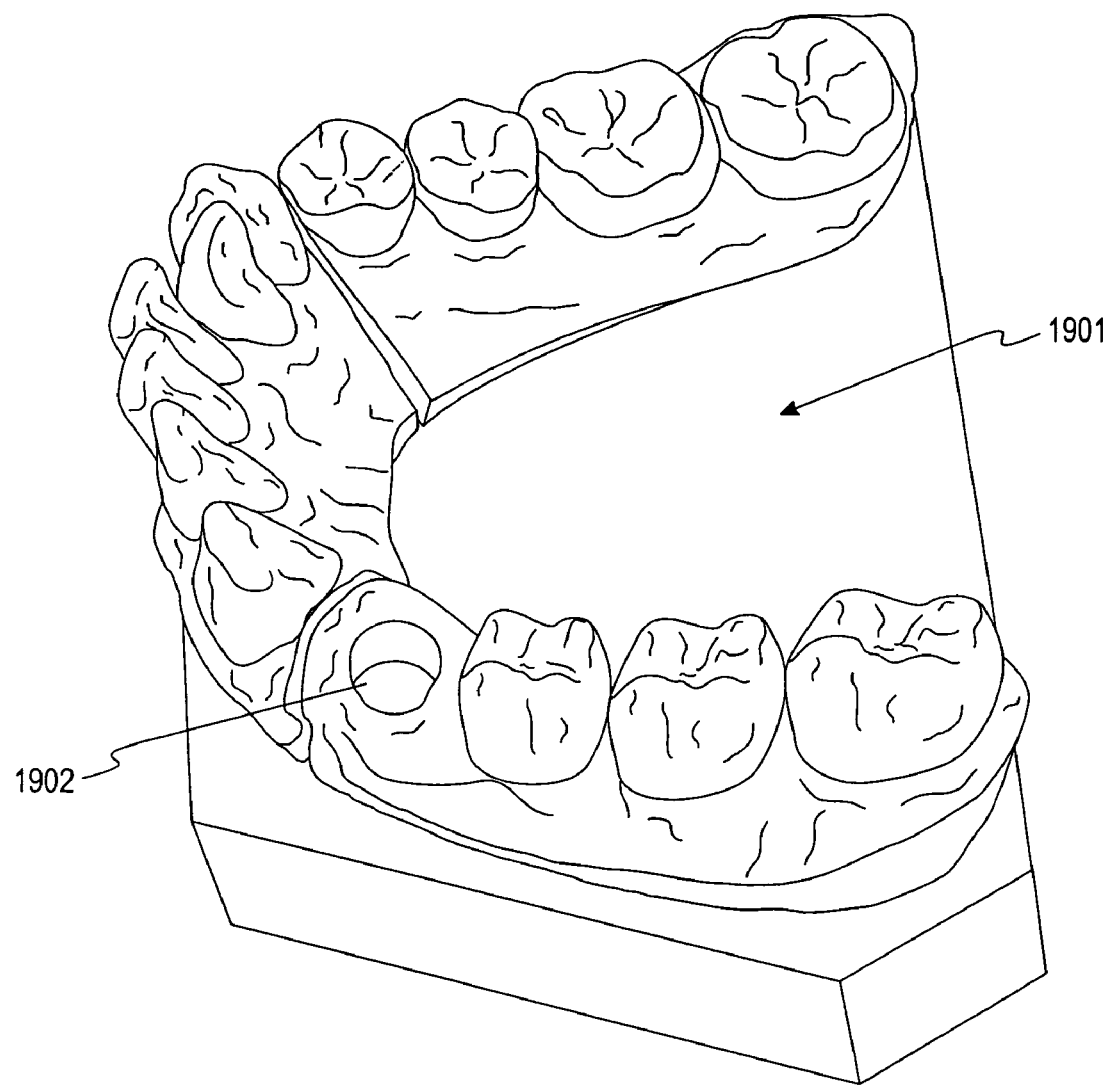
FIG. 19b is a perspective view of an alternative embodiment of an altered stone model of a mouth with abutments removed.

According to a further alternative embodiment of the present invention, instead of using a robot manipulator to place an implant analog into a securing material of a modified stone cast, the robot manipulator may instead be a multiple handed robot manipulator adapted to drill a hole 1902 in a stone cast 1901 (as shown in FIG. 19b) with a first hand, and place an implant analog in the hole with a second hand. One example of a robot that performs multiple drilling functions and accurately places the implant analog into the drilled hole in the stone cast 1901 is described with reference to FIGS. 22-28.

Figure 22:
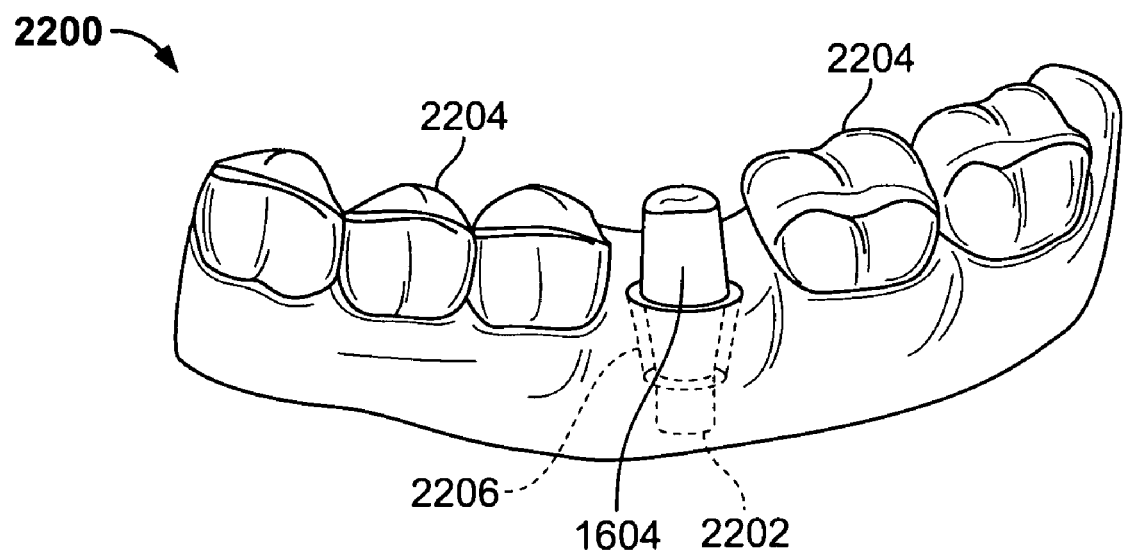
FIG. 22 is a 3D computer model (a virtual model) of a portion of a patient's mouth.

FIG. 22 is similar to FIG. 20 in that it illustrates a 3-D CAD model 2200 (on a computer display) of a virtual custom abutment 1604 and a virtual implant analog 2202 that are adjacent to teeth 2204 after a stone cast of the patient's mouth has been scanned. An opening 2206 in the CAD model 2200 is tapered as it leads towards the virtual implant analog 2202. This tapering is chosen by the operator of the CAD model 2200 after consideration of the location of the underlying dental implant that has been dictated by the stone cast model having the healing abutment (e.g., replica of the healing abutment 1002 in stone cast model 1000 in FIG. 11) and the location of the adjacent teeth 2204. Further, the tapering is also dictated by the size and shape of the virtual custom abutment 1604 that has been designed by the operator. Although the opening 2206 has been illustrated having a straight-wall taper, the opening 2206 may have a curved-wall taper. Further, the opening 2206 at its terminal and may be circular, elliptical, or other non-circular shapes as dictated by the virtual custom abutment 1604 and the three-dimensional "saddle" shape of the gingival tissue between the left and right adjacent teeth 2204. This opening 2206 may be created by the robot manipulator 2100 of FIG. 21, or the alternative robot 2300 discussed with reference to FIGS. 23-27.

Figure 23:
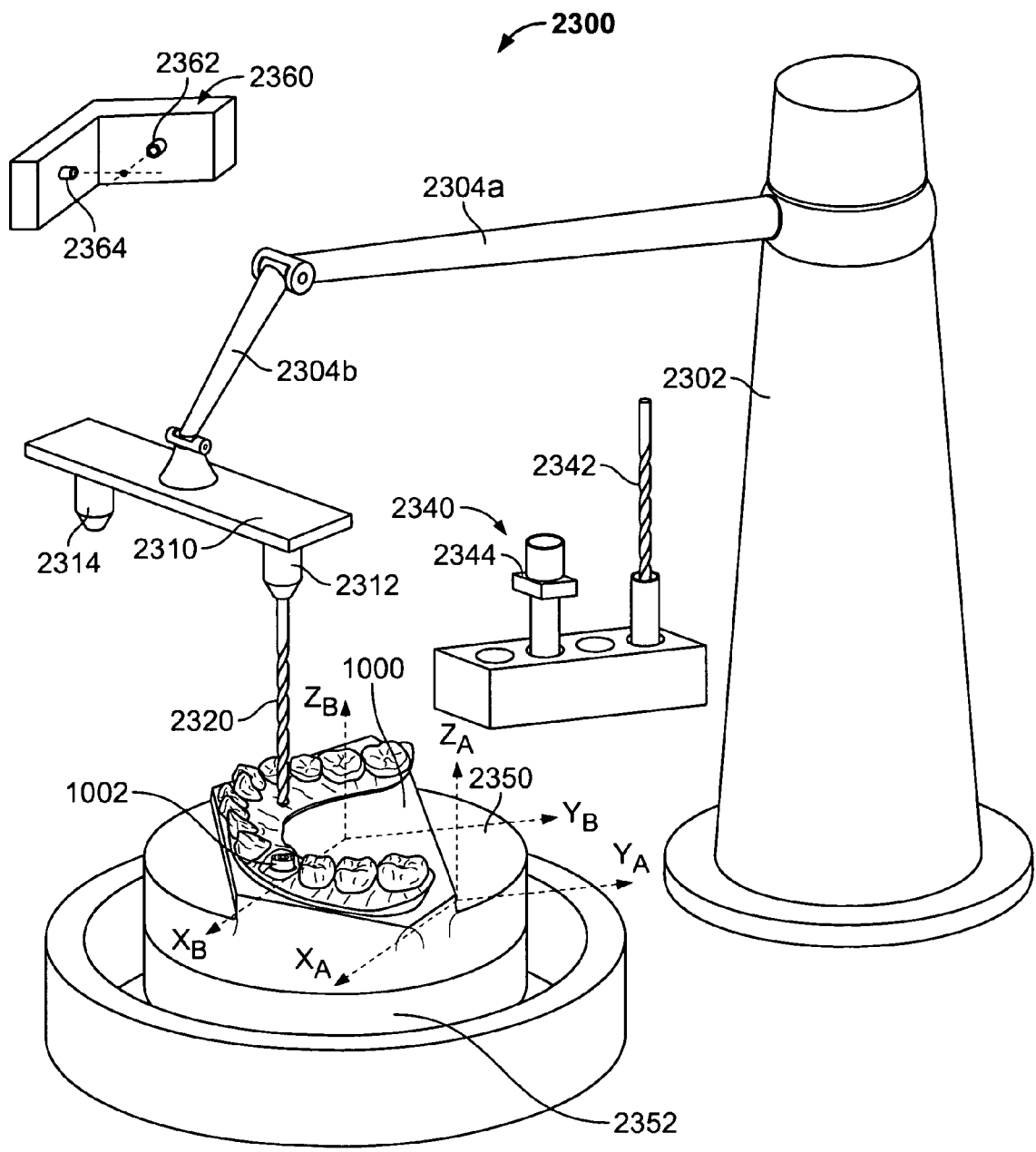
FIG. 23 illustrates a robot that is used to modify the physical model of the patient's mouth.

FIG. 23 illustrates a simple schematic construction for a robot 2300. The skilled artisan would appreciate that numerous types of robots are available having various control features, motors, and manipulating arms and tools. For example, the robot 2300 could be an Epson PS5 six-axis robot with an Epson RC520 controller. The robot 2300 in FIGS. 23-27 performs various functions related to modifying the stone cast 1000 and placing the actual implant analog. In particular, as will be described in more detail below, the robot 2300 modifies the stone cast 1000 to create an actual opening that is substantially similar to the virtual opening 2206 in FIG. 22. Further, the robot 2300 places an implant analog in substantially the same position and with substantially the same orientation as the virtual implant analog 2202 in FIG. 22.

The robot 2300 includes a base structure 2302 that is supported on a table or other work bench. The base structure 2302 typically has one or more moving arms 2304 having a terminal structure 2310 for supporting one or more tool holders 2312, 2314 that grip and/or manipulate tools or other components. As shown, the base structure 2302 includes an arm 2304 having multiple pivotable sections 2304a and 2304b, and the tool holder 2312 includes a drill bit 2320. The terminal structure 2310, the arm 2304, the base structure 2302, and/or the tool holders 2312, 2314 include gears and other common components for transmitting rotational energy to a tool (e.g., the drill bit 2320) being held by one of the tool holders 2312, 2314.

The arm 2304 (and thus the terminal structure 2310) can be moved in all directions relative to the stone cast 1000 and a pallet 2340. The pallet 2340 includes a specific sequence of tools or other components that are placed within the pallet 2340 prior to the operation of the robot 2300. As shown, the pallet 2304 includes an additional drill bit 2342 at one location and an implant analog holder 2344 at a second location. Typically, after the data from the 3-D CAD model 2200 of FIG. 22 is transferred to the control system for the robot 2300, the operator of the robot 2300 will be instructed to provide a certain sequence of tools or other components in the pallet 2340 to accommodate the development of the particular opening and the placement of the particular implant analog for the case.

In FIG. 23, the stone cast 1000 is directly coupled to a base structure 2350 that is the same base structure that was used for scanning the stone model 1000 prior to development of the virtual custom abutment 1604. As such, the base structure 2350 is used in both the scanning of the stone cast 1000 and in the later modification of the stone cast 1000 by the robot 2300. The base structure 2350 includes alignment features and magnetic features for precision mating with corresponding structures on a work structure 2352 associated with the robot 2300. The work structure 2352 is at a known location relative to the base structure 2302 such that any tool or other component within the tool holders 2312, 2314 can be accurately positioned relative to be work structure 2352.

To help arrange for the precision location of the tool 2320 relative to the stone cast 1000, the stone model 1000 (and its base structure 2350) has an abutment coordinate system, which is labeled as $X_A, Y_A, Z_A$, for locating the custom abutment, which will ultimately fit on the implant analog to be located within the opening in the stone cast 1000. Further, the robot 2300 (and the scanning system previously used) has its own base coordinate system, which is labeled as $X_B, Y_B, Z_B$.

When the data from the 3-D CAD model 2200 is transferred to the control system for the robot 2300, the data includes at least three types of data sets. A first data set will indicate the type of implant analog that will be used in the stone cast 1000. A second data set will indicate the relative location of the abutment coordinate system to the base coordinate system so that the creation of the hole in the stone cast 1000 and the placement of the implant analog is substantially identical to that which has been virtually modeled. A third data set will define the gingival margin of the custom abutment 1604 (e.g., having a saddle shape) so that a properly sized opening can be created above the implant analog, allowing the custom abutment to fit properly within the stone cast. This third data set is helpful because the actual custom abutment is larger in diameter than the implant analog such that the opening must be contoured in a tapered fashion (e.g., straight-wall taper, curved wall taper, etc) to accommodate the actual custom abutment.

The robot 2300 of FIG. 23 may also include a calibration mechanism 2360 such that the tool (e.g., the tip end of drill bit 2320) is placed at a known location and "zeroed" before developing the opening and/or placement of the implant analog. As shown, the calibration system 2360 includes two intersecting lasers (e.g., HeNe lasers) 2362, 2364. Prior to any work on the stone cast 1000, the tool is placed at the intersection of the two lasers 2362, 2364 to insure accuracy of the tool within the base coordinate system ($X_B$, $Y_B$, $Z_B$). The operator can slightly adjust the tool to place it at the intersection of the two lasers 2362, 2364, assuming the calibration system 2360 indicates that an adjustment is needed or if the operator can visualize that an adjustment is needed. Once calibration is complete, the robot 2300 moves the tool 2320 directly over the stone replica of the healing abutment 1002, as shown in FIG. 23, as part of a visual verification step. When this occurs, the operator knows that the data entered into the robot 2300 is correct as the robot 2300 is now ready to begin modification of the stone model 1000. Had the drill bit 2320 been placed over the adjacent teeth, and not the stone replica of the healing abutment 1002, then the operator would know that incorrect data has been loaded.

Figure 24:
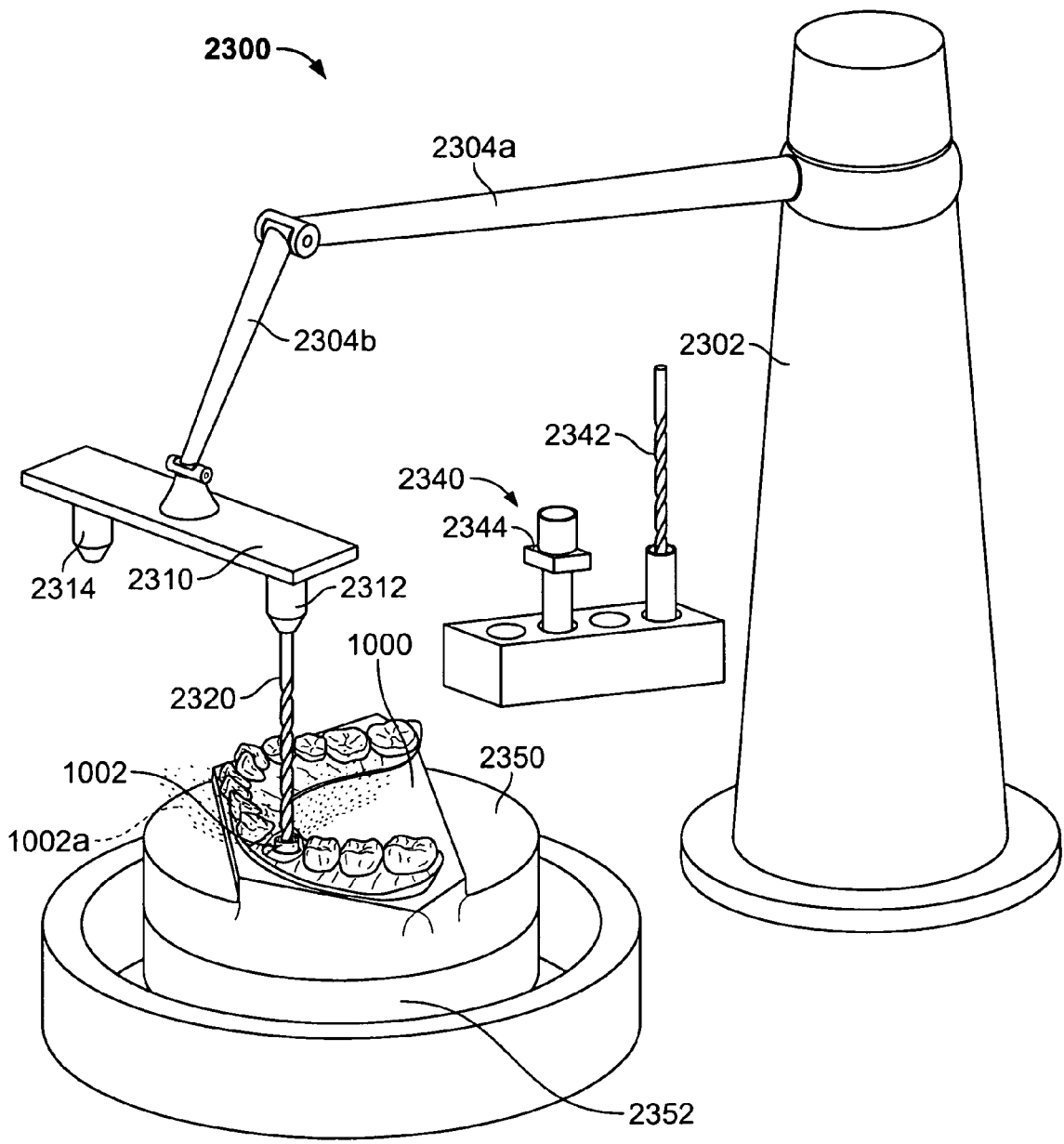
FIG. 24 illustrates the robot of FIG. 23 as it modifies the healing abutment replica on the physical model to create an opening in the physical model.

In FIG. 24, the drill bit 2320 has been moved by the robot 2300 on to the stone replica of the healing abutment 1002 to begin the development of the opening in the stone model 1000. Particles 1002*a* of the healing abutment 1002 are disbursed from the stone model 1000 as the drill bit 2320 works on the stone replica of the healing abutment 1002. Initially, the drill bit 2320 removes the most, if not all, of the protruding structure of the stone replica of the healing abutment 1002. In some instances, corners sections of the protruding structure may remain. The drill bit 2320 then creates the contoured pocket of the opening (as dictated by the tapered opening 2206 in FIG. 22). The drill bit 2320 has a smaller diameter than any portion of the opening such that it is used as a milling tool to create the contoured pocket. The drill bit 2320 then creates the lower portion of the opening that will receive the implant analog. In doing so, the drill bit 2320 of the robot 2300 creates a bottom wall to the opening that is located at a position within the stone cast 1000 that will cause the particular implant analog for that case to have its upper mating surface (see FIG. 27) at a location that is substantially identical to the location of the implant in the patient's mouth, as indicated by the healing abutment that was placed within the patient's mouth and subsequently scanned to develop the 3-D CAD model 2200 of FIG. 22. In doing so, the system takes into account the fact that the implant analog will be held in position in the opening by an adhesive (discussed below), such that it may be suspended in the opening and not in contact with the walls of the opening.

Figure 25:
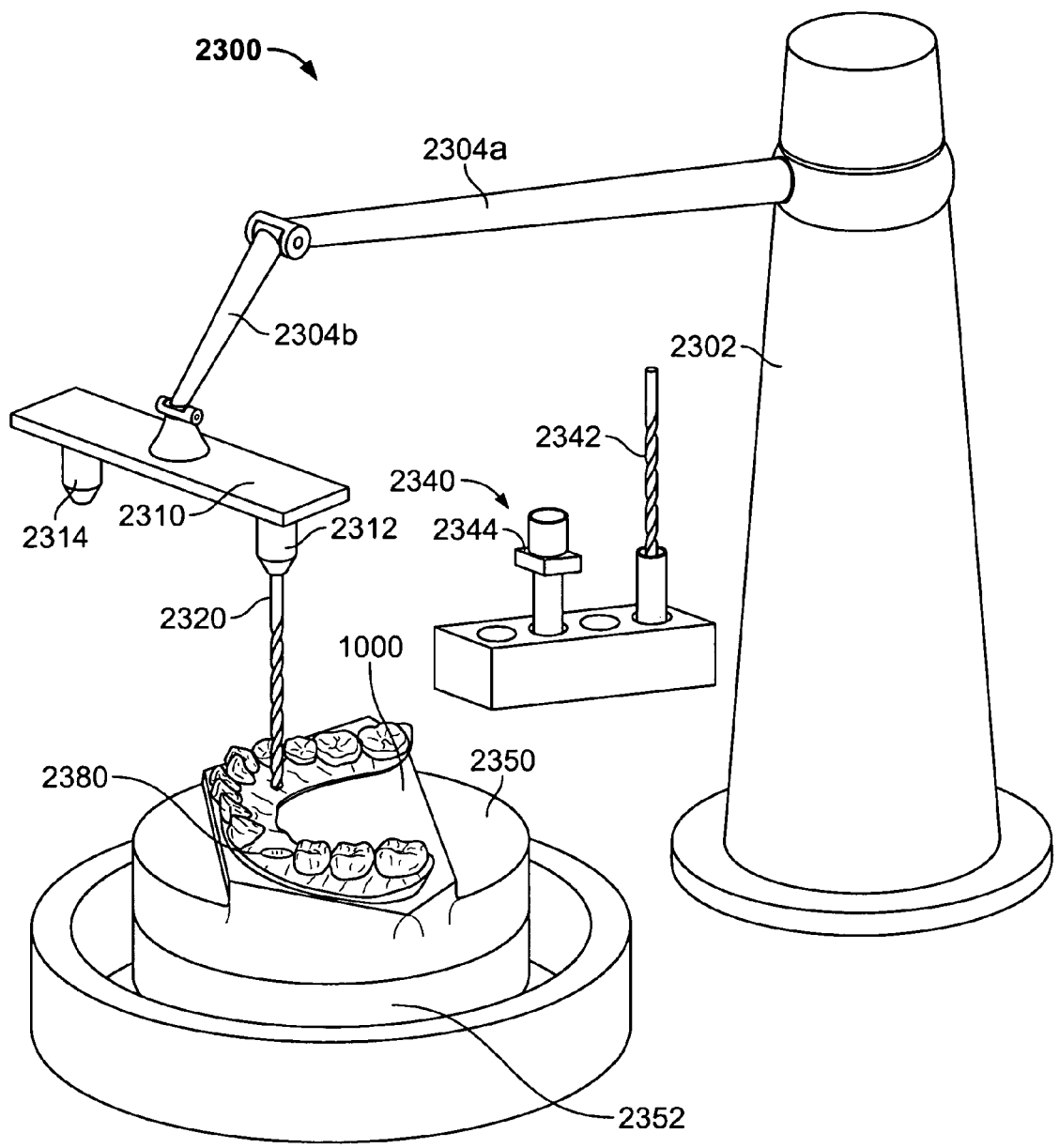
FIG. 25 illustrates the robot of FIG. 23 after it has created an opening in the physical model.

FIG. 25 illustrates the end result of the opening 2380 that was created in the stone cast 1000 by the robot 2300. While the development of the opening 2380 has been described by the use of a single drill bit 2320, it should be understood that the robot 2300 can utilize multiple tools (e.g., a second drill bit 2342 in the pallet 2340, or a more traditional milling tool) to create the opening 2380. Further, because the stone cast may contain multiple replicas of healing abutments 1002, the robot 2300 may be required to create multiple openings 2380, each of which uses multiple tools from the pallet 2340. The use of multiple tools may require a calibration by the calibration system 2360 (FIG. 23) prior to the use of each tool.

Figure 26:
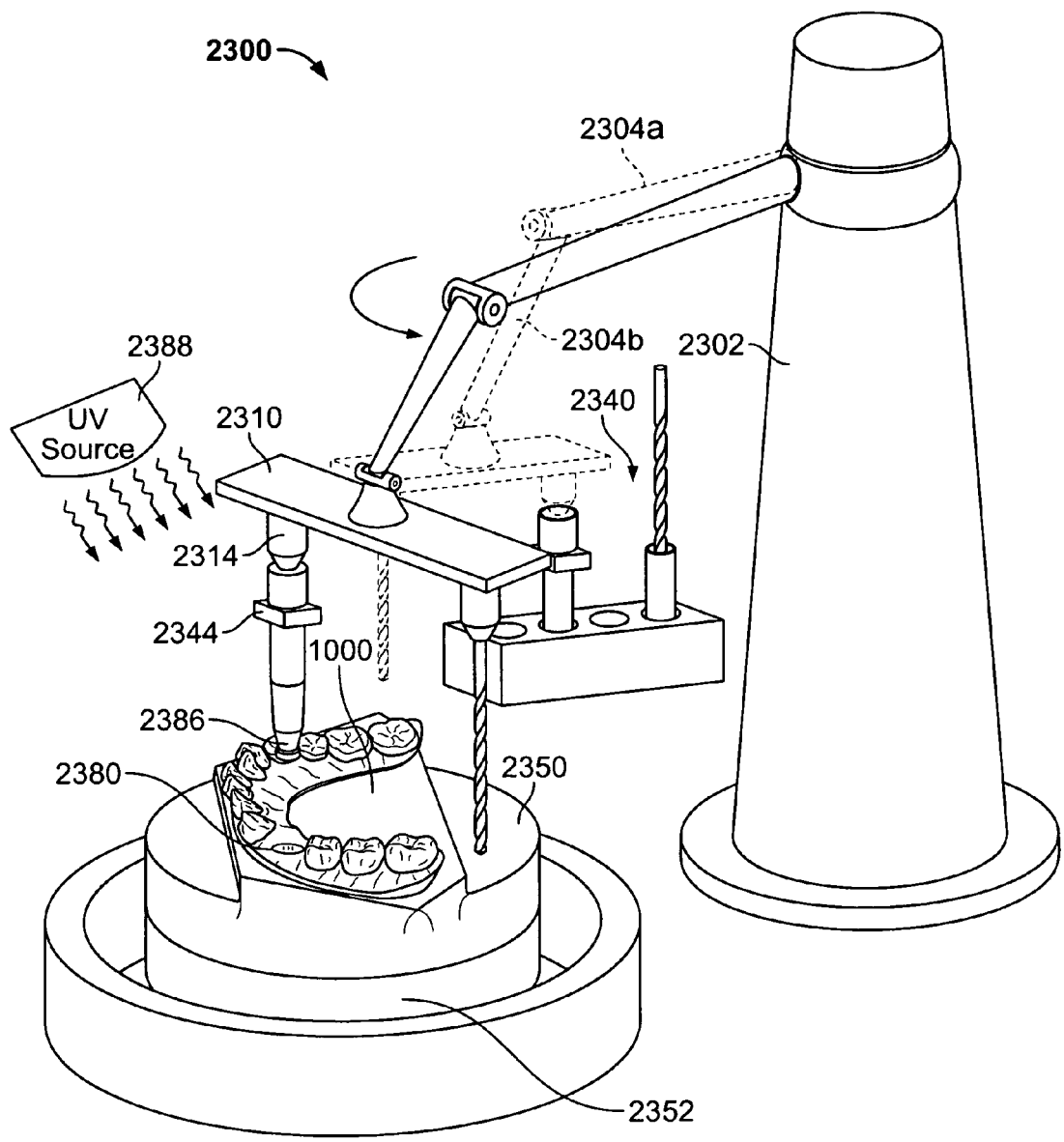
FIG. 26 illustrates the robot of FIG. 23 placing an implant analog in the physical model.

FIG. 26 illustrates the movement of the robot 2300 to grip an implant analog holder 2344 from the pallet 2340 by use of the tool holder 2314 for placement of the implant analog 2386. Once the opening 2380 has been completed, the operator will remove all remaining particles and debris from the drilling process from the stone cast 1000. An adhesive is placed within the opening 2380 and, optionally, also placed (e.g., manually brushed) on the terminal end of the implant analog 2386. Alternatively, an adhesive activator agent is placed on the implant analog 2386 to accelerate the curing process. It should be understood, however, that the work station for the robot 2300 can have bins of adhesive (and activator agents) such that the robot 2300 "dips" the end of the implant analog 2386 into one or more of these bins without manual operator intervention. Further, the robot 2300 may have an adhesive applicator tool in the pallet 2340 that is used to automatically place the adhesive (and possibly the ideal amount of the adhesive) in the opening 2380.

After calibrating the location of the implant analog 2386 with the calibration system 2360 (FIG. 23), the robot 2300 then moves the implant analog holder 2344 in such a manner so as to place the implant analog 2386 at the bottom of the opening 2380. In doing so, the orientation of the anti-rotational feature of the implant analog 2386 is critical such that it matches the orientation of the anti-rotational feature of the implant in the patient's mouth (i.e., all six degrees of freedom are constrained in the same manner as the implant that is located in the patient's mouth). When the robot 2300 has finished placement of the implant analog 2386 within the opening 2380, an energy source (e.g., UV light source) is used to quickly cure the adhesive such that the implant analog 2386 is physically constrained and attached to the stone model 1000 within the opening 2380. Preferably, the adhesive is a UV-curable adhesive.

Figure 27:
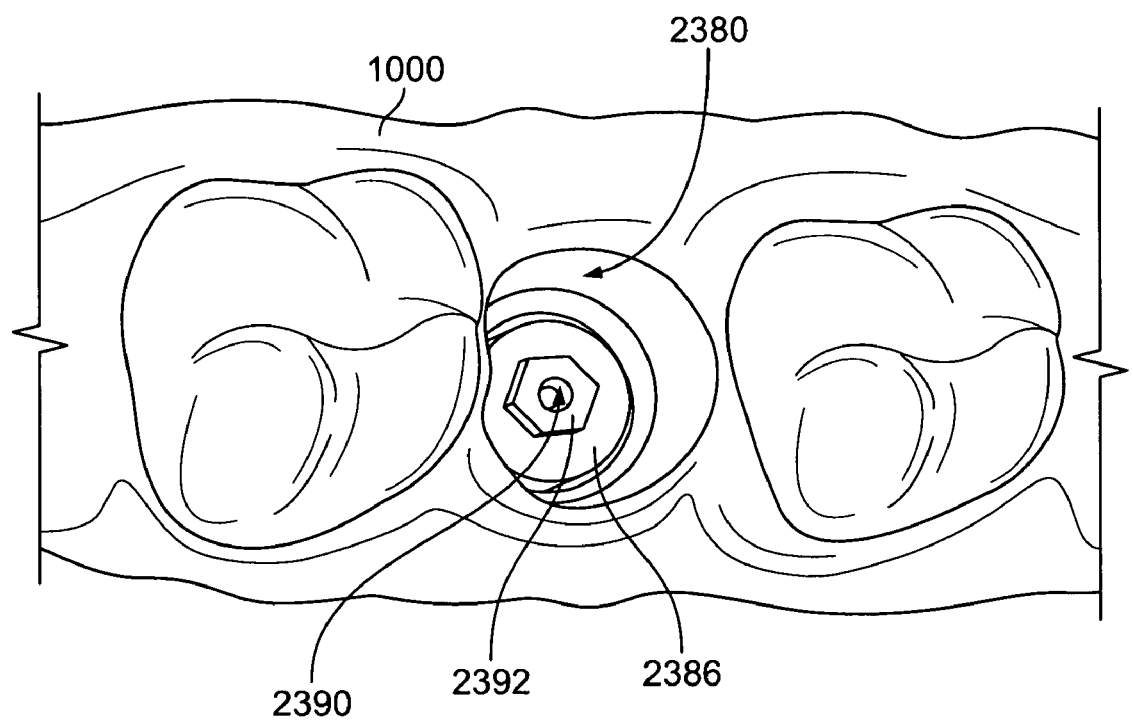
FIG. 27 illustrates the details of the opening of the physical model after the robot of FIG. 23 has placed the implant analog therein.

Once the adhesive has cured, the robot 2300 commands the gripping mechanism of the tool holder 2314 to release the implant analog holder 2384. The implant analog holder 2344 is held to the implant analog 2386 through a long screw. Thus, the operator removes the long screw such that the implant analog 2386 remains by itself within the opening 2380 (attached via the adhesive), as is shown in FIG. 27. In particular, the implant analog 2386 and its threaded bore 2390 and anti-rotational feature 2392, are located at a specific position and orientation within the opening 2380. It should be understood that the robot 2300 could also include the necessary tools (e.g. screwdriver tip) in the pallet 2350 to release the implant analog holder 2344 from the implant analog 2386 so that no operator intervention is required.

Figure 28:
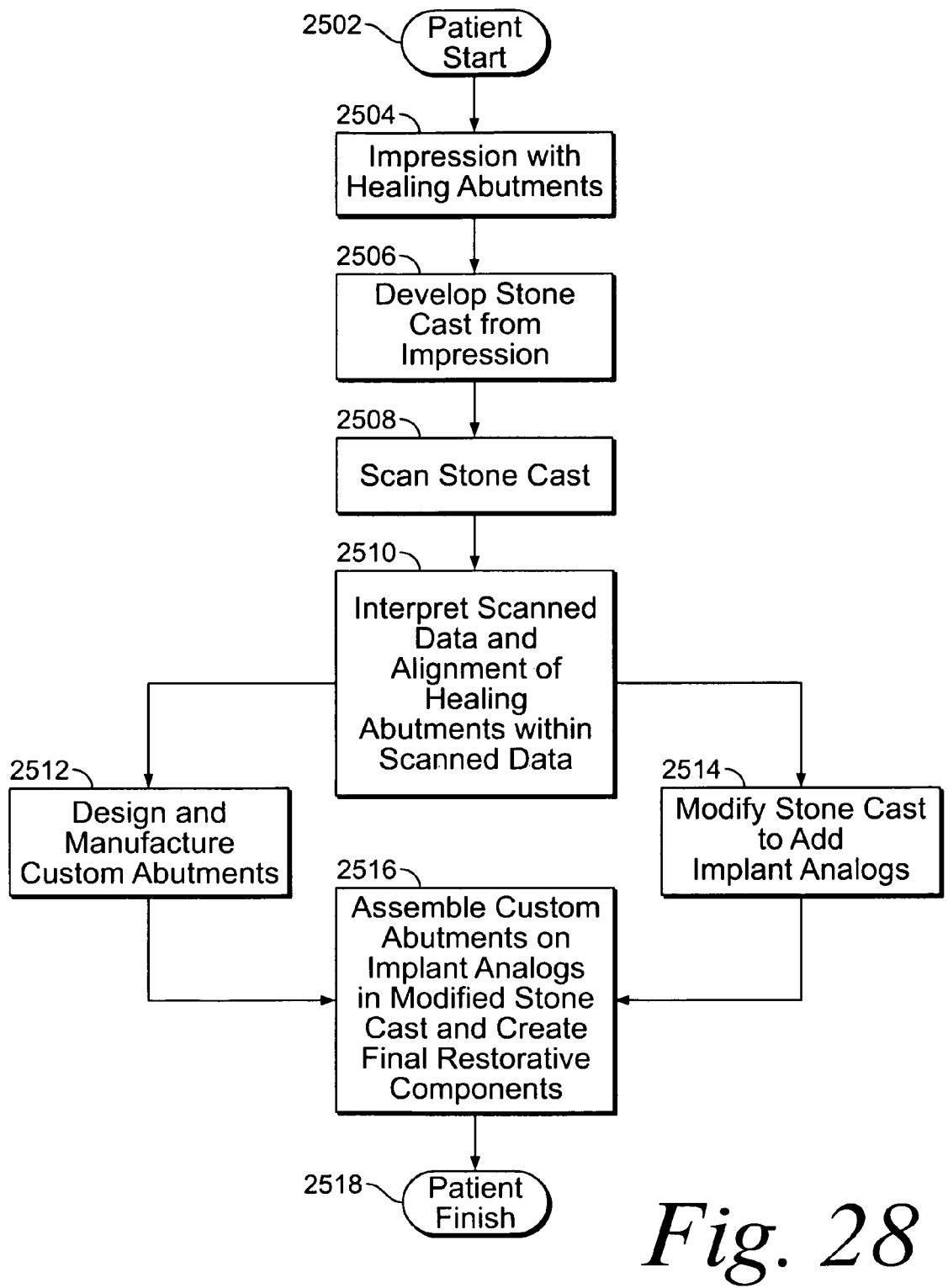
FIG. 28 illustrates a flow diagram for use in creating a custom abutment and modifying a physical model.

FIG. 28 illustrates a flowchart of the entire process that is used to create a custom abutment and the final restorative components that fit upon the custom abutment. At step 2502, a patient is fitted with a dental implant and an associated healing abutment, like those shown in FIGS. 1-7 and 9. At step 2504, an impression of the patient's mouth is taken with the healing abutment(s) installed on the implant. At step 2506, a stone cast (e.g., the stone cast 1000) of the patient's mouth is developed from the impression of the patient's mouth. The stone cast would include a stone replica of the healing abutment(s) which provides information regarding the underlying dental implant as well as the gingival opening created by the healing abutment(s). The development of the stone cast may also include the development of a stone cast of the opposing (upper or lower) teeth, which are then placed in an articulator device, as is commonly known, to locate the stone cast relative to the opposing upper or lower set of dentition.

At step 2508, the stone cast is scanned so as to produce a virtual model of the stone cast. This scanning step may also include the scanning of the cast of the opposing upper or lower dentition to constrain the height of the eventual custom abutment that is designed and manufactured. The opposing cast scan is articulated relative to the initial cast scan. The articulation can be achieved through various methods. For example, the articulation axis from the articulator used to articulate the physical casts can be stored in the computer (with respect to a common calibration standard used with the scanner and articulator) such that the opposing cast can be articulated correctly. Another example is the use of the "virtual articulation" software module available in the 3Shape Dental Designer software (3Shape A/S, Copenhagen, Denmark). This allows a set of casts to be articulated in the computer by taking an additional scan in which the casts are positioned in the articulated condition. The software uses a shape-matching algorithm to articulate the opposing cast scan relative to the initial cast scan by referencing geometry from all three scans.

At step 2510, the scanned data of the stone cast is interpreted. Further, using the marker system associated with the set of healing abutments, a virtual healing abutment that matches the scanned data of the stone replica of the healing abutments is aligned with the scanned data such that the exact location, size, and orientation of the entire healing abutment (and, thus, the underlying dental implant) is known. For example, the operator may have a library of possible healing abutments and the one that matches the size and markers at the top of the scanned healing abutment is selected to be aligned on the scanned healing abutment. Once the location and orientation of the underlying dental implant is known, the operator preferably manipulates the model to produce a 3-D CAD model of only the specific area containing the stone replica of the healing abutment(s), as is shown in FIG. 20 or 22, to decrease the amount of data required for the process.

Information resulting from step 2510 is then used for two purposes. First, it is used within step 2512 to design a virtual custom abutment (e.g., custom abutment 1604) with the use of the 3-D CAD model. The data is ultimately transferred to a milling machine to manufacture the actual custom abutment. And second, the information from step 2510 can also be sent to a robot (such as the robot 2100 in FIG. 21 or the robot 2300 in FIG. 23) at step 2514 to modify the stone cast that was developed in step 2506. As described above, this modification of the stone cast may include the development of a contoured opening in the stone cast in the area that was previously occupied by a stone replica of the healing abutment. Further, the modification may also include the placement of the implant analog, which as described above, can be accomplished by use of the same robot. In summary, step 2514 entails the methodology and processes that are generally discussed with reference to FIGS. 19-27.

At step 2516, the custom abutment that was manufactured in step 2512 can be placed on the modified stone cast created in step 2514. In doing so, the final restorative component(s) (e.g., porcelain tooth-shaped material to be cemented to the custom abutment) can be created on the custom abutment, often by a dental laboratory. The development of the final restorative component(s) take into account the adjacent teeth in the modified stone cast as well as the contour of the opening in the stone cast that leads to the implant analog. At step 2518, the custom abutment and the final restorative component(s) are then sent to the clinician who installs the custom abutment and mating restorative component(s) onto the dental implant.

As an alternate methodology to that which is shown in FIG. 28, at step 2502, an impression can be taken of the patient's mouth prior to installation of the dental implants and the associated healing abutments (e.g., the very first visit to the clinician at which the dental implant installation is recommended to the patient). The stone cast from that impression is then scanned for later usage. After a subsequent visit in which the dental implant is installed along with the associated healing abutment, a scan of the patient's mouth with the associated healing abutment is created. That scanned data of the patient's mouth is then merged, via a shape-matching algorithm (e.g., a scanner and associated software from 3Shape A/S of Copenhagen, Denmark), with the initial scan of the stone cast. The result is that there is electronic data that is analogous to the result of scanning the stone cast in step 2508 of FIG. 28. In this alternative embodiment, step 2510 to 2518 would continue as discussed above with the primary difference being that the stone cast modified by the robot 2300 would lack the stone replica of the healing abutment that was described above with respect to FIGS. 23-26 since the stone replica was taken prior to installation of the healing abutment.

As a further option to the alternative procedure in the preceding paragraph, instead of a scan of the patient's mouth with the healing abutment in place, an abutment-level impression (as in step 2504) can be taken after the healing abutment and implant are installed and the impression (or resultant stone cast) could be scanned by a lab. This scanned data could again be merged with the data set from the initial stone cast. In either of these two options, the primary advantage is that overall process can be expedited. This is due to the fact that the entity that modifies the stone model already has the stone model in hand and can begin altering the stone model with the robot once it receives the electronic transfer of the scan data from the (i) scan of the patient's mouth with the healing abutment (as described in the preceding paragraph), or (ii) the scan of the impression of the patient's mouth with the healing abutment (as described in this paragraph).

In a further alternative to either of the previous paragraphs, instead of receiving a stone cast of the patient's mouth prior to installation of the dental implant and healing abutment, the entity involved with the modification of the stone model receives a CT scan of the patient's mouth. In doing so, the CT scan allows that entity to build a physical stone model of the patient's mouth through a rapid prototyping technique. In other words, in this further alternative, there is no need to make a stone model or transfer a stone model created by an impression of the patient's mouth. The CT scan and the subsequent transfer of that scanned data allows for the creation of a model of the patient's mouth through a rapid prototyping technique.

In yet another alternative, after the patient has been fitted with the implant and the associated healing abutment, the patient receives a CT scan. That scanned data is then transferred to the entity involved with the modification is stone model. That entity then uses the data from the CT scan to create a rapid prototyping, which will ultimately serve as the stone model 1000 described above. Further, that same CT scan data can be used to design manufacture the custom abutment. In other words, in such a methodology using a CT scan of the patient's mouth that includes the healing abutment, once a rapid prototype is built from that scanned data, the methodology continues from step 2510 in FIG. 28.

Figure 29:
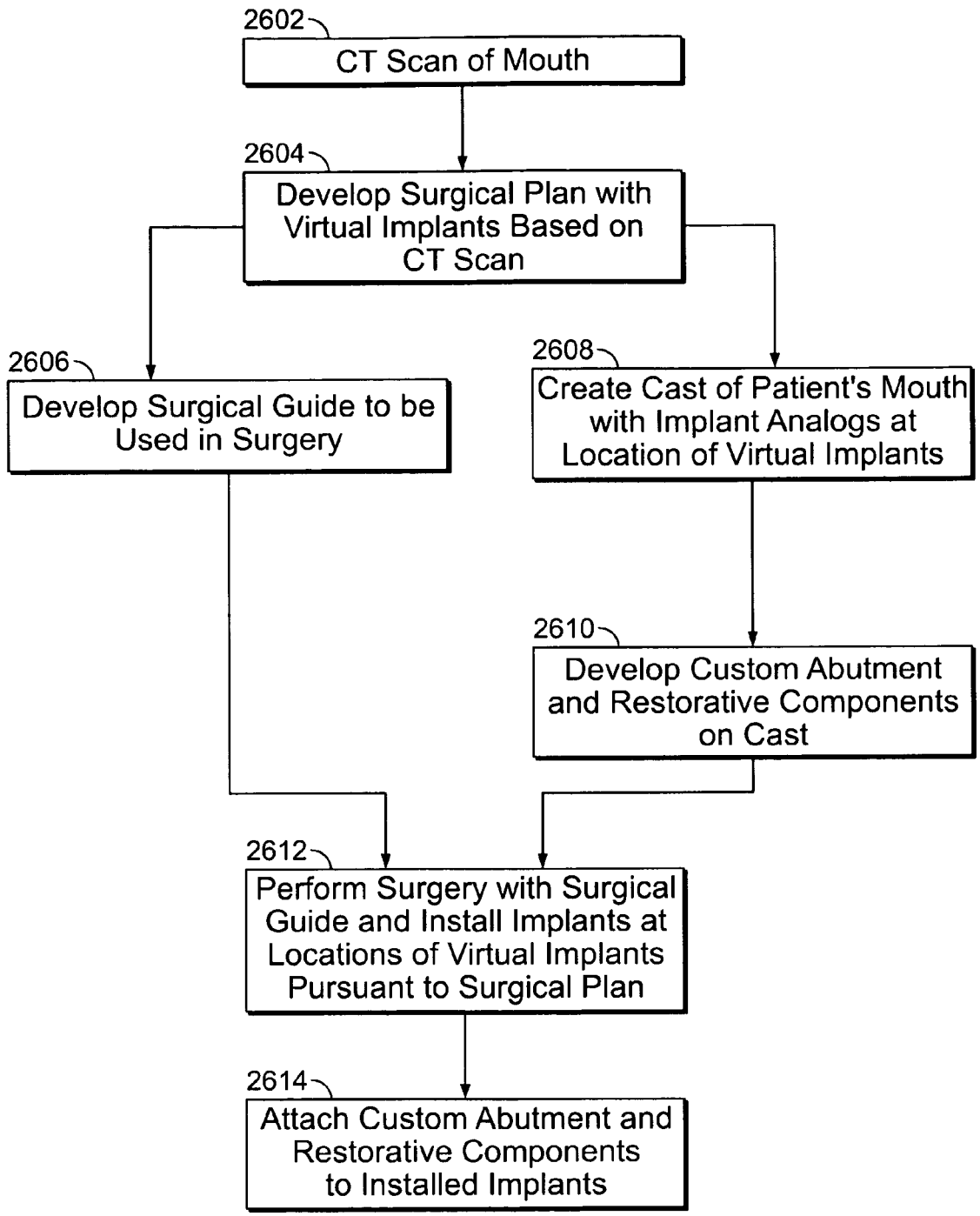
FIG. 29 illustrates a flow diagram for use in creating a custom abutment with a CT scan.

In a further alternative, no healing abutments with informational markers are necessary, as will be described with reference to FIG. 29. At step 2602, the CT scan of the patient's mouth is taken prior to installation of the implants (or any surgery). At step 2604, the CT scan data is then used to develop a surgical plan for the installation of the dental implants in the patient's mouth, which includes virtual implants "virtually" installed at certain locations of the patient's mouth. From the surgical plan, at step 2606, a surgical guide is developed that fits precisely over the patient's gingival tissue and/or dentition. The surgical guide includes holes through which tissue punches and drill bits can be inserted to create an osteotomy. Further, the dental implants can be installed at a precise location and orientation by insertion through the holes of the surgical guide that is precisely fit within the patient's mouth. As such, the CT scan allows for the virtual installation of the dental implant pursuant to the surgical plan, and the building of a surgical guide that will allow the clinician to actually install the properly sized dental implant at the location and orientation dictated by the surgical plan. One example of the use of a CT-scan to develop a surgical plan involving a surgical guide is disclosed in U.S. Patent Application Ser. No. 61/003,407, filed Nov. 16, 2007, and described in Biomet 3i's Navigator™ system product literature, "Navigator™ System For CT Guided Surgery Manual" that is publicly available, both of which are commonly owned and herein incorporated by reference in their entireties. Another example of the use of a CT-scan to develop a surgical plan is disclosed in U.S. Patent Publication No. 2006/0093988, which is herein incorporated by reference in its entirety.

Once the CT scan is created and the surgical plan with the associated virtual implants is known, at step 2608, the CT scan data and virtual implant data can be used to develop a cast, such as a rapid prototype model, that will ultimately replicate the conditions in the patient's mouth after the surgical plan is effectuated. As such, the CT scan data and the surgical plan data can be used to develop a rapid prototype model of the patient's mouth. Further, this data can also be used to install implant analogs at locations within that rapid prototype model that correspond to locations of the virtual implants dictated by the surgical plan. For example, the robot 2300 can be used to install implant analogs in the rapid prototype model as described above with reference to FIGS. 23-27. Or, the rapid prototype manufacturing method can directly incorporate an implant analog structure without the use of the robot 2300, as described in some of the previous embodiments lacking a robot. Hence, the model of the patient's mouth with the implant analogs can be developed before the patient has undergone any surgery whatsoever (i.e., without the use of the previously disclosed healing abutments having the information markers). At step 2610, the model or cast is then used to develop a custom abutment (or a bar for attachment to multiple implants and for receiving a denture) and the associated restorative components.

Once the surgical guide from step 2606 is completed, it can be transferred to the clinician for use in the patient at step 2612. Thus, the patient receives dental implants installed in accordance with the dental plan (i.e., the proper size implants, their orientation, and their location are finalized in the patient in accordance to virtual implants of the surgical plan). Further, the custom abutment and restorative components (e.g., porcelain tooth-shaped material, associated screw, etc) are transferred to the clinician and can be installed on the dental implants at step 2614. Consequently, under the methodology of FIG. 29, it is possible for custom abutment and restorative components to be installed in the patient on the same day that he or she receives the dental implants installed via the surgical guide.

While the preceding embodiments have been described for creating a final prosthesis, it is contemplated that the process may be used to create a temporary prosthesis as well.

While the preceding embodiments have been described by scanning a cast of a patient's mouth, it is also contemplated that an intra-oral scan, a CT scan, or other known type of medical scan, may be taken to generate data used for a 3-D CAD model.

While the preceding embodiments have been described using a healing abutment containing a variety of markings, it is further contemplated that a scanning abutment may be placed into a stone model before a scan is performed. According to such an embodiment, a first stone model of a patient's mouth would be made, and a portion of the first stone model corresponding to a healing abutment would be removed and replaced with a scanning abutment containing a variety of markings as previously described. A scan would then be performed of the first stone model containing the scanning abutment, and a 3-D CAD model of the patient's mouth would be created. The 3-D CAD model would then be used as previously described.

While particular embodiments and applications of the present invention have been illustrated and described, it is to be understood that the invention is not limited to the precise construction and compositions disclosed herein and that various modifications, changes, and variations may be apparent from the foregoing descriptions without departing from the spirit and scope of the invention as defined in the appended claims.

What is claimed is:

1. A method of performing guided surgery in a patient's mouth, comprising:

taking a CT-scan of the patient's mouth to develop CT-scan data;

developing, on a 3D-computer model, a surgical plan based on the CT-scan data, the surgical plan including at least one virtual implant, the virtual implant having virtual-implant location data and virtual implant orientation data corresponding to a non-rotational feature on the virtual implant;

based on the surgical plan, manufacturing a surgical guide to be placed in the patient's mouth for installing an implant in the patient's mouth at substantially the same location and orientation as the virtual implant on the 3D-computer model;

based on the CT-scan data and the virtual-implant location and orientation data from the surgical plan, manufacturing, via rapid prototyping, a physical model of the patient's mouth having an integral implant analog structure at substantially the same location and orientation as the virtual implant on the 3D-computer model, the integral implant analog structure being made of the same material as other parts of the rapid-prototyped physical model, the rapid-prototyped physical model including a contoured opening that is sized and shaped based on a size and shape of a custom abutment to be installed on the implant in the patient's mouth, the integral implant analog structure being located within the contoured opening;

developing a custom prosthesis on the physical model, the developing including mounting the custom abutment at least partially within the contoured opening and on the integral implant analog structure and using the mounted custom abutment to create the custom prosthesis, the custom prosthesis including tooth-shaped material that fits on the custom abutment;

performing surgery to place the implant in the patient's mouth as physically guided by the surgical guide in accordance with the surgical plan; and installing the custom abutment and the custom prosthesis on the implant in the patient's mouth.

2. The method of claim 1, wherein the surgical guide is manufactured to fit precisely over the patient's dentition.

3. The method of claim 1, further comprising locating the surgical guide in the patient's mouth prior to performing the surgery such that the surgical guide engages gum tissue or existing teeth in the patient's mouth.

4. The method of claim 1, wherein the surgical guide includes one or more apertures configured to receive drill bits therethrough.

5. The method of claim 4, wherein the performing surgery includes installing the implant in the patient's mouth by inserting the implant through the one or more apertures included in the surgical guide.

6. The method of claim 1, wherein each of the one or more apertures in the surgical guide is configured to receive a specifically sized implant.

7. The method of claim 1, wherein the performing surgery includes using one or more drill bits to create an osteotomy in the patient's mouth configured to receive the implant.

8. A method of developing a physical model of a mouth of a patient for use in developing a custom prosthesis for attachment to a dental implant installed in the mouth of the patient, the method comprising:

scanning the mouth of the patient to develop scan data;

by use of the scan data, developing a 3D-computer model of the mouth of the patient;

developing, by use of the 3D-computer model, a surgical plan including a virtual implant, the surgical plan including virtual-implant location data that corresponds to a location of the virtual implant in the 3D-computer model of the mouth of the patient; and by use of the 3D-computer model and the virtual-implant location data, manufacturing, via rapid prototyping, a physical model of the mouth of the patient, the physical model including an integral implant analog structure at substantially the same location as the virtual implant in the 3D-computer model, the physical model being used to develop a custom prosthesis by use of the integral implant analog structure, the integral implant analog structure being made of the same material as other parts of the rapid-prototyped physical model, the physical model including a contoured opening that is sized and shaped based on a size and shape of a custom abutment to be installed on the dental implant in the patient's mouth, the integral implant analog structure being located within the contoured opening.

9. The method of claim 8, wherein the integral implant analog structure includes a physical replica of at least a portion of the virtual implant.

10. The method of claim 8, further comprising based on the surgical plan, manufacturing a surgical guide that is configured to fit in the mouth of the patient, the surgical guide including one or more apertures.

11. The method of claim 10, further comprising positioning the surgical guide in the mouth of the patient such that the surgical guide engages at least one of gum tissue or dentition in the mouth of the patient.

12. The method of claim 11, further comprising by use of the surgical guide in accordance with the surgical plan, creating an aperture in bone tissue of the mouth of the patient that is configured to receive the dental implant.

13. The method of claim 12, further comprising by use of the surgical guide in accordance with the surgical plan, installing the dental implant into the aperture created in the bone tissue, the surgical guide aiding in installing the dental implant in the mouth of the patient at substantially the same location and orientation as the virtual implant on the 3D-computer model.

14. The method of claim 8, further comprising:

mounting the custom abutment at least partially within the contoured opening and on the integral implant analog structure; and developing the custom prosthesis on the custom abutment mounted to the physical model of the mouth of the patient, the custom prosthesis including tooth-shaped material that fits on the custom abutment.

15. The method of claim 14, further comprising performing surgery to place the implant in the mouth of the patient in accordance with the surgical plan.

16. The method of claim 15, further comprising installing the custom abutment and the custom prosthesis on the implant in the mouth of the patient.

* * * * *

UNITED STATES PATENT AND TRADEMARK OFFICE
CERTIFICATE OF CORRECTION

PATENT NO. : 8,257,083 B2  
APPLICATION NO. : 12/070922  
DATED : September 4, 2012  
INVENTOR(S) : Berckmans et al.

Page 1 of 1

It is certified that error appears in the above-identified patent and that said Letters Patent is hereby corrected as shown below:

In the Claims

In column 23, line 21 (claim 6, line 1), replace the phrase "claim 1" with the phrase -- claim 4 --.

Signed and Sealed this  
Eighteenth Day of February, 2014

Michelle K. Lee  
*Deputy Director of the United States Patent and Trademark Office*